United States Patent [19]

Shibata et al.

[11] Patent Number: 5,811,424

[45] Date of Patent: Sep. 22, 1998

[54] AMINO-ACID AMIDE DERIVATIVES, METHOD FOR PRODUCING THE SAME, AND AGRICULTURAL OR HORTICULTURAL FUNGICIDES

[75] Inventors: Masaru Shibata; Kazuhiko Sugiyama; Norihisa Yonekura, all of Iwata-gun; Junetsu Sakai, Tooda-gun; Yoshiyuki Kojima, Kakegawa; Shigeru Hayashi, Ogasa-gun, all of Japan

[73] Assignees: Kumiai Chemical Industry Co., Ltd.; Ihara Chemical Industry Co., Ltd., both of Tokyo, Japan

[21] Appl. No.: 666,474

[22] PCT Filed: Nov. 1, 1994

[86] PCT No.: PCT/JP94/01846

§ 371 Date: Jul. 1, 1996

§ 102(e) Date: Jul. 1, 1996

[87] PCT Pub. No.: WO96/13482

PCT Pub. Date: May 9, 1996

[51] Int. Cl.⁶ ........................ A61K 31/535; C07C 255/03
[52] U.S. Cl. ........................ 514/237.5; 514/542; 558/390
[58] Field of Search ........................ 558/390; 514/237.5, 514/542

[56] References Cited

U.S. PATENT DOCUMENTS 5,574,064 11/1996 Shibata et al. ........................ 514/542

Primary Examiner—Johann Richter
Assistant Examiner—Ebenezer O. Sackey
Attorney, Agent, or Firm—Oblon, Spivak, McClelland, Maier & Neustadt, P.C.

[57] ABSTRACT

The present invention provides an amino-acid amide derivative represented by the formula:

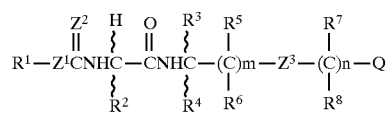

(wherein $R^1$ represents a lower alkyl group (optionally having at least one same or different substituent of a halogen atom), $R^2$ represents an ethyl group, $R^3$ represents a hydrogen atom, $R^4$ represents a hydrogen atom, $R^5$, $R^6$, and $R^7$ independently represent a hydrogen atom or a lower alkyl group, $R^8$ represents a hydrogen atom, $Z^1$ and $Z^2$ independently represent an oxygen atom or a sulfur atom, $Z^3$ represents an oxygen atom or a sulfur atom, Q represents a phenyl group, m represents an integer from 0 to 2, and n represents 0 or 1), and an agricultural or horticultural fungicide including an effective amount of the same. The amino-acid amide derivatives exhibit a superior control of plant diseases, particularly downy mildew and late blight, and are not harmful to plants.

25 Claims, No Drawings

AMINO-ACID AMIDE DERIVATIVES, METHOD FOR PRODUCING THE SAME, AND AGRICULTURAL OR HORTICULTURAL FUNGICIDES

This application is a 371 of PCT/JP94/01846 filed on Nov. 1, 1994.

FIELD OF THE INVENTION

The present invention relates to novel amino-acid amide derivatives as well as to agricultural or horticultural fungicides containing the same as active ingredients.

BACKGROUND ART

Heretofore, it is known that the amino-acid amide derivatives such as $N^2$-tert-butoxycarbonyl-$N^1$-(2-phenoxyethyl)-D-alanine and $N^2$-tert-butoxycarbonyl-$N^1$-(2-phenylthioethyl)-D-alanine (Japanese Patent Application, First Publication, No. Sho 62-89696) are intermediates for medicines; however, the utility of the amino-acid amide derivatives are not known. In addition, it is known that the amino-acid amide derivatives such as N-(tert-butoxycarbonyl)-L-valine-1-(4-methylphenyl)ethylamide (Japanese Patent Application, First Publication, No. Hei 3-5451), $N^2$-(4-chlorophenoxycarbonyl)-$N^1$-[1-(4-chlorophenyl)ethyl]-L-valinamide (Japanese Patent Application, First Publication, No. Hei 3-153657), and the like are useful for biocides.

However, the fungicidal activities of fungicides may become degraded because of the emergence of resistant fungi after repeated uses of the fungicides. For this reason, as well as because of environmental problems, it is desired to provide a novel fungicide which can efficiently control harmful fungi even at a low concentration.

DISCLOSURE OF THE INVENTION

In order to develop a fungicide possessing fungicidal activity superior to that of known fungicides, the present inventors have synthesized various amino-acid amide derivatives and have carried out extensive research in connection with their effects on the biological activities of fungi. As a result, we have found that the compounds according to the present invention, possessing a substituted or non-substituted phenoxy group, a substituted or non-substituted benzyloxy group, a substituted or non-substituted alkoxy group, and the like, as a terminal group, exhibit a broad spectrum of anti-fungal activity especially against cucumber downy mildew, grape downy mildew, and tomato late blight in small amounts, while at the same time do not hinder desirable plant growth.

According to an aspect of the present invention, there is provided (1) an amino-acid amide derivative represented by the formula [I]:

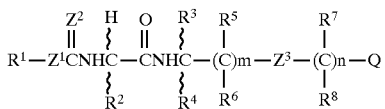

wherein $R^1$ represents (a) a lower alkyl group (optionally having at least one same or different substituent selected from the group consisting of a halogen atom, an alkoxy group, and a cyano group), (b) a lower alkenyl group, (c) a lower alkynyl group, (d) a cycloalkyl group (optionally having at least one substituent selected from the group consisting of methyl group and a halogen atom), (e) a cycloalkylalkyl group, (f) a cycloalkenyl group, (g) a cyclic ether group, (h) a phenyl group (optionally having at least one same or different substituent selected from the group consisting of a halogen atom, a lower alkyl group which may be substituted with a same or different halogen atom, a lower alkoxy group which may be substituted with a same or different halogen atom, a cyano group, and a nitro group), (i) an aralkyl group (optionally having at least one same or different substituent selected from the group consisting of a methyl group, a cyano group, and a nitro group), or (j) a heterocyclic group, $R^2$ represents a lower alkyl group, a lower alkenyl group, a cycloalkyl group, or a phenyl group (optionally having at least one substituent of halogen atom), $R^3$ represents a hydrogen atom or a lower alkyl group, $R^4$ represents a hydrogen atom, a lower alkyl group, or a cyano group, $R^5$, $R^6$, and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $Z^1$ and $Z^2$ independently represent an oxygen atom or a sulfur atom, $Z^3$ represents an oxygen atom, a sulfur atom, a group

(wherein $R^{10}$ represents a hydrogen atom, a methyl group, an acetyl group, a benzoyl group, a methoxycarbonyl group, or a methoxymethyl group), a sulfinyl group, a sulfonyl group, a group —C(O)O—, a group

(wherein $R^{11}$ represents a hydrogen atom or a lower alkyl group),

Q represents (a) a phenyl group [optionally having at least one same or different substituent selected from the group consisting of a halogen atom, a lower alkyl group which may be substituted with at least one same or different halogen atom, a lower alkoxy group which may be substituted with a same or different halogen atom, a cyano group, a nitro group, a lower alkoxycarbonyl group, a methylsulfonyl group, a methylsulfinyl group, a methylthio group which may be substituted with a halogen atom, a dimethylamino group, a phenylsulfonyl group, an acyl group, and a phenyl group], (b) a cyclic ether group, (c) a heterocyclic group (optionally having a substituent selected from the group consisting of a halogen atom, an alkyl group, a trifluoromethyl group, and a nitro group), or (d) a condensed heterocyclic group optionally having a substituent selected from the group consisting of a halogen atom and a nitro group, m represents an integer from 0 to 2, and n represents 0 or 1, (2) a process for preparing an amino-acid amide derivative represented by the formula:

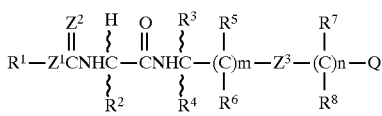

wherein $R^1, R^2, R^3, R^4, R^5, R^6, R^7, R^8, Z^1, Z^2, Z^3, Q, m$, and n have the same meanings as defined in (1), comprising the step of: reacting an amino acid derivative or the amino acid derivative with an activated carboxyl group, represented by the formula:

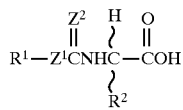

with an amine represented by the formula:

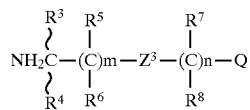

in the presence of a catalyst and/or a base as required, (3) a process for preparing an amino-acid amide derivative represented by the formula:

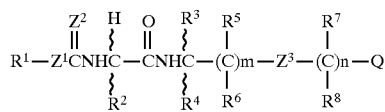

wherein $R^1, R^2, R^3, R^4, R^5, R^6, R^7, R^8, Z^1, Z^2, Z^3, Q, m$, and n have the same meanings as defined in (1), and Y represents a halogen atom, a 4,6-dimethylpyrimidinylthio group, an $R^1OC(O)O-$ group, or a

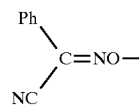

group, (wherein Ph represents a phenyl group), comprising the step of: reacting a compound represented by the formula:

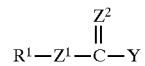

with an amine represented by the formula:

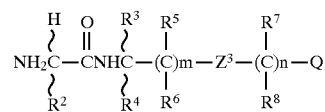

or an inorganic acid salt of the same such as hydrochloride or an organic acid salt of the same such as tosylate, and (4) an agricultural or horticultural fungicide which includes an effective amount of an amino-acid amide derivative as recited in (1).

The terms employed in the present invention are defined as follows.

The term "lower alkyl group" is used herein to mean a straight or branched alkyl group possessing 1 to 6 carbon atoms including, but not limited to, a methyl group, ethyl group, propyl group, isopropyl group, butyl group, isobutyl group, sec-butyl group, tert-butyl group, pentyl group, 1-methylbutyl group, 2-methylbutyl group, 3-methylbutyl group, 2,2-dimethylpropyl group, 1,1-dimethylpropyl group, 1-ethylpropyl group, hexyl group, or the like.

The term "halogen atom" is used herein to mean a fluorine atom, chlorine atom, bromine atom, or iodine atom.

The term "lower alkenyl group" is used herein to mean a straight or branched alkenyl group possessing 2 to 6 carbon atoms and including, but not limited to, a vinyl group, 1-propenyl group, 2-propenyl group, isopropenyl group, 1-butenyl group, 2-butenyl group, 3-butenyl group, 1-methyl-1-propenyl group, 2-methylpropenyl group, 1-ethylvinyl group, or the like.

The term "lower alkynyl group" is used herein to mean a straight or branched alkynyl group possessing 2 to 6 carbon atoms and including, for example, an ethynyl group, propynyl group, butynyl group, 1-methyl-2-propynyl group, or the like.

The term "cycloalkyl group" is used herein to mean a cycloalkyl group possessing 3 to 8 carbon atoms and including, but not limited to, a cyclopropyl group, cyclobutyl group, cyclopentyl group, cyclohexyl group, cycloheptyl group, or the like.

The term "cycloalkenyl group" is used herein to mean a cycloalkenyl group possessing 4 to 8 carbon atoms and including, for example, a cyclobutenyl group, cyclopentenyl group, cyclohexenyl group, cycloheptenyl group, or the like.

The term "aralkyl group" is used herein to mean an aralkyl group possessing 7 to 8 carbon atoms and including, but not limited to, a benzyl group, phenethyl group, or the like.

The term "cyclic ether group" is used herein to mean a cyclic ether group possessing 2 to 6 carbon atoms and including, for example, an oxiranyl group, oxetanyl group, tetrahydrofuranyl group, tetrahydropyranyl group, or the like.

The term "heterocyclic group" is used herein to mean a 5-membered or 6-membered ring including one or two hetero atoms consisting of a nitrogen atom, an oxygen atom, and a sulfur atom and including, for example, a pyridinyl group, a pyrimidinyl group, a furyl group, a thienyl group, or the like.

The term "condensed heterocyclic group" is used herein to mean a bicyclic compound consisting of 5-membered and/or 6-membered rings including one or two hetero atoms of a nitrogen atom, an oxygen atom, and a sulfur atom and including, but not limited to, a benzofuranyl group, a benzothienyl group, a quinolinyl group, or the like.

The preferred compounds of the present invention are represented by formula [I], wherein $R^1$ represents a straight or branched alkyl group possessing 2 to 6 carbon atoms, a straight or branched alkenyl group possessing 3 carbon atoms, a cycloalkyl group possessing 5 to 6 carbon atoms, or an optionally substituted phenyl group; $R^2$ represents an ethyl group, a propyl group, an isopropyl group, or a sec-butyl group; $R^3$ represents a hydrogen atom or a methyl group; $R^4$ represents a hydrogen atom or a methyl group; $R^5$ represents a hydrogen atom or a methyl group; $R^6$ represents a hydrogen atom or a methyl group; Q represents an optionally substituted phenyl group; m represents an integer of 0 or 1; n represents 0; $Z^1$, $Z^2$, and $Z^3$ represent an oxygen atom or a sulfur atom; and the amino acid is an L-isomer.

The compounds represented by formula [I] according to the present invention can exist in stereoisomers by virtue of the presence of two or more chiral centers in a molecule. The present invention relates to all such stereoisomers, including diastereomers, enantiomers, and mixtures thereof, which can be separated by appropriate methods.

Next, representative examples of the compounds represented by Formula [I] according to the present invention are listed in Tables 1~13. However, it should be understood that the invention is not limited to these compounds. Compound Numbers given in the Tables will be referred to in the subsequent description.

In Tables 1 to 12, Compound Nos. 108, 433, 456, 459~462, 464, 467, 470, 471, 472, and 475 possess D,L-configurational amino acid moieties; Compound No. 109 possesses a D-configurational amino acid moiety; and the compounds other than the compounds described above possess L-configurational amino acid moieties. In Compound Nos. 233~238 and 425~427, the acid moieties of the amino-acid amide derivatives are (2S)-butyric acids.

Compound Nos. 33, 345, and 346; Compound Nos. 107, 116, and 117; Compound Nos. 135, 395, and 396; Compound Nos. 228, 414, and 415; and Compound Nos. 452, 453, and 454 are mixtures of diastereomers, and are also individual diastereomers.

In addition, Compound Nos. 26 and 27; Compound Nos. 45 and 356; Compound Nos. 335 and 336; Compound Nos. 397 and 401; and Compound Nos. 409 and 410 are mixtures of diastereomers, and are also one of the individual diastereomers.

Compound No. 108 is a mixture of four isomers and Compound No. 433 is a mixture of two isomers.

Compound Nos. 483~501, 504, 505, 510~518, 521, and 522 form a part of L-Val-DL-Ala; Compound Nos. 502, 503, 508, 509, 519, and 525 form a part of L-Val-D-Ala; Compound No. 520 forms a part of L-Val-L-Ala; Compound Nos. 506 and 523 form a part of L-Ile-D-Ala; Compound No. 526 forms a part of L-Val-Gly; and Compound Nos. 507 and 524 form a part of (2S)-butylyl-D-Ala.

In the tables of the present specification, the expressions "$C_3H_7$-i", "$C_4H_9$-t", "$C_4H_9$-s", and "$C_4H_9$-i" are used to indicate an isopropyl group, a tert-butyl group, a sec-butyl group, and an isobutyl group, respectively.

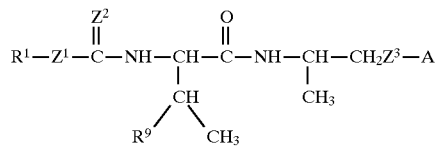

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 1 | $C_4H_9$-t | $CH_3$ | O | O | O | phenyl | 88–92 |
| 2 | $C_4H_9$-t | $CH_3$ | O | O | O | 2-Cl-phenyl | 98–100 |
| 3 | $C_4H_9$-t | $CH_3$ | O | O | O | 3-Cl-phenyl | 1.5051 |
| 4 | $C_4H_9$-t | $CH_3$ | O | O | O | 4-Cl-phenyl | 97–98 |

-continued
| Compound No. | R¹ | R⁹ | Z¹ | Z² | Z³ | A | Melting Point (°C.) or Reflective Index ($n_D^{20}$) |
|---|---|---|---|---|---|---|---|
| 5 | $C_4H_9$-t | $CH_3$ | O | O | O | 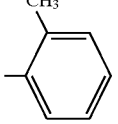 | 77–80 |
| 6 | $C_4H_9$-t | $CH_3$ | O | O | O | 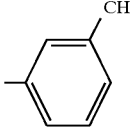 | 1.5051 |
| 7 | $C_4H_9$-t | $CH_3$ | O | O | O | 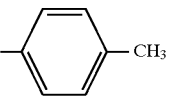 | 99–101 |
| 8 | $C_4H_9$-t | $CH_3$ | O | O | O | 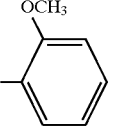 | 86–89 |
| 9 | $C_4H_9$-t | $CH_3$ | O | O | O | 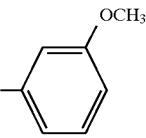 | 1.4899 |
| 10 | $C_4H_9$-t | $CH_3$ | O | O | O | 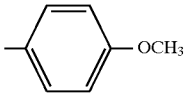 | 86–89 |
| 11 | $C_4H_9$-t | $CH_3$ | O | O | O | 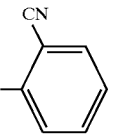 |  |
| 12 | $C_4H_9$-t | $CH_3$ | O | O | O | 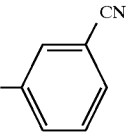 | 83–87 |
| 13 | $C_4H_9$-t | $CH_3$ | O | O | O | 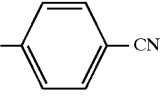 | 53–56 |
| 14 | $C_4H_9$-t | $CH_3$ | O | O | O | 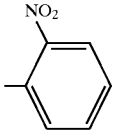 | 1.5081 |
| 15 | $C_4H_9$-t | $CH_3$ | O | O | O | 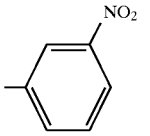 | 112–114 |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 16 | $C_4H_9$-t | $CH_3$ | O | O | O | 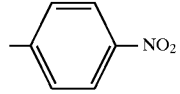 | 105–107 |
| 17 | $C_4H_9$-t | $CH_3$ | O | O | O | 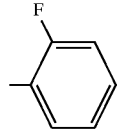 | 95–97 |
| 18 | $C_4H_9$-t | $CH_3$ | O | O | O | 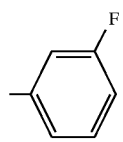 | 89–92 |
| 19 | $C_4H_9$-t | $CH_3$ | O | O | O | 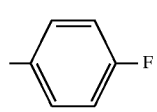 | 85–89 |
| 20 | $C_4H_9$-t | $CH_3$ | O | O | O | 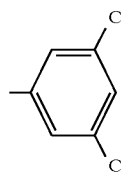 | 99–100 |
| 21 | $C_4H_9$-t | $CH_3$ | O | O | O | 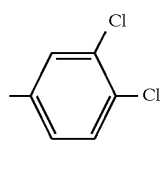 | 102–104 |
| 22 | $C_4H_9$-t | $CH_3$ | O | O | O | 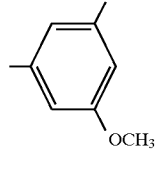 | 87–91 |
| 23 | $C_4H_9$-t | $CH_3$ | O | O | O | 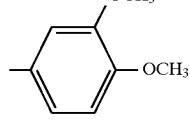 | 88–90 |
| 24 | $C_4H_9$-t | $CH_3$ | O | O | O | 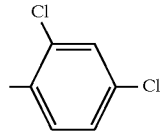 | 98–103 |
| 25 | $C_4H_9$-t | $CH_3$ | O | O | O | 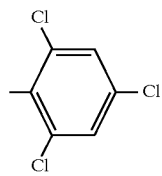 | 120–125 |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 26 | $C_4H_9$-t | $CH_3$ | O | O | O | 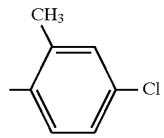 | 108–110 |
| 27 | $C_4H_9$-t | $CH_3$ | O | O | O | 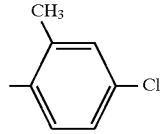 | 143–146 |
| 28 | $C_4H_9$-t | $CH_3$ | O | O | O | 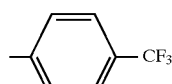 | 115–117 |
| 29 | $C_4H_9$-t | $CH_3$ | O | O | O | 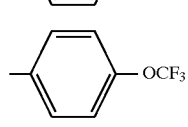 | 94–98 |
| 30 | $C_3H_7$-i | $CH_3$ | O | O | O | 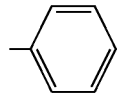 | |
| 31 | $C_3H_7$-i | $CH_3$ | O | O | O | 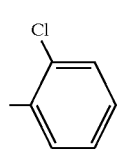 | |
| 32 | $C_3H_7$-i | $CH_3$ | O | O | O | 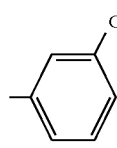 | |
| 33 | $C_3H_7$-i | $CH_3$ | O | O | O | 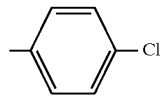 | 149–152 |
| 34 | $C_3H_7$-i | $CH_3$ | O | O | O | 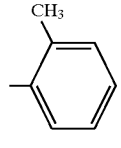 | |
| 35 | $C_3H_7$-i | $CH_3$ | O | O | O | 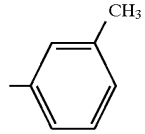 | |
| 36 | $C_3H_7$-i | $CH_3$ | O | O | O | 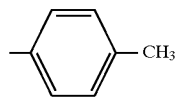 | |
| 37 | $C_3H_7$-i | $CH_3$ | O | O | O | 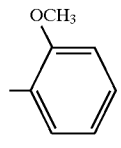 | |

-continued

| Compound No. | R¹ | R⁹ | Z¹ | Z² | Z³ | A | Melting Point (°C.) or Refractive Index ($n_D^{20}$) |
|---|---|---|---|---|---|---|---|
| 38 | $C_3H_7$-i | $CH_3$ | O | O | O | 3-methoxyphenyl | |
| 39 | $C_3H_7$-i | $CH_3$ | O | O | O | 4-methoxyphenyl | |
| 40 | $C_3H_7$-i | $CH_3$ | O | O | O | 2-cyanophenyl | |
| 41 | $C_3H_7$-i | $CH_3$ | O | O | O | 3-cyanophenyl | |
| 42 | $C_3H_7$-i | $CH_3$ | O | O | O | 4-cyanophenyl | 149–152 |
| 43 | $C_3H_7$-i | $CH_3$ | O | O | O | 2-nitrophenyl | |
| 44 | $C_3H_7$-i | $CH_3$ | O | O | O | 3-nitrophenyl | |
| 45 | $C_3H_7$-i | $CH_3$ | O | O | O | 4-nitrophenyl | not determined |
| 46 | $C_3H_7$-i | $CH_3$ | O | O | O | 2-fluorophenyl | |
| 47 | $C_3H_7$-i | $CH_3$ | O | O | O | 3-fluorophenyl | |
| 48 | $C_3H_7$-i | $CH_3$ | O | O | O | 4-fluorophenyl | |

-continued

| Compound No. | R[1] | R[0] | Z[1] | Z[2] | Z[3] | A | Melting Point (°C.) or Reflective Index ($n_D^{20}$) |
|---|---|---|---|---|---|---|---|
| 49 | $C_2H_5$ | $CH_3$ | O | O | O | 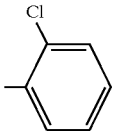 2-Cl-phenyl | |
| 50 | $C_2H_5$ | $CH_3$ | O | O | O | 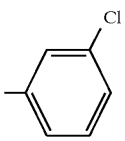 3-Cl-phenyl | |
| 51 | $C_2H_5$ | $CH_3$ | O | O | O | 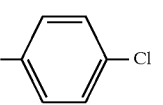 4-Cl-phenyl | |
| 52 | $C_2H_5$ | $CH_3$ | O | O | O | 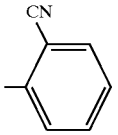 2-CN-phenyl | |
| 53 | $C_2H_5$ | $CH_3$ | O | O | O | 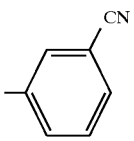 3-CN-phenyl | |
| 54 | $C_2H_5$ | $CH_3$ | O | O | O | 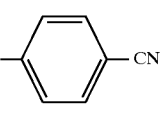 4-CN-phenyl | 112–115 |
| 55 | $C_2H_5$ | $CH_3$ | O | O | O | 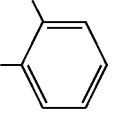 2-$NO_2$-phenyl | |
| 56 | $C_2H_5$ | $CH_3$ | O | O | O | 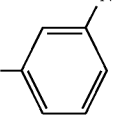 3-$NO_2$-phenyl | |
| 57 | $C_2H_5$ | $CH_3$ | O | O | O | 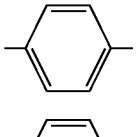 4-$NO_2$-phenyl | |
| 58 | $C_4H_9$-s | $CH_3$ | O | O | O | 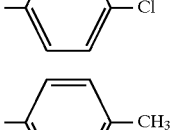 4-Cl-phenyl | |
| 59 | $C_4H_9$-s | $CH_3$ | O | O | O | 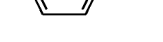 4-$CH_3$-phenyl | |
| 60 | $C_4H_9$-s | $CH_3$ | O | O | O | 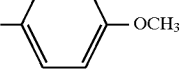 4-$OCH_3$-phenyl | |

-continued

| Compound No. | $R^1$ | $R^9$ | $Z^1$ | $Z^2$ | $Z^3$ | A | Melting Point (°C.) or Refractive Index ($n_D^{20}$) |
|---|---|---|---|---|---|---|---|
| 61 | $C_4H_9$-s | $CH_3$ | O | O | O |  | |
| 62 | $C_4H_9$-s | $CH_3$ | O | O | O |  | |
| 63 | $C_4H_9$-s | $CH_3$ | O | O | O |  | 140–143 |
| 64 | $C_4H_9$-s | $CH_3$ | O | O | O | 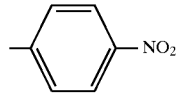 | |
| 65 | $C_4H_9$-s | $CH_3$ | O | O | O |  | |
| 66 | $C_4H_9$-s | $CH_3$ | O | O | O | 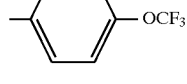 | |
| 67 | $C_4H_9$-s | $CH_3$ | O | O | O |  | |
| 68 | $C_4H_9$-s | $CH_3$ | O | O | O | 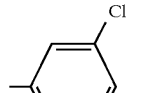 | |
| 69 | $-\underset{\underset{CH_3}{\vert}}{C}=CH_2$ | $CH_3$ | O | O | O | 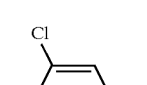 | |
| 70 | $-\underset{\underset{CH_3}{\vert}}{C}=CH_2$ | $CH_3$ | O | O | O | 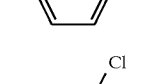 | |
| 71 | $-\underset{\underset{CH_3}{\vert}}{C}=CH_2$ | $CH_3$ | O | O | O | 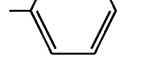 | |
| 72 | $-\underset{\underset{CH_3}{\vert}}{C}=CH_2$ | $CH_3$ | O | O | O | 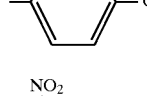 | |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 73 | -C(CH₃)=CH₂ | CH₃ | O | O | O | 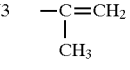 3-NO₂-C₆H₄ | |
| 74 | -C(CH₃)=CH₂ | CH₃ | O | O | O | 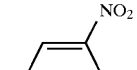 4-NO₂-C₆H₄ | |
| 75 | -C(CH₃)=CH₂ | CH₃ | O | O | O | 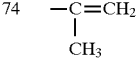 2-CN-C₆H₄ | |
| 76 | -C(CH₃)=CH₂ | CH₃ | O | O | O | 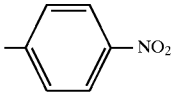 3-CN-C₆H₄ | |
| 77 | -C(CH₃)=CH₂ | CH₃ | O | O | O | 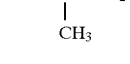 4-CN-C₆H₄ | 82–86 |
| 78 | -C(CH₃)=CH₂ | CH₃ | O | O | O | 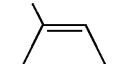 4-CF₃-C₆H₄ | |
| 79 | -C(CH₃)=CH₂ | CH₃ | O | O | O | 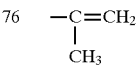 4-OCF₃-C₆H₄ | |
| 80 | cyclopentyl | CH₃ | O | O | O | 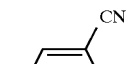 2-Cl-C₆H₄ | |
| 81 | cyclopentyl | CH₃ | O | O | O | 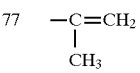 3-Cl-C₆H₄ | |
| 82 | cyclopentyl | CH₃ | O | O | O | 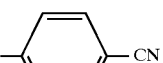 4-Cl-C₆H₄ | |
| 83 | cyclopentyl | CH₃ | O | O | O | 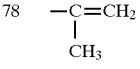 2-NO₂-C₆H₄ | |
| 84 | cyclopentyl | CH₃ | O | O | O | 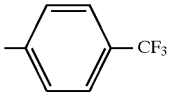 3-NO₂-C₆H₄ | |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 85 | cyclopentyl- | CH₃ | O | O | O | -C₆H₄-NO₂ (para) | |
| 86 | cyclopentyl- | CH₃ | O | O | O | -C₆H₄-CN (ortho) | |
| 87 | cyclopentyl- | CH₃ | O | O | O | -C₆H₄-CN (meta) | |
| 88 | cyclopentyl- | CH₃ | O | O | O | -C₆H₄-CN (para) | 145–148 |
| 89 | cyclohexyl- | CH₃ | O | O | O | -C₆H₄-Cl (ortho) | |
| 90 | cyclohexyl- | CH₃ | O | O | O | -C₆H₄-Cl (meta) | |
| 91 | cyclohexyl- | CH₃ | O | O | O | -C₆H₄-Cl (para) | |
| 92 | cyclohexyl- | CH₃ | O | O | O | -C₆H₄-NO₂ (ortho) | |
| 93 | cyclohexyl- | CH₃ | O | O | O | -C₆H₄-NO₂ (meta) | |
| 94 | cyclohexyl- | CH₃ | O | O | O | -C₆H₄-NO₂ (para) | |
| 95 | cyclohexyl- | CH₃ | O | O | O | -C₆H₄-CN (ortho) | |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 96 | cyclohexyl | CH₃ | O | O | O | phenyl-CN (meta) | |
| 97 | cyclohexyl | CH₃ | O | O | O | phenyl-CN (para) | 158–162 |
| 98 | phenyl | CH₃ | O | O | O | phenyl | 123–126 |
| 99 | phenyl | CH₃ | O | O | O | phenyl-Cl (ortho) | |
| 100 | phenyl | CH₃ | O | O | O | phenyl-Cl (meta) | |
| 101 | phenyl | CH₃ | O | O | O | phenyl-Cl (para) | 165–170 |
| 102 | phenyl | CH₃ | O | O | O | phenyl-NO₂ (ortho) | |
| 103 | phenyl | CH₃ | O | O | O | phenyl-NO₂ (meta) | |
| 104 | phenyl | CH₃ | O | O | O | phenyl-NO₂ (para) | 166–169 |
| 105 | phenyl | CH₃ | O | O | O | phenyl-CN (ortho) | |
| 106 | phenyl | CH₃ | O | O | O | phenyl-CN (meta) | |
| 107 | phenyl | CH₃ | O | O | O | phenyl-CN (para) | 142–146 |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 108 | 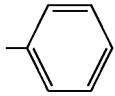 | CH₃ | O | O | O | 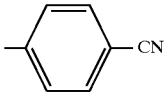 —CN | 158–162 |
| 109 | 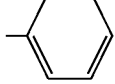 | CH₃ | O | O | O | 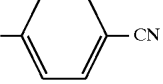 —CN | 128–133 |
| 110 | 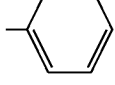 | CH₃ | O | O | O | 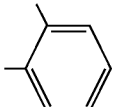 F | |
| 111 | 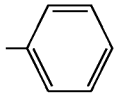 | CH₃ | O | O | O | 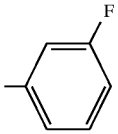 F | |
| 112 | 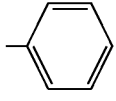 | CH₃ | O | O | O | 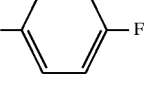 —F | 137–142 |
| 113 | 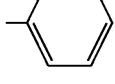 | CH₃ | O | O | O | 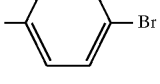 —Br | |
| 114 | 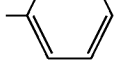 | CH₃ | O | O | O | 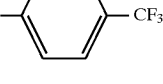 —CF₃ | 151–155 |
| 115 | 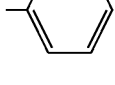 | CH₃ | O | O | O | 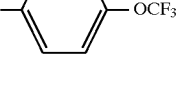 —OCF₃ | 144–147 |
| 116 |  | CH₃ | O | O | O |  —CN | 145–147 |
| 117 | 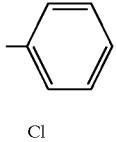 | CH₃ | O | O | O | 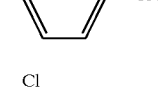 —CN | 166–170 |
| 118 | Cl 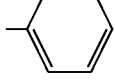 | CH₃ | O | O | O | Cl 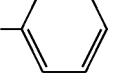 | |
| 119 | Cl 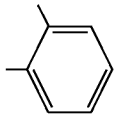 | CH₃ | O | O | O | Cl 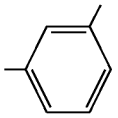 | |

-continued

| Compound No. | R¹ | R⁹ | Z¹ | Z² | Z³ | A | Melting Point (°C.) or Reflactive Index ($n_D^{20}$) |
|---|---|---|---|---|---|---|---|
| 120 | 2-Cl-phenyl | CH₃ | O | O | O | 4-Cl-phenyl | |
| 121 | 2-Cl-phenyl | CH₃ | O | O | O | 2-NO₂-phenyl | |
| 122 | 2-Cl-phenyl | CH₃ | O | O | O | 3-NO₂-phenyl | |
| 123 | 2-Cl-phenyl | CH₃ | O | O | O | 4-NO₂-phenyl | |
| 124 | 2-Cl-phenyl | CH₃ | O | O | O | 4-CN-phenyl | 137–142 |
| 125 | 2-Cl-phenyl | CH₃ | O | O | O | 4-F-phenyl | |
| 126 | 2-Cl-phenyl | CH₃ | O | O | O | 4-Br-phenyl | |
| 127 | 3-Cl-phenyl | CH₃ | O | O | O | 4-Cl-phenyl | |
| 128 | 3-Cl-phenyl | CH₃ | O | O | O | 4-NO₂-phenyl | |
| 129 | 3-Cl-phenyl | CH₃ | O | O | O | 4-CN-phenyl | 114–117 |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 130 | 3-Cl-C₆H₄- | CH₃ | O | O | O | 4-F-C₆H₄- | |
| 131 | 3-Cl-C₆H₄- | CH₃ | O | O | O | 4-Br-C₆H₄- | |
| 132 | 3-Cl-C₆H₄- | CH₃ | O | O | O | 4-CF₃-C₆H₄- | |
| 133 | 4-Cl-C₆H₄- | CH₃ | O | O | O | 4-Cl-C₆H₄- | |
| 134 | 4-Cl-C₆H₄- | CH₃ | O | O | O | 4-NO₂-C₆H₄- | 133–138 |
| 135 | 4-Cl-C₆H₄- | CH₃ | O | O | O | 4-CN-C₆H₄- | 156–160 |
| 136 | 4-Cl-C₆H₄- | CH₃ | O | O | O | 4-F-C₆H₄- | |
| 137 | 4-Cl-C₆H₄- | CH₃ | O | O | O | 4-Br-C₆H₄- | |
| 138 | C₆H₅- | CH₃ | O | O | O | 4-(C(O)OCH₃)-C₆H₄- | |
| 139 | C₆H₅- | CH₃ | O | O | O | 4-(C(O)OC₂H₅)-C₆H₄- | |
| 140 | C₆H₅- | CH₃ | O | O | O | 4-(S(O)₂CH₃)-C₆H₄- | |
| 141 | C₆H₅- | CH₃ | O | O | O | 4-(S(O)CH₃)-C₆H₄- | |
| 142 | C₆H₅- | CH₃ | O | O | O | 4-(SCH₃)-C₆H₄- | |

-continued
| Compound No. | R¹ | R⁹ | Z¹ | Z² | Z³ | A | Melting Point (°C.) or Reflective Index ($n_D^{20}$) |
|---|---|---|---|---|---|---|---|
| 143 | 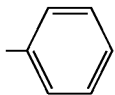 | CH₃ | O | O | O | 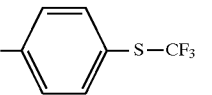 —S—CF₃ | |
| 144 | 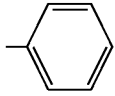 | CH₃ | O | O | O | 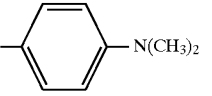 —N(CH₃)₂ | |
| 145 | 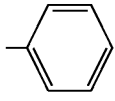 | CH₃ | O | O | O | 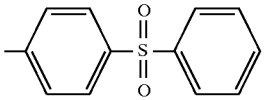 | |
| 146 | 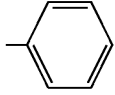 | CH₃ | O | O | O | 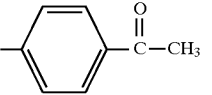 | |
| 147 | 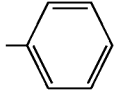 | CH₃ | O | O | O | 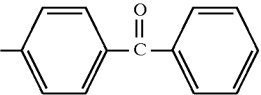 | |
| 148 | 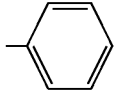 | CH₃ | O | O | O | 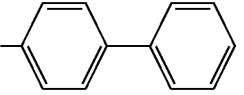 | |
| 149 | 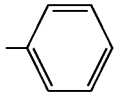 | CH₃ | O | O | O | 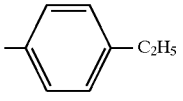 —C₂H₅ | |
| 150 | 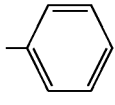 | CH₃ | O | O | O | 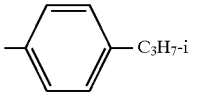 —C₃H₇-i | |
| 151 | 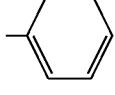 | CH₃ | O | O | O | 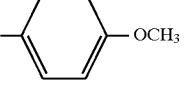 —OCH₃ | |
| 152 | 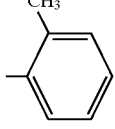 | CH₃ | O | O | O | 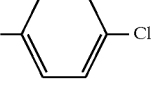 —Cl | |
| 153 | 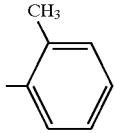 | CH₃ | O | O | O | 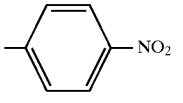 —NO₂ | |
| 154 | 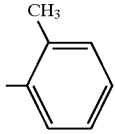 | CH₃ | O | O | O | 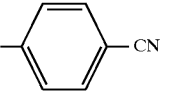 —CN | 146–150 |
| 155 | 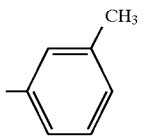 | CH₃ | O | O | O | 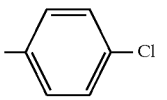 —Cl | |

-continued

| Compound No. | R¹ | R⁹ | Z¹ | Z² | Z³ | A | Melting Point (°C.) or Refractive Index ($n_D^{20}$) |
|---|---|---|---|---|---|---|---|
| 156 | 3-methylphenyl | CH₃ | O | O | O | 4-NO₂-phenyl | |
| 157 | 3-methylphenyl | CH₃ | O | O | O | 4-CN-phenyl | 97–100 |
| 158 | 4-methylphenyl | CH₃ | O | O | O | 4-Cl-phenyl | |
| 159 | 4-methylphenyl | CH₃ | O | O | O | 4-NO₂-phenyl | |
| 160 | 4-methylphenyl | CH₃ | O | O | O | 4-CN-phenyl | 152–155 |
| 161 | 2-OCH₃-phenyl | CH₃ | O | O | O | 4-Cl-phenyl | |
| 162 | 2-OCH₃-phenyl | CH₃ | O | O | O | 4-NO₂-phenyl | |
| 163 | 2-OCH₃-phenyl | CH₃ | O | O | O | 4-CN-phenyl | 137–140 |
| 164 | 3-OCH₃-phenyl | CH₃ | O | O | O | 4-Cl-phenyl | |
| 165 | 3-OCH₃-phenyl | CH₃ | O | O | O | 4-NO₂-phenyl | |
| 166 | 3-OCH₃-phenyl | CH₃ | O | O | O | 4-CN-phenyl | 134–137 |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 167 | 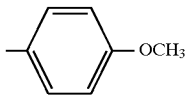 | CH₃ | O | O | O | 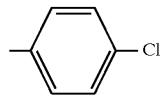 | |
| 168 | 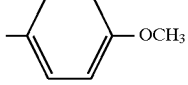 | CH₃ | O | O | O | 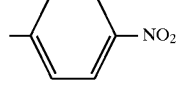 | |
| 169 | 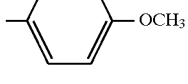 | CH₃ | O | O | O | 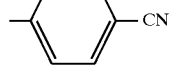 | 139–145 |
| 170 | 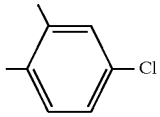 | CH₃ | O | O | O | 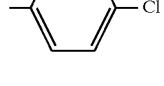 | |
| 171 | 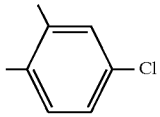 | CH₃ | O | O | O | 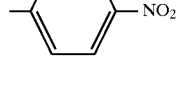 | |
| 172 | 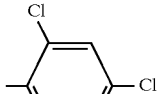 | CH₃ | O | O | O | 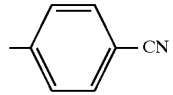 | |
| 173 | 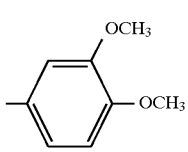 | CH₃ | O | O | O | 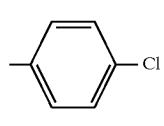 | |
| 174 | 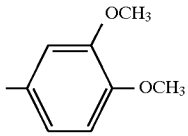 | CH₃ | O | O | O | 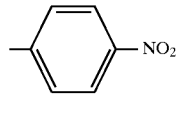 | |
| 175 | 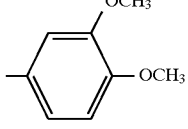 | CH₃ | O | O | O | 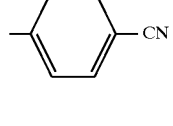 | |
| 176 | 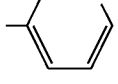 | CH₃ | O | O | O | 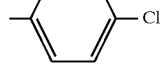 | |
| 177 | 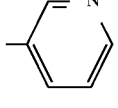 | CH₃ | O | O | O | 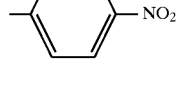 | |
| 178 | 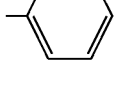 | CH₃ | O | O | O | 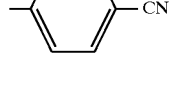 | |

-continued

| Compound No. | R¹ | R⁹ | Z¹ | Z² | Z³ | A | Melting Point (°C.) or Reflactive Index ($n_D^{20}$) |
|---|---|---|---|---|---|---|---|
| 179 | cyclohexenyl | CH₃ | O | O | O | 4-Cl-C₆H₄ | |
| 180 | cyclohexenyl | CH₃ | O | O | O | 4-NO₂-C₆H₄ | |
| 181 | cyclohexenyl | CH₃ | O | O | O | 4-CN-C₆H₄ | |
| 182 | 1-methylcyclopentyl | CH₃ | O | O | O | 4-NO₂-C₆H₄ | |
| 183 | oxiranyl | CH₃ | O | O | O | 4-Cl-C₆H₄ | |
| 184 | CH₂CH₂Cl | CH₃ | O | O | O | 4-CN-C₆H₄ | 170–175 |
| 185 | CH₂Cl | CH₃ | O | O | O | 4-NO₂-C₆H₄ | |
| 186 | CH(Cl)CH₃ | CH₃ | O | O | O | 4-CN-C₆H₄ | |
| 187 | CH₂CF₃ | CH₃ | O | O | O | 4-CN-C₆H₄ | |
| 188 | CH₂—C≡CH | CH₃ | O | O | O | 4-NO₂-C₆H₄ | |
| 189 | CH₂CH₂OCH₃ | CH₃ | O | O | O | 4-Cl-C₆H₄ | |
| 190 | CH₂CH₂OCH₃ | CH₃ | O | O | O | 4-NO₂-C₆H₄ | |
| 191 | CH₂CH₂OCH₃ | CH₃ | O | O | O | 4-CN-C₆H₄ | |
| 192 | —CH₂—C₆H₅ | CH₃ | O | O | O | 4-NO₂-C₆H₄ | |

-continued

| Compound No. | R¹ | R⁰ | Z¹ | Z² | Z³ | A | Melting Point (°C.) or Reflactive Index ($n_D^{20}$) |
|---|---|---|---|---|---|---|---|
| 193 | —CH₂—(phenyl) | CH₃ | O | O | O | —(phenyl)—CN | 125–128 |
| 194 | —CH₂—(phenyl)—CH₃ | CH₃ | O | O | O | —(phenyl)—Cl | |
| 195 | —CH₂—(phenyl)—CH₃ | CH₃ | O | O | O | —(phenyl)—CN | 98–101 |
| 196 | —CH₂—(phenyl)—NO₂ | CH₃ | O | O | O | —(phenyl)—Cl | |
| 197 | C₄H₉-t | CH₃ | O | O | O | —(phenyl)—CH₂Cl | |
| 198 | C₄H₉-t | CH₃ | O | O | O | —(phenyl)—OCHF₂ | |
| 199 | C₃H₇-i | CH₃ | O | O | O | —(phenyl)—CH₂Cl | |
| 200 | C₃H₇-i | CH₃ | O | O | O | —(phenyl)—OCHF₂ | |
| 201 | (phenyl) | CH₃ | O | O | O | —(phenyl)—CH₂Cl | |
| 202 | (phenyl) | CH₃ | O | O | O | —(phenyl)—OCHF₂ | |
| 203 | (phenyl) | CH₃ | S | O | O | —(phenyl)—Cl | 111–113 |
| 204 | (phenyl) | CH₃ | S | O | O | —(phenyl)—NO₂ | 149–152 |
| 205 | (phenyl) | CH₃ | S | O | O | —(phenyl)—CN | 146–149 |
| 206 | (phenyl) | CH₃ | O | S | O | —(phenyl)—Cl | |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 207 | 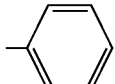 | CH₃ | O | S | O | 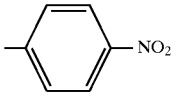 -NO₂ | |
| 208 | 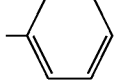 | CH₃ | O | S | O | 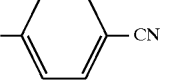 -CN | not determined |
| 209 | 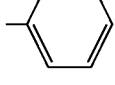 | CH₃ | S | S | O | 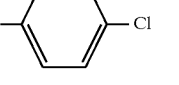 -Cl | |
| 210 | 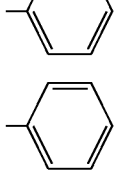 | CH₃ | S | S | O | 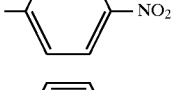 -NO₂ | |
| 211 |  | CH₃ | S | S | O | 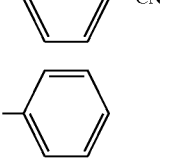 -CN | not determined |
| 212 |  | CH₃ | O | O | S |  | 140–144 |
| 213 |  | CH₃ | O | O | S | 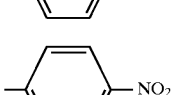 -Cl | 136–140 |
| 214 | 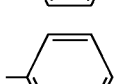 | CH₃ | O | O | S | 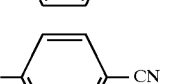 -NO₂ | 123–126 |
| 215 | 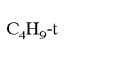 | CH₃ | O | O | S | 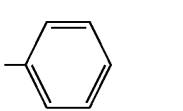 -CN | 144–146 |
| 216 | C₄H₉-t | CH₃ | O | O | S |  | 74–78 |
| 217 | C₄H₉-t | CH₃ | O | O | S | 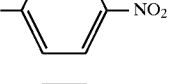 -NO₂ | 109–112 |
| 218 | C₄H₉-t | CH₃ | O | O | S | 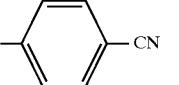 -CN | |
| 219 | C₃H₇-i | CH₃ | O | O | S | 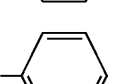 | 122–126 |
| 220 | C₃H₇-i | CH₃ | O | O | S | 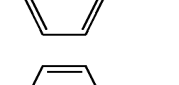 -CN | 165–169 |

-continued
| Compound No. | R¹ | R⁰ | Z¹ | Z² | Z³ | A | Melting Point (°C.) or Reflactive Index ($n_D^{20}$) |
|---|---|---|---|---|---|---|---|
| 221 | $C_3H_7$-i | $CH_3$ | O | O | NH | 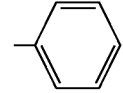 | 158–160 |
| 222 | $C_4H_9$-t | $CH_3$ | O | O | $NCH_3$ | 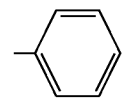 | |
| 223 | 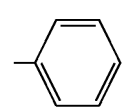 | $CH_3$ | O | O | $NCOOCH_3$ | 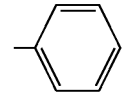 | |
| 224 | 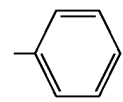 | $CH_3$ | O | O | 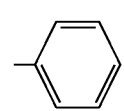 |  | |
| 225 | 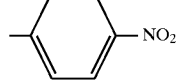 | $CH_3$ | O | O | $NCO_2CH_3$ | 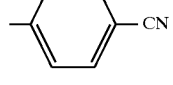 | |
| 226 | $C_4H_9$-t | $C_2H_5$ | O | O | O | 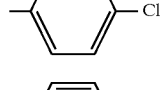 | 101–104 |
| 227 | $C_4H_9$-t | $C_2H_5$ | O | O | O |  | 128–130 |
| 228 | $C_4H_9$-t | $C_2H_5$ | O | O | O | 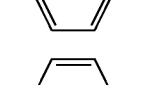 | 100–106 |
| 229 | $C_4H_9$-t | $C_2H_5$ | O | O | O | 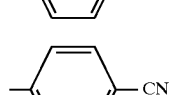 | |
| 230 | 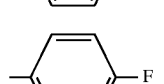 | $C_2H_5$ | O | O | O | 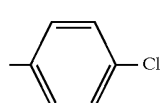 | 149–154 |
| 231 | 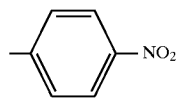 | $C_2H_5$ | O | O | O | 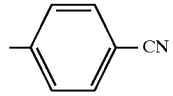 | 152–154 |
| 232 | 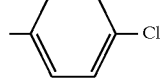 | $C_2H_5$ | O | O | O | 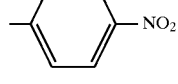 | 108–112 |
| 233 | $C_4H_9$-t | H | O | O | O |  | 1.5081 |
| 234 | $C_4H_9$-t | H | O | O | O |  | |

-continued
| Compound No. | $R^1$ | $R^9$ | $Z^1$ | $Z^2$ | $Z^3$ | A | Melting Point (°C.) or Reflactive Index ($n_D^{20}$) |
|---|---|---|---|---|---|---|---|
| 235 | $C_4H_9$-t | H | O | O | O | 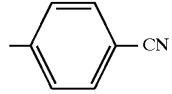 | not determined |
| 236 | 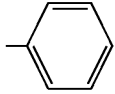 | H | O | O | O |  | 125–130 |
| 237 | 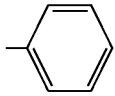 | H | O | O | O | 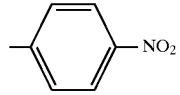 | |
| 238 | 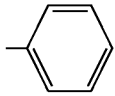 | H | O | O | O | 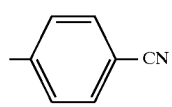 | 43–46 |
| 239 | $C_4H_9$-t | $CH_3$ | O | O | O | 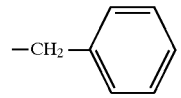 | |
| 240 | $C_4H_9$-t | $CH_3$ | O | O | O | 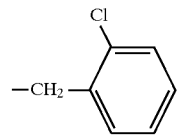 | |
| 241 | $C_4H_9$-t | $CH_3$ | O | O | O | 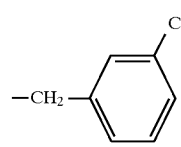 | |
| 242 | $C_4H_9$-t | $CH_3$ | O | O | O | 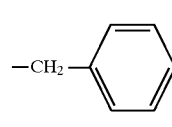 | |
| 243 | $C_4H_9$-t | $CH_3$ | O | O | O | 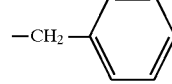 | |
| 244 | $C_4H_9$-t | $CH_3$ | O | O | O | 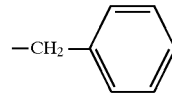 | |
| 245 | $C_4H_9$-t | $CH_3$ | O | O | O | 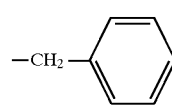 | |
| 246 | $C_3H_7$-i | $CH_3$ | O | O | O | 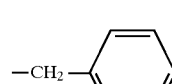 | 104–109 |
| 247 | $C_3H_7$-i | $CH_3$ | O | O | O | 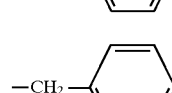 | |

-continued

| Compound No. | R[1] | R[9] | Z[1] | Z[2] | Z[3] | A | Melting Point (°C.) or Refractive Index ($n_D^{20}$) |
|---|---|---|---|---|---|---|---|
| 248 | C₃H₇-i | CH₃ | O | O | O | —CH₂—C₆H₄—CN | |
| 249 | C₆H₅ | CH₃ | O | O | O | —CH₂—C₆H₄—Cl | |
| 250 | C₆H₅ | CH₃ | O | O | O | —CH₂—C₆H₄—NO₂ | |
| 251 | C₆H₅ | CH₃ | O | O | O | —CH₂—C₆H₄—CN | |
| 252 | C₆H₅ | CH₃ | O | O | O | —CH₂—C₆H₃(Cl)₂ (2,4-diCl) | |
| 253 | 4-Cl-C₆H₄ | CH₃ | O | O | O | —CH₂—C₆H₄—NO₂ | |
| 254 | C₃H₇-i | CH₃ | O | O | O | —CH(CH₃)—C₆H₅ | |
| 255 | C₃H₇-i | CH₃ | O | O | O | —CH(CH₃)—C₆H₄—Cl | |
| 256 | C₆H₅ | CH₃ | O | O | O | —CH(CH₃)—C₆H₄—Cl | |
| 257 | C₃H₇-i | CH₃ | O | O | O | —C(CH₃)₂—C₆H₅ | |
| 258 | C₃H₇-i | CH₃ | O | O | O | —C(CH₃)₂—C₆H₄—Cl | |
| 259 | C₆H₅ | CH₃ | O | O | O | —C(CH₃)₂—C₆H₅ | |
| 260 | C₄H₉-t | CH₃ | O | O | NH | —CH(CH₃)—C₆H₅ | |

-continued

| Compound No. | R[1] | R[0] | Z[1] | Z[2] | Z[3] | A | Melting Point (°C.) or Reflactive Index ($n_D^{20}$) |
|---|---|---|---|---|---|---|---|
| 261 | C$_4$H$_9$-t | CH$_3$ | O | O | NH | —C(CH$_3$)$_2$—Ph | |
| 262 | C$_3$H$_7$-i | CH$_3$ | O | O | NH | —CH(CH$_3$)—Ph | |
| 263 | C$_3$H$_7$-i | CH$_3$ | O | O | NH | —C(CH$_3$)$_2$—Ph | |
| 264 | Ph | CH$_3$ | O | O | NH | —CH(CH$_3$)—Ph | |
| 265 | Ph | CH$_3$ | O | O | NH | —C(CH$_3$)$_2$—Ph | |
| 266 | C$_4$H$_9$-t | CH$_3$ | O | O | O | pyridin-3-yl | |
| 267 | C$_4$H$_9$-t | CH$_3$ | O | O | O | 2-chloropyridin-3-yl | |
| 268 | C$_3$H$_7$-i | CH$_3$ | O | O | O | pyridin-3-yl | |
| 269 | C$_3$H$_7$-i | CH$_3$ | O | O | O | 2-chloropyridin-3-yl | |
| 270 | C$_3$H$_7$-i | CH$_3$ | O | O | O | 5-chloropyridin-3-yl | |
| 271 | Ph | CH$_3$ | O | O | O | pyridin-3-yl | |
| 272 | Ph | CH$_3$ | O | O | O | 2-chloropyridin-3-yl | |

5,811,424
-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 273 | 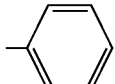 | CH₃ | O | O | O | 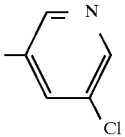 | |
| 274 | 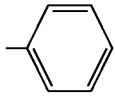 | CH₃ | O | O | O | 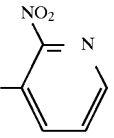 | |
| 275 | 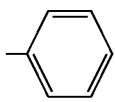 | CH₃ | O | O | O | 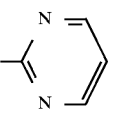 | 60–65 |
| 276 | C₄H₉-t | CH₃ | O | O | O | 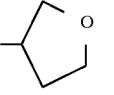 | |
| 277 | C₃H₇-i | CH₃ | O | O | O | 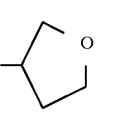 | |
| 278 | 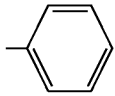 | CH₃ | O | O | O | 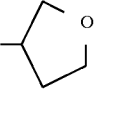 | |
| 279 | C₄H₉-t | CH₃ | O | O | O | 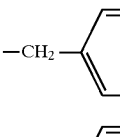 | |
| 280 | C₄H₉-t | CH₃ | O | O | O | 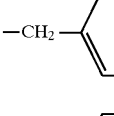 | |
| 281 | C₃H₇-i | CH₃ | O | O | O | 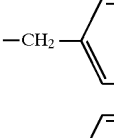 | |
| 282 | C₃H₇-i | CH₃ | O | O | O | 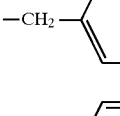 | |
| 283 | 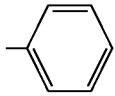 | CH₃ | O | O | O | 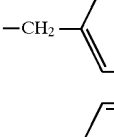 | |
| 284 | 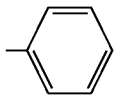 | CH₃ | O | O | O | 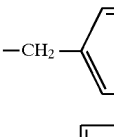 | |
| 285 | C₃H₇-i | CH₃ | O | O | O | 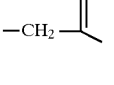 | |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 286 | $C_3H_7$-i | $CH_3$ | O | O | S | $-CH_2-$(furan, O) | |
| 287 | phenyl | $CH_3$ | O | O | O | $-CH_2-$(furan, O) | |
| 288 | phenyl | $CH_3$ | O | O | S | $-CH_2-$(thiophene, S) | |
| 289 | phenyl | $CH_3$ | O | O | NH | $-CH_2-$(furan, O) | |
| 290 | $C_3H_7$-i | $CH_3$ | O | O | NH | $-CH(CN)-$(furan, O) | |
| 291 | $C_3H_7$-i | $CH_3$ | O | O | NH | $-CH(CN)-$(thiophene, S) | |
| 292 | phenyl | $CH_3$ | O | O | NH | $-CH(CN)-$(furan, O) | |
| 293 | phenyl | $CH_3$ | O | O | NH | $-CH(CN)-$(thiophene, S) | |
| 294 | $C_3H_7$-i | $CH_3$ | O | O | O | $-CH_2-$(5-Cl-benzofuran) | |
| 295 | $C_3H_7$-i | $CH_3$ | O | O | O | $-CH(CH_3)-$(5-Cl-benzofuran) | |
| 296 | $C_3H_7$-i | $CH_3$ | O | O | O | $-CH(CN)-$(benzofuran) | |
| 297 | $C_3H_7$-i | $CH_3$ | O | O | NH | $-CH(CN)-$(benzothiophene, S) | |
| 298 | phenyl | $CH_3$ | O | O | O | $-CH_2-$(5-Cl-benzofuran) | |

-continued
| Compound No. | R¹ | R⁹ | Z¹ | Z² | Z³ | A | Melting Point (°C.) or Refractive Index ($n_D^{20}$) |
|---|---|---|---|---|---|---|---|
| 299 | 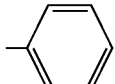 | CH₃ | O | O | O | 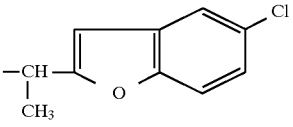 | |
| 300 | 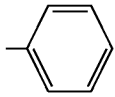 | CH₃ | O | O | O | 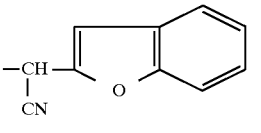 | |
| 301 | 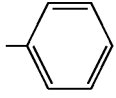 | CH₃ | O | O | NH | 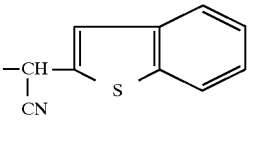 | |
| 302 | 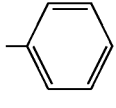 | CH₃ | O | O | NH | 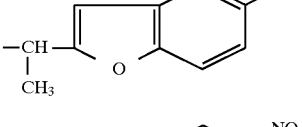 | |
| 303 | 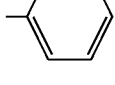 | CH₃ | O | O | NH | 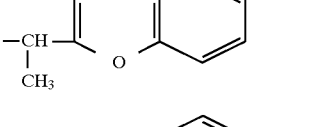 | |
| 304 | C₃H₇-i | CH₃ | O | O | NH | 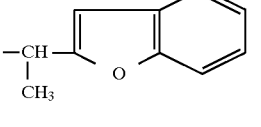 | |
| 305 | C₃H₇-i | CH₃ | O | O | NH | 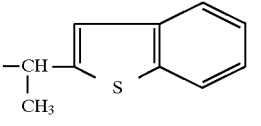 | |
| 306 | C₃H₇-i | CH₃ | O | O | NH | 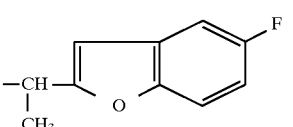 | |
| 307 | C₃H₇-i | CH₃ | O | O | NH | 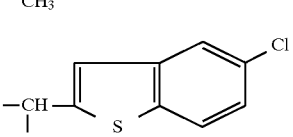 | |
| 308 | C₃H₇-i | CH₃ | O | O | NH | 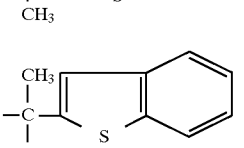 | |
| 309 | C₃H₇-i | CH₃ | O | O | O | 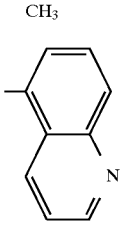 | |

-continued

| Compound No. | R¹ | R⁹ | Z¹ | Z² | Z³ | A | Melting Point (°C.) or Reflactive Index ($n_D^{20}$) |
|---|---|---|---|---|---|---|---|
| 310 | $C_3H_7$-i | $CH_3$ | O | O | O | quinolin-4-yl | |
| 311 | phenyl | $CH_3$ | O | O | $NCH_2OCH_3$ | 4-CN-phenyl | |
| 312 | phenyl | $CH_3$ | O | O | SO | 4-CN-phenyl | |
| 313 | phenyl | $CH_3$ | O | O | $SO_2$ | 4-CN-phenyl | |
| 314 | phenyl | $CH_3$ | O | O | NH | —CH(phenyl)(COOCH₃) | |
| 315 | $C_3H_7$-i | $CH_3$ | O | O | NH | —CH(phenyl)₂ | |
| 316 | $C_3H_7$-i | $CH_3$ | O | O | O | —CH(phenyl)(CH₂-phenyl) | |
| 317 | —CH₂-(4-CN-phenyl) | $CH_3$ | O | O | O | 4-Cl-phenyl | |
| 318 | —CH₂-(4-CN-phenyl) | $CH_3$ | O | O | O | 4-CN-phenyl | |
| 319 | 4-CN-phenyl | $CH_3$ | O | O | O | 4-Cl-phenyl | |
| 320 | 4-CN-phenyl | $CH_3$ | O | O | O | 4-$NO_2$-phenyl | |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 321 | 4-CN-C₆H₄- | CH₃ | O | O | O | 4-CN-C₆H₄- | |
| 322 | 4-CF₃-C₆H₄- | CH₃ | O | O | O | 4-NO₂-C₆H₄- | |
| 323 | 4-CF₃-C₆H₄- | CH₃ | O | O | O | 4-CN-C₆H₄- | 115–117 |
| 324 | 4-OCF₃-C₆H₄- | CH₃ | O | O | O | 4-Cl-C₆H₄- | |
| 325 | 4-OCF₃-C₆H₄- | CH₃ | O | O | O | 4-NO₂-C₆H₄- | |
| 326 | 4-OCF₃-C₆H₄- | CH₃ | O | O | O | 4-CN-C₆H₄- | 127–129 |
| 327 | C₄H₉-t | CH₃ | O | O | O | 4-(S—CH₃)-C₆H₄- | 93–96 |
| 328 | C₄H₉-t | CH₃ | O | O | O | 4-(S(=O)—CH₃)-C₆H₄- | 48–51 |
| 329 | C₄H₉-t | CH₃ | O | O | O | 4-(SO₂—CH₃)-C₆H₄- | 122–125 |
| 330 | C₄H₉-t | CH₃ | O | O | S | 2-F-C₆H₄- | 74–77 |
| 331 | C₄H₉-t | CH₃ | O | O | S | 3-F-C₆H₄- | 1.5164 |
| 332 | C₄H₉-t | CH₃ | O | O | S | 2-OCH₃-C₆H₄- | 1.5319 |
| 333 | C₄H₉-t | CH₃ | O | O | S | 4-OCH₃-C₆H₄- | 1.5361 |

-continued
| Compound No. | R¹ | R⁹ | Z¹ | Z² | Z³ | A | Melting Point (°C.) or Reflective Index ($n_D^{20}$) |
|---|---|---|---|---|---|---|---|
| 334 | $C_4H_9$-t | $CH_3$ | O | O | NH | 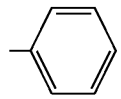 | 102–104 |
| 335 | $C_4H_9$-t | $CH_3$ | O | O | S | 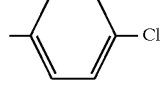 4-Cl | 80–84 |
| 336 | $C_4H_9$-t | $CH_3$ | O | O | S | 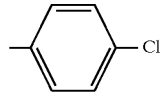 4-Cl | 133–137 |
| 337 | $C_4H_9$-t | $CH_3$ | O | O | S | 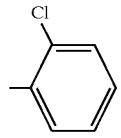 2-Cl | 1.5360 |
| 338 | $C_4H_9$-t | $CH_3$ | O | O | S | 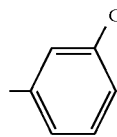 3-Cl | 1.5361 |
| 339 | $C_4H_9$-t | $CH_3$ | O | O | S | 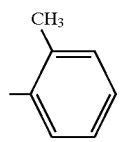 2-$CH_3$ | 1.5274 |
| 340 | $C_4H_9$-t | $CH_3$ | O | O | S | 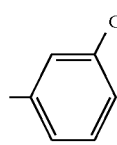 3-$CH_3$ | 1.5245 |
| 341 | $C_4H_9$-t | $CH_3$ | O | O | S | 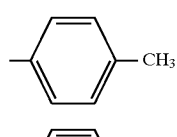 4-$CH_3$ | 1.5269 |
| 342 | $C_4H_9$-t | $CH_3$ | O | O | S | 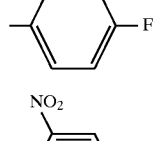 4-F | 66–69 |
| 343 | $C_4H_9$-t | $CH_3$ | O | O | O | 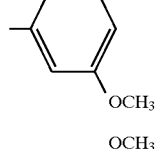 3-$NO_2$, 4-$OCH_3$ | 71–74 |
| 344 | $C_4H_9$-t | $CH_3$ | O | O | S | 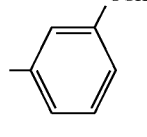 3-$OCH_3$ | 1.5312 |
| 345 | $C_3H_7$-i | $CH_3$ | O | O | O | 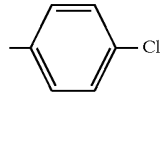 4-Cl | 161–163 |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 346 | $C_3H_7$-i | $CH_3$ | O | O | O |  | 167–171 |
| 347 | $C_3H_7$-i | $CH_3$ | O | O | O | 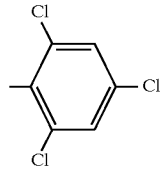 | 166–172 |
| 348 | $C_3H_7$-i | $CH_3$ | O | O | S | 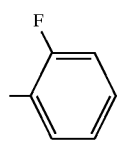 | 121–123 |
| 349 | $C_3H_7$-i | $CH_3$ | O | O | S | 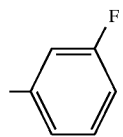 | 125–129 |
| 350 | $C_3H_7$-i | $CH_3$ | O | O | S | 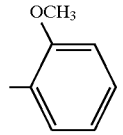 | 103–106 |
| 351 | $C_3H_7$-i | $CH_3$ | O | O | S | 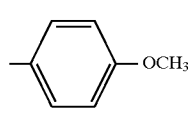 | 122–125 |
| 352 | $C_3H_7$-i | $CH_3$ | O | O | S | 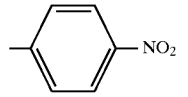 | 155–158 |
| 353 | $C_3H_7$-i | $CH_3$ | O | O | NH | 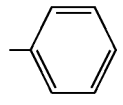 | 130–134 |
| 354 | $C_3H_7$-i | $CH_3$ | O | O | SO |  | 119–123 |
| 355 | $C_3H_7$-i | $CH_3$ | O | O | $SO_2$ |  | 151–153 |
| 356 | $C_3H_7$-i | $CH_3$ | O | O | O | 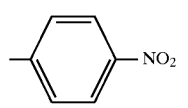 | 177–180 |
| 357 | $C_3H_7$-i | $CH_3$ | O | O | S | 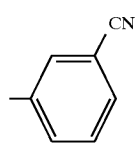 | 137–140 |

-continued
| Compound No. | R¹ | R⁹ | Z¹ | Z² | Z³ | A | Melting Point (°C.) or Reflective Index ($n_D^{20}$) |
|---|---|---|---|---|---|---|---|
| 358 | $C_3H_7$-i | $CH_3$ | O | O | $NCH_3$ | 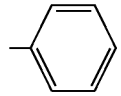 | 145–148 |
| 359 | $C_3H_7$-i | $CH_3$ | O | O | NH | 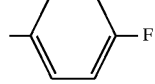 | 155–156 |
| 360 | $C_3H_7$-i | $CH_3$ | O | O | $NCH_3$ | 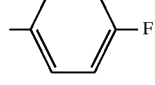 | 141–143 |
| 361 | $C_3H_7$-i | $CH_3$ | O | O | NH | 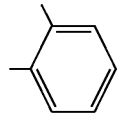 | 85–90 |
| 362 | $C_3H_7$-i | $CH_3$ | O | O | NH | 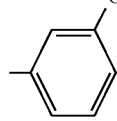 | 143–145 |
| 363 | $C_3H_7$-i | $CH_3$ | O | O | $NCH_3$ |  | 65–67 |
| 364 | $C_3H_7$-i | $CH_3$ | O | O | NH |  | 146–149 |
| 365 | $C_3H_7$-i | $CH_3$ | O | O | S | 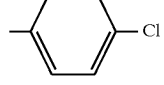 | 115–118 |
| 366 | $C_3H_7$-i | $CH_3$ | O | O | S | 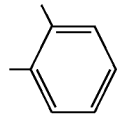 | 124–127 |
| 367 | $C_3H_7$-i | $CH_3$ | O | O | S | 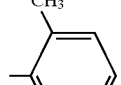 | 119–121 |
| 368 | $C_3H_7$-i | $CH_3$ | O | O | S | 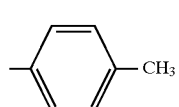 | 107–110 |
| 369 | $C_3H_7$-i | $CH_3$ | O | O | S | 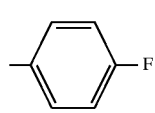 | 111–115 |

-continued
| Compound No. | R¹ | R⁹ | Z¹ | Z² | Z³ | A | Melting Point (°C.) or Reflactive Index ($n_D^{20}$) |
|---|---|---|---|---|---|---|---|
| 370 | $C_3H_7$-i | $CH_3$ | O | O | S | 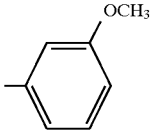 | 109–112 |
| 371 | $C_4H_9$-i | $CH_3$ | O | O | O | 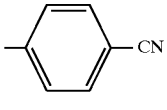 | 125–130 |
| 372 | $C_5H_{11}$ | $CH_3$ | O | O | O | 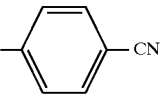 | 109–111 |
| 373 | $C_6H_{13}$ | $CH_3$ | O | O | O | 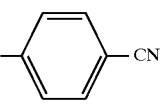 | 107–110 |
| 374 | —CH—$C_3H_7$<br>   \|<br>  $CH_3$ | $CH_3$ | O | O | O | 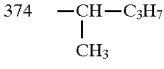 | 122–125 |
| 375 | $C_3H_7$-i | $CH_3$ | O | O | $NCOCH_3$ | 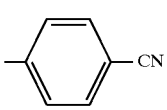 | 56–60 |
| 376 | 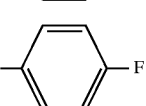 | $CH_3$ | O | O | O | 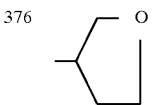 | 181–184 |
| 377 | 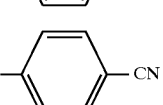 | $CH_3$ | O | O | O | 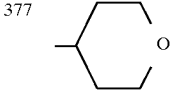 | 201–204 |
| 378 | 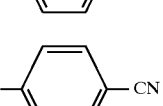 | $CH_3$ | O | O | O | 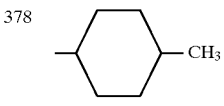 | 111–116 |
| 379 | 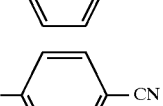 | $CH_3$ | O | O | O | 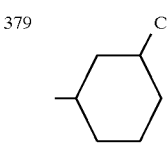 | 141–142 |
| 380 | 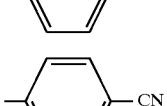 | $CH_3$ | O | O | O | 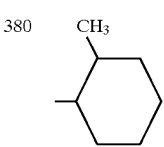 | 133–136 |
| 381 | $CH_2$—C≡CH | $CH_3$ | O | O | O | 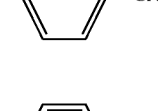 | 148–151 |
| 382 | 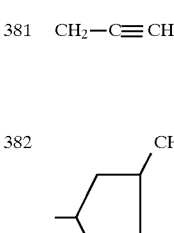 | $CH_3$ | O | O | O | 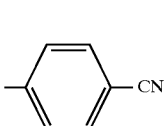 | 161–164 |

-continued

| Compound No. | R¹ | R⁹ | Z¹ | Z² | Z³ | A | Melting Point (°C.) or Refractive Index ($n_D^{20}$) |
|---|---|---|---|---|---|---|---|
| 383 | —CH(CH₃)—CH₂OCH₃ | CH₃ | O | O | O | 4-CN-phenyl | 102–107 |
| 384 | phenyl | CH₃ | O | O | O | 2,4,6-trichlorophenyl | 159–162 |
| 385 | phenyl | CH₃ | O | O | NH | phenyl | 130–134 |
| 386 | phenyl | CH₃ | O | O | S | 4-F-phenyl | 127–130 |
| 387 | phenyl | CH₃ | O | O | S | 3-CN-phenyl | 108–110 |
| 388 | phenyl | CH₃ | O | O | NH | 4-Cl-phenyl | 154–156 |
| 389 | phenyl | CH₃ | O | O | NCH₃ | phenyl | 125–130 |
| 390 | phenyl | CH₃ | O | O | NH | 4-F-phenyl | 147–149 |
| 391 | phenyl | CH₃ | O | O | NCH₃ | 4-F-phenyl | 64–70 |
| 392 | phenyl | CH₃ | O | O | NH | 3-Cl-phenyl | 117–119 |
| 393 | phenyl | CH₃ | O | O | NH | 4-Br-phenyl | 156–160 |
| 394 | 4-Br-phenyl | CH₃ | O | O | O | 4-CN-phenyl | 156–162 |
| 395 | 4-Cl-phenyl | CH₃ | O | O | O | 4-CN-phenyl | 137–140 |

-continued

| Compound No. | R¹ | R⁹ | Z¹ | Z² | Z³ | A | Melting Point (°C.) or Reflactive Index ($n_D^{20}$) |
|---|---|---|---|---|---|---|---|
| 396 | 4-Cl-C₆H₄- | CH₃ | O | O | O | 4-CN-C₆H₄- | 174–179 |
| 397 | 4-F-C₆H₄- | CH₃ | O | O | O | 4-CN-C₆H₄- | 153–156 |
| 398 | 4-NO₂-C₆H₄- | CH₃ | O | O | O | 4-CN-C₆H₄- | 130–134 |
| 399 | 4-F-C₆H₄- | CH₃ | O | O | O | 4-NO₂-C₆H₄- | 156–161 |
| 400 | 2-NO₂-C₆H₄- | CH₃ | O | O | O | 4-CN-C₆H₄- | 125–129 |
| 401 | 4-F-C₆H₄- | CH₃ | O | O | O | 4-CN-C₆H₄- | 155–158 |
| 402 | 2,4-(CH₃)₂-C₆H₃- | CH₃ | O | O | O | 4-CN-C₆H₄- | 141–144 |
| 403 | 3,4-(CH₃)₂-C₆H₃- | CH₃ | O | O | O | 4-CN-C₆H₄- | 153–154 |
| 404 | 2,4-F₂-C₆H₃- | CH₃ | O | O | O | 4-CN-C₆H₄- | 144–148 |
| 405 | 3,4-F₂-C₆H₃- | CH₃ | O | O | O | 4-CN-C₆H₄- | 129–133 |
| 406 | C₆H₅- | CH₃ | O | O | NH | 2-Cl-C₆H₄- | 60–62 |
| 407 | C₄H₉-t | CH₃ | O | O | O | 5-Cl-pyridin-2-yl | 90–93 |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 408 | 2-methyl-4-chlorophenyl (CH₃, Cl) | CH₃ | O | O | O | 4-cyanophenyl | 129–130 |
| 409 | C₄H₉-t | CH₃ | O | O | O | pyridyl | 111–112 |
| 410 | C₄H₉-t | CH₃ | O | O | O | pyridyl | 129–131 |
| 411 | 2,4,6-trimethylphenyl | CH₃ | O | O | O | 4-cyanophenyl | 163–164 |
| 412 | C₃H₇-i | CH₃ | O | O | O | 3-chloropyridyl | 118–120 |
| 413 | phenyl | CH₃ | O | O | O | 3-chloropyridyl | 123–124 |
| 414 | C₄H₉-t | C₂H₅ | O | O | O | 4-cyanophenyl | 122–125 |
| 415 | C₄H₉-t | C₂H₅ | O | O | O | 4-cyanophenyl | 135–137 |
| 416 | C₃H₇-i | C₂H₅ | O | O | S | 4-fluorophenyl | 85–86 |
| 417 | C₃H₇-i | C₂H₅ | O | O | O | 4-cyanophenyl | 145–148 |
| 418 | —CH₂-phenyl | C₂H₅ | O | O | O | 4-cyanophenyl | 139–141 |
| 419 | phenyl | C₂H₅ | O | O | S | 4-cyanophenyl | 105–107 |
| 420 | phenyl | C₂H₅ | O | O | S | 4-fluorophenyl | 130–133 |

-continued

| Compound No. | R¹ | R⁰ | Z¹ | Z² | Z³ | A | Melting Point (°C.) or Reflective Index ($n_D^{20}$) |
|---|---|---|---|---|---|---|---|
| 421 | 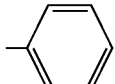 | $C_2H_5$ | O | O | NH |  (4-F-phenyl) | 137–139 |
| 422 | 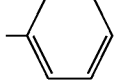 | $C_2H_5$ | O | O | $NCH_3$ | 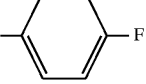 (4-F-phenyl) | 53–56 |
| 423 | 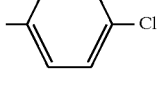 (4-Cl-phenyl) | $C_2H_5$ | O | O | O | 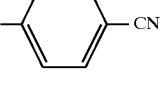 (4-CN-phenyl) | 159–163 |
| 424 | 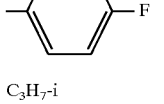 (4-F-phenyl) | $C_2H_5$ | O | O | O | 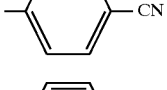 (4-CN-phenyl) | 150–153 |
| 425 | $C_3H_7$-i | H | O | O | O | 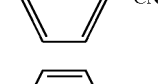 (4-CN-phenyl) | 118–121 |
| 426 | $-CH_2$-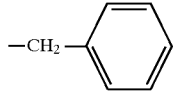 | H | O | O | O | 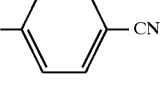 (4-CN-phenyl) | 127–132 |
| 427 | 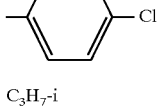 (4-Cl-phenyl) | H | O | O | O | 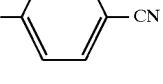 (4-CN-phenyl) | 141–145 |
| 428 | $C_3H_7$-i | $CH_3$ | O | O | O | 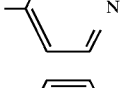 (4-pyridyl) | 217–220 |
| 429 | 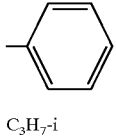 | $CH_3$ | O | O | O | 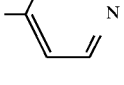 (4-pyridyl) | 65–68 |
| 430 | $C_3H_7$-i | $CH_3$ | S | O | O | 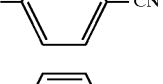 (4-CN-phenyl) | 161–163 |
| 431 | $C_2H_5$ | $CH_3$ | S | O | O | 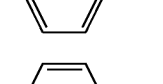 (4-CN-phenyl) | 152–154 |
| 432 | $C_2H_5$ | $CH_3$ | S | O | O |  (4-$NO_2$-phenyl) | 164–166 |
| 433 | 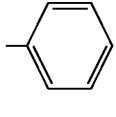 | $CH_3$ | O | O | O | 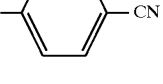 (4-CN-phenyl) | 118–120 |
| 434 | 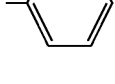 | $CH_3$ | O | O | $NCOCH_3$ | 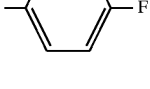 (4-F-phenyl) | |

-continued

| Compound No. | R¹ | R⁹ | Z¹ | Z² | Z³ | A | Melting Point (°C.) or Reflective Index ($n_D^{20}$) |
|---|---|---|---|---|---|---|---|
| 435 | $C_3H_7$-i | $CH_3$ | O | O | $NCO_2CH_3$ | 4-Cl-phenyl | |
| 436 | $C_3H_7$-i | $CH_3$ | O | O | N(CO-phenyl) | 4-Cl-phenyl | 71–73 |
| 437 | $C_3H_7$-i | $CH_3$ | O | O | $NCH_2OCH_3$ | 4-Cl-phenyl | |
| 438 | 2,4,6-trichlorophenyl | $CH_3$ | O | O | O | 4-CN-phenyl | |
| 439 | 2-CH₃-4-Cl-phenyl | $CH_3$ | O | O | O | 4-CN-phenyl | 135–138 |
| 440 | $-CH_2CH_2$-phenyl | $CH_3$ | O | O | O | 4-CN-phenyl | 112–114 |
| 441 | $C_3H_7$-i | $CH_3$ | O | O | NH | 4-CN-phenyl | |

TABLE 2

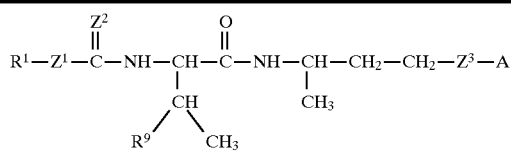

$$R^1-Z^1-\overset{Z^2}{\overset{\|}{C}}-NH-\underset{\underset{R^9}{|}}{\overset{|}{CH}}\underset{CH_3}-\overset{O}{\overset{\|}{C}}-NH-\underset{\underset{CH_3}{|}}{CH}-CH_2-CH_2-Z^3-A$$

| Compound No. | R¹ | R⁹ | Z¹ | Z² | Z³ | A | Melting Point (°C.) or Reflactive Index ($n_D^{20}$) |
|---|---|---|---|---|---|---|---|
| 442 | phenyl | $CH_3$ | O | O | O | 4-Cl-phenyl | |
| 443 | $C_4H_9$-t | $CH_3$ | O | O | O | 4-Cl-phenyl | |
| 444 | $C_3H_7$-i | $CH_3$ | O | O | O | 4-Cl-phenyl | |

TABLE 2-continued $$R^1-Z^1-\overset{Z^2}{\underset{\|}{C}}-NH-\underset{\underset{R^9}{\overset{|}{CH}}\diagdown CH_3}{\overset{|}{CH}}-\overset{O}{\underset{\|}{C}}-NH-\underset{\underset{CH_3}{\overset{|}{CH}}}{\overset{|}{CH}}-CH_2-CH_2-Z^3-A$$

| Compound No. | R¹ | R⁹ | Z¹ | Z² | Z³ | A | Melting Point (°C.) or Refractive Index ($n_D^{20}$) |
|---|---|---|---|---|---|---|---|
| 445 | —CH₂—⟨C₆H₄⟩—CH₃ | CH₃ | O | O | O | ⟨C₆H₃⟩(OCH₃)(OCH₃) | |
| 446 | —CH₂—⟨C₆H₅⟩ | CH₃ | O | O | O | ⟨C₆H₃⟩(OCH₃)(OCH₃) | |
| 447 | C₃H₇-i | CH₃ | O | O | O | ⟨C₆H₃⟩(OCH₃)(OCH₃) | |
| 448 | ⟨C₆H₅⟩ | CH₃ | O | O | O | ⟨C₆H₄⟩—CN | |
| 449 | C₄H₉-t | CH₃ | O | O | O | ⟨C₆H₄⟩—CN | |
| 450 | C₃H₇-i | CH₃ | O | O | O | ⟨C₆H₄⟩—CN | |

TABLE 3

$$R^1-O-\overset{O}{\underset{\|}{C}}-NH-\underset{\underset{R^2}{|}}{\overset{|}{CH}}-\overset{O}{\underset{\|}{C}}-NH-\underset{\underset{CH_3}{|}}{\overset{|}{CH}}-CH_2-O-Q$$

| Compound No. | R¹ | R² | Q | Melting Point (°C.) or Refractive Index ($n_D^{20}$) |
|---|---|---|---|---|
| 451 | ⟨C₆H₄⟩—OCHF₂ | C₃H₇ | ⟨C₆H₄⟩—CN | 117–119 |
| 452 | C₄H₉-t | C₃H₇ | ⟨C₆H₄⟩—CN | 78–80 |
| 453 | C₄H₉-t | C₃H₇ | ⟨C₆H₄⟩—CN | 105–107 |

TABLE 3-continued $$R^1-O-\overset{O}{\overset{\|}{C}}-NH-\underset{\underset{R^2}{|}}{CH}-\overset{O}{\overset{\|}{C}}-NH-\underset{\underset{CH_3}{|}}{CH}-CH_2-O-Q$$

| Compound No. | R$^1$ | R$^2$ | Q | Melting Point (°C.) or Refractive Index (n$_D^{20}$) |
|---|---|---|---|---|
| 454 | C$_4$H$_9$-t | C$_3$H$_7$ | 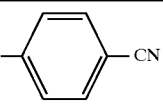 | 93–95 |
| 455 | C$_4$H$_9$-t | C$_4$H$_9$-i | 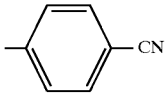 | not determined |
| 456 | C$_4$H$_9$-t | 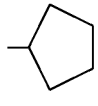 | 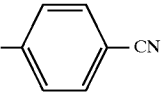 | 140–142 |
| 457 | C$_4$H$_9$-t | C$_4$H$_9$-t | 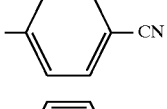 | 68–71 |
| 458 | C$_4$H$_9$-t | 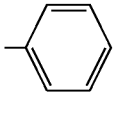 | 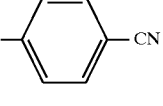 | 61–64 |
| 459 | C$_4$H$_9$-t | 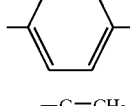 | 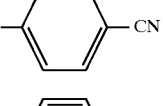 | 124–126 |
| 460 | C$_4$H$_9$-t | $-\underset{\underset{CH_3}{\|}}{C}=CH_2$ | 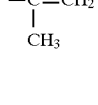 | 1.5132 |
| 461 | C$_4$H$_9$-t | $-\underset{\underset{CH_3}{\|}}{C}=CH_2$ | 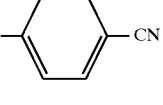 | 107–109 |
| 462 | C$_3$H$_7$-i | 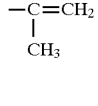 | 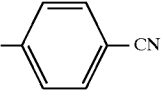 | 155–158 |
| 463 | C$_3$H$_7$-i | 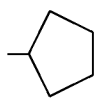 | 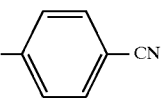 | 149–151 |
| 464 | C$_3$H$_7$-i | 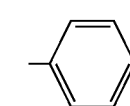 | 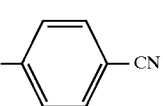 | 158–161 |
| 465 | 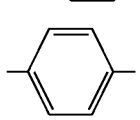 | C$_3$H$_7$ | 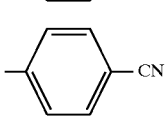 | 88–91 |
| 466 | 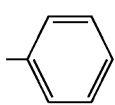 | C$_4$H$_9$-i | 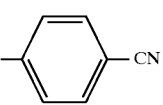 | 43–47 |

TABLE 3-continued
$$R^1-O-\overset{O}{\underset{\parallel}{C}}-NH-\underset{\underset{R^2}{|}}{CH}-\overset{O}{\underset{\parallel}{C}}-NH-\underset{\underset{CH_3}{|}}{CH}-CH_2-O-Q$$
| Compound No. | R¹ | R² | Q | Melting Point (°C.) or Reflactive Index ($n_D^{20}$) |
|---|---|---|---|---|
| 467 | 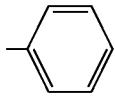 |  | 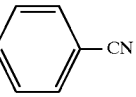 | 153–156 |
| 468 | 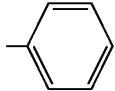 | C₄H₉-t | 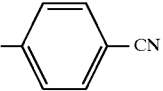 | 75–78 |
| 469 | 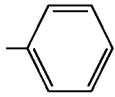 | 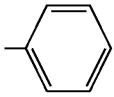 | 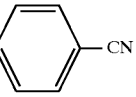 | 68–71 |
| 470 | 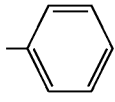 |  | 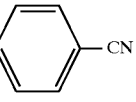 | 152–155 |
| 471 |  |  | 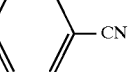 | 141–145 |
| 472 | 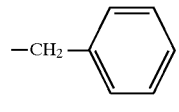 | 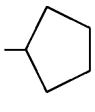 | 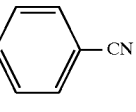 | 170–174 |
| 473 | 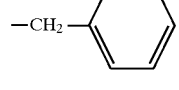 | C₄H₉-t | 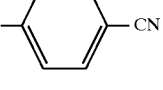 | 46–49 |
| 474 | 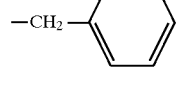 | 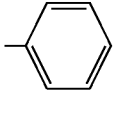 | 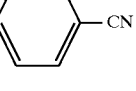 | 155–157 |
| 475 | 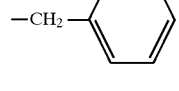 | 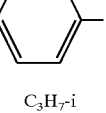 | 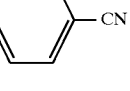 | 128–129 |
| 476 | 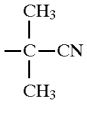 | C₃H₇-i | 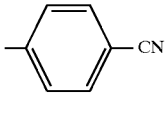 | 127–129 |
| 477 | 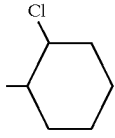 | C₃H₇-i | 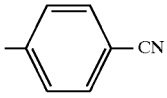 | 152–154 |
| 478 | C₄H₉-t | C₃H₇-i | 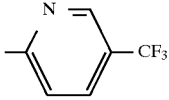 | 100–103 |

TABLE 3-continued $$R^1-O-\overset{O}{\underset{\|}{C}}-NH-\underset{R^2}{\underset{|}{CH}}-\overset{O}{\underset{\|}{C}}-NH-\underset{CH_3}{\underset{|}{CH}}-CH_2-O-Q$$

| Compound No. | R¹ | R² | Q | Melting Point (°C.) or Reflactive Index ($n_D^{20}$) |
|---|---|---|---|---|
| 479 | $C_4H_9$-t | $C_3H_7$-i | 5-chloro-2-methyl-4-(trifluoromethyl)pyridin-3-yl | 105–106 |
| 480 | $C_4H_9$-t | $C_3H_7$-i | 5-chloro-6-ethyl-2-methylpyrimidin-4-yl | 109–112 |
| 481 | $C_3H_7$-i | $C_3H_7$-i | 5-chloro-6-ethyl-2-methylpyrimidin-4-yl | 173–175 |
| 482 | $-CH_2-$cyclohexyl | $C_3H_7$-i | 4-cyanophenyl | 128–129 |

TABLE 4

$$R^1-O-\overset{O}{\underset{\|}{C}}-NH-\underset{R^2}{\underset{|}{CH}}-\overset{O}{\underset{\|}{C}}-NH-\underset{R^4}{\underset{|}{CH}}-Z^3-A$$

| Compound No. | R¹ | R² | R⁴ | Z³ | A | Melting Point (°C.) or Reflactive Index ($n_D^{20}$) |
|---|---|---|---|---|---|---|
| 483 | $C_4H_9$-t | $C_3H_7$-i | $CH_3$ | $-\overset{O}{\underset{\|}{C}}-\underset{H}{\underset{\|}{N}}-$ | 4-chlorophenyl | 82–87 |
| 484 | $C_4H_9$-t | $C_3H_7$-i | $CH_3$ | $-\overset{O}{\underset{\|}{C}}-\underset{H}{\underset{\|}{N}}-$ | 4-methoxyphenyl | 156–159 |
| 485 | $C_4H_9$-t | $C_3H_7$-i | $CH_3$ | $-\overset{O}{\underset{\|}{C}}-\underset{H}{\underset{\|}{N}}-$ | 4-methylphenyl | 145–149 |
| 486 | $C_4H_9$-t | $C_3H_7$-i | $CH_3$ | $-\overset{O}{\underset{\|}{C}}-\underset{H}{\underset{\|}{N}}-$ | 4-cyanophenyl | 96–100 |
| 487 | $C_4H_9$-t | $C_3H_7$-i | $CH_3$ | $-\overset{O}{\underset{\|}{C}}-\underset{H}{\underset{\|}{N}}-$ | phenyl | 157–158 |

TABLE 4-continued $$R^1-O-\overset{\overset{O}{\|}}{C}-NH-\underset{\underset{R^2}{|}}{CH}-\overset{\overset{O}{\|}}{C}-NH-\underset{\underset{R^4}{|}}{CH}-Z^3-A$$

| Compound No. | $R^1$ | $R^2$ | $R^4$ | $Z^3$ | A | Melting Point (°C.) or Reflactive Index ($n_D^{20}$) |
|---|---|---|---|---|---|---|
| 488 | $C_4H_9$-t | $C_3H_7$-i | $CH_3$ | $\overset{\overset{O}{\|}}{C}-\overset{\overset{H}{\|}}{N}$ | 3-Cl-C₆H₄ | 83–86 |
| 489 | $C_4H_9$-t | $C_3H_7$-i | $CH_3$ | $\overset{\overset{O}{\|}}{C}-\overset{\overset{H}{\|}}{N}$ | —CH₂—(4-Cl-C₆H₄) | 144–146 |
| 490 | $C_4H_9$-t | $C_3H_7$-i | $CH_3$ | $\overset{\overset{O}{\|}}{C}-\overset{\overset{CH_3}{\|}}{N}$ | 4-Cl-C₆H₄ | 70–73 |
| 491 | $C_4H_9$-t | $C_3H_7$-i | $CH_3$ | $\overset{\overset{O}{\|}}{C}-\overset{\overset{H}{\|}}{N}$ | 2-Cl-C₆H₄ | 140–143 |
| 492 | $C_3H_7$-i | $C_3H_7$-i | $CH_3$ | $\overset{\overset{O}{\|}}{C}-\overset{\overset{H}{\|}}{N}$ | 4-Cl-C₆H₄ | 179–182 |
| 493 | $C_3H_7$-i | $C_3H_7$-i | $CH_3$ | $\overset{\overset{O}{\|}}{C}-\overset{\overset{H}{\|}}{N}$ | 4-OCH₃-C₆H₄ | 251–255 |
| 494 | $C_3H_7$-i | $C_3H_7$-i | $CH_3$ | $\overset{\overset{O}{\|}}{C}-\overset{\overset{H}{\|}}{N}$ | 4-CH₃-C₆H₄ | 219–222 |
| 495 | $C_3H_7$-i | $C_3H_7$-i | $CH_3$ | $\overset{\overset{O}{\|}}{C}-\overset{\overset{H}{\|}}{N}$ | 4-CN-C₆H₄ | 88–92 |
| 496 | $C_3H_7$-i | $C_3H_7$-i | $CH_3$ | $\overset{\overset{O}{\|}}{C}-\overset{\overset{H}{\|}}{N}$ | C₆H₅ | 211–212 |
| 497 | $C_3H_7$-i | $C_3H_7$-i | $CH_3$ | $\overset{\overset{O}{\|}}{C}-\overset{\overset{H}{\|}}{N}$ | 3-Cl-C₆H₄ | 210–213 |
| 498 | $C_3H_7$-i | $C_3H_7$-i | $CH_3$ | $\overset{\overset{O}{\|}}{C}-\overset{\overset{H}{\|}}{N}$ | —CH₂—(4-Cl-C₆H₄) | 200–203 |
| 499 | $C_3H_7$-i | $C_3H_7$-i | $CH_3$ | $\overset{\overset{O}{\|}}{C}-\overset{\overset{CH_3}{\|}}{N}$ | 4-Cl-C₆H₄ | 68–72 |

TABLE 4-continued $$R^1-O-\overset{O}{\underset{||}{C}}-NH-\underset{\underset{R^2}{|}}{CH}-\overset{O}{\underset{||}{C}}-NH-\underset{\underset{R^4}{|}}{CH}-Z^3-A$$

| Compound No. | $R^1$ | $R^2$ | $R^4$ | $Z^3$ | A | Melting Point (°C.) or Reflactive Index ($n_D^{20}$) |
|---|---|---|---|---|---|---|
| 500 | $C_3H_7$-i | $C_3H_7$-i | $CH_3$ | $\overset{O}{\underset{||}{C}}-\overset{H}{\underset{|}{N}}$ | 2-Cl-C₆H₄ | 205–210 |
| 501 | $C_3H_7$-i | $C_3H_7$-i | $CH_3$ | $\overset{O}{\underset{||}{C}}-\overset{H}{\underset{|}{N}}$ | 3-CN-C₆H₄ | 113–115 |
| 502 | $C_3H_7$-i | $C_3H_7$-i | $CH_3$ | $\overset{O}{\underset{||}{C}}-\overset{H}{\underset{|}{N}}$ | 4-CN-C₆H₄ | 184–186 |
| 503 | $C_3H_7$-i | $C_3H_7$-i | $CH_3$ | $\overset{O}{\underset{||}{C}}-\overset{H}{\underset{|}{N}}$ | 4-CN-C₆H₄ | 73–75 |
| 504 | $C_3H_7$-i | $C_3H_7$-i | $CH_3$ | COO | 4-Cl-C₆H₄ | 184–185 |
| 505 | $C_3H_7$-i | $C_3H_7$-i | $CH_3$ | COO | C₆H₅ | 151–153 |
| 506 | $C_3H_7$-i | $C_4H_9$-s | $CH_3$ | $\overset{O}{\underset{||}{C}}-\overset{H}{\underset{|}{N}}$ | 4-CN-C₆H₄ | 197–198 |
| 507 | $C_3H_7$-i | $C_2H_5$ | $CH_3$ | $\overset{O}{\underset{||}{C}}-\overset{H}{\underset{|}{N}}$ | 4-CN-C₆H₄ | 84–87 |
| 508 | $C_4H_9$-s | $C_3H_7$-i | $CH_3$ | $\overset{O}{\underset{||}{C}}-\overset{H}{\underset{|}{N}}$ | 4-CN-C₆H₄ | 165–167 |
| 509 | cyclopentyl | $C_3H_7$-i | $CH_3$ | $\overset{O}{\underset{||}{C}}-\overset{H}{\underset{|}{N}}$ | 4-CN-C₆H₄ | 197–199 |
| 510 | C₆H₅ | $C_3H_7$-i | $CH_3$ | $\overset{O}{\underset{||}{C}}-\overset{H}{\underset{|}{N}}$ | 4-Cl-C₆H₄ | 201–204 |
| 511 | C₆H₅ | $C_3H_7$-i | $CH_3$ | $\overset{O}{\underset{||}{C}}-\overset{H}{\underset{|}{N}}$ | 4-OCH₃-C₆H₄ | 219–221 |

TABLE 4-continued $$R^1-O-\overset{\overset{O}{\|}}{C}-NH-\overset{\overset{}{\underset{R^2}{|}}}{CH}-\overset{\overset{O}{\|}}{C}-NH-\overset{\overset{}{\underset{R^4}{|}}}{CH}-Z^3-A$$

| Compound No. | R¹ | R² | R⁴ | Z³ | A | Melting Point (°C.) or Refractive Index ($n_D^{20}$) |
|---|---|---|---|---|---|---|
| 512 |  | $C_3H_7$-i | $CH_3$ | $\overset{O}{\underset{C-N}{\|}}\overset{H}{\underset{}{|}}$ | 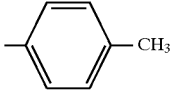—$CH_3$ | 245–250 |
| 513 |  | $C_3H_7$-i | $CH_3$ | $\overset{O}{\underset{C-N}{\|}}\overset{H}{\underset{}{|}}$ | 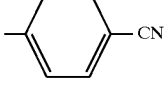—CN | 225–230 |
| 514 |  | $C_3H_7$-i | $CH_3$ | $\overset{O}{\underset{C-N}{\|}}\overset{H}{\underset{}{|}}$ | 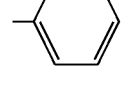 | 199–202 |
| 515 |  | $C_3H_7$-i | $CH_3$ | $\overset{O}{\underset{C-N}{\|}}\overset{H}{\underset{}{|}}$ | 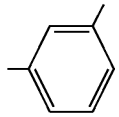 | 194–197 |
| 516 |  | $C_3H_7$-i | $CH_3$ | $\overset{O}{\underset{C-N}{\|}}\overset{H}{\underset{}{|}}$ | —$CH_2$——Cl | 173–175 |
| 517 | 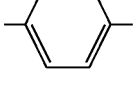 | $C_3H_7$-i | $CH_3$ | $\overset{O}{\underset{C-N}{\|}}\overset{CH_3}{\underset{}{|}}$ | —Cl | 69–71 |
| 518 | 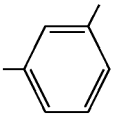 | $C_3H_7$-i | $CH_3$ | $\overset{O}{\underset{C-N}{\|}}\overset{H}{\underset{}{|}}$ |  | 149–153 |
| 519 | 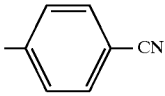 | $C_3H_7$-i | $CH_3$ | $\overset{O}{\underset{C-N}{\|}}\overset{H}{\underset{}{|}}$ | —CN | 158–161 |
| 520 | 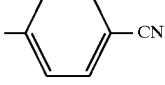 | $C_3H_7$-i | $CH_3$ | $\overset{O}{\underset{C-N}{\|}}\overset{H}{\underset{}{|}}$ | —CN | 202–203 |
| 521 | 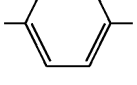 | $C_3H_7$-i | $CH_3$ | COO | —Cl | 168–170 |
| 522 | 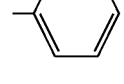 | $C_3H_7$-i | $CH_3$ | COO |  | 175–178 |
| 523 | 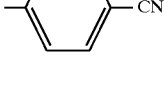 | $C_4H_9$-s | $CH_3$ | $\overset{O}{\underset{C-N}{\|}}\overset{H}{\underset{}{|}}$ | —CN | 157–159 |

TABLE 4-continued $$R^1-O-\overset{O}{\overset{\|}{C}}-NH-\overset{}{\underset{R^2}{C}H}-\overset{O}{\overset{\|}{C}}-NH-\overset{}{\underset{R^4}{C}H}-Z^3-A$$

| Compound No. | R$^1$ | R$^2$ | R$^4$ | Z$^3$ | A | Melting Point (°C.) or Reflactive Index (n$_D^{20}$) |
|---|---|---|---|---|---|---|
| 524 |  | C$_2$H$_5$ | CH$_3$ | $\overset{O}{\overset{\|}{C}}-\overset{H}{\underset{}{N}}$ | 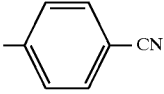—CN | 156–158 |
| 525 | 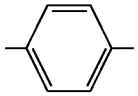—Cl | C$_3$H$_7$-i | CH$_3$ | $\overset{O}{\overset{\|}{C}}-\overset{H}{\underset{}{N}}$ | 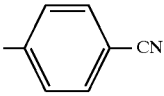—CN | 182–184 |
| 526 | C$_3$H$_7$-i | C$_3$H$_7$-i | H | $\overset{O}{\overset{\|}{C}}-\overset{H}{\underset{}{N}}$ | 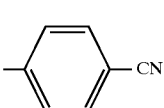—CN | 181–185 |

TABLE 5

$$R^1-Z^1-\overset{Z^2}{\overset{\|}{C}}-NH-\underset{\underset{CH_3}{\overset{CH}{\underset{|}{\diagdown}}} CH_3}{CH}-\overset{O}{\overset{\|}{C}}-NH-CH_2-CH_2-Z^3-A$$

| Compound No. | R$^1$ | Z$^1$ | Z$^2$ | Z$^3$ | A | Melting Point (°C.) or Reflactive Index (n$_D^{20}$) |
|---|---|---|---|---|---|---|
| 527 | C$_4$H$_9$-t | O | O | O | 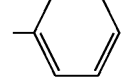 | 158–160 |
| 528 | C$_4$H$_9$-t | O | O | O | —Cl | |
| 529 | C$_4$H$_9$-t | O | O | O | 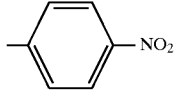—NO$_2$ | |
| 530 | C$_4$H$_9$-t | O | O | O | 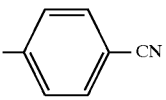—CN | |
| 531 | C$_4$H$_9$-t | O | O | O | 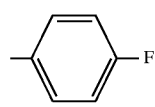—F | |
| 532 | C$_3$H$_7$-i | O | O | O | 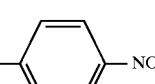—NO$_2$ | |
| 533 | C$_3$H$_7$-i | O | O | O | 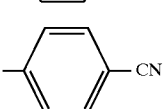—CN | |

TABLE 5-continued
$$R^1-Z^1-\underset{\underset{}{\overset{Z^2}{\|}}}{C}-NH-\underset{\underset{\underset{H_3C\phantom{-}CH_3}{\diagdown\phantom{-}\diagup}}{\underset{CH}{|}}}{CH}-\overset{O}{\overset{\|}{C}}-NH-CH_2-CH_2-Z^3-A$$
| Compound No. | $R^1$ | $Z^1$ | $Z^2$ | $Z^3$ | A | Melting Point (°C.) or Refractive Index ($n_D^{20}$) |
|---|---|---|---|---|---|---|
| 534 | $C_3H_7$-i | O | O | O | 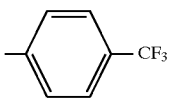 | |
| 535 | 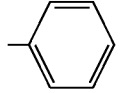 | O | O | O | 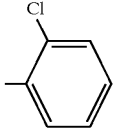 | |
| 536 | 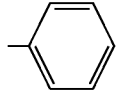 | O | O | O | 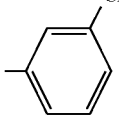 | |
| 537 | 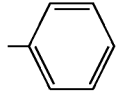 | O | O | O | 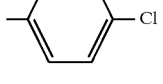 | |
| 538 | 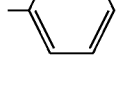 | O | O | O | 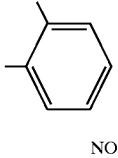 | |
| 539 | 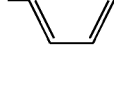 | O | O | O | 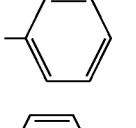 | |
| 540 |  | O | O | O | 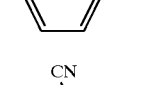 | |
| 541 | 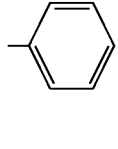 | O | O | O | 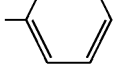 | |
| 542 | 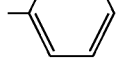 | O | O | O | 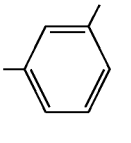 | |
| 543 | 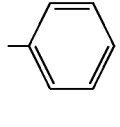 | O | O | O | 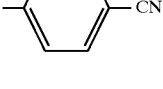 | |

TABLE 5-continued
$$R^1-Z^1-\overset{\overset{Z^2}{\|}}{C}-NH-\underset{\underset{\underset{CH_3}{\diagup}\overset{CH}{\diagdown}CH_3}{|}}{CH}-\overset{\overset{O}{\|}}{C}-NH-CH_2-CH_2-Z^3-A$$
| Compound No. | R[1] | Z[1] | Z[2] | Z[3] | A | Melting Point (°C.) or Refractive Index ($n_D^{20}$) |
|---|---|---|---|---|---|---|
| 544 | 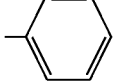 | S | O | O | —CN | |
| 545 | 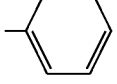 | O | S | O | 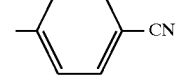—CN | |
| 546 | 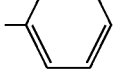 | S | S | O | —CN | |
| 547 | 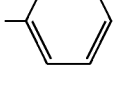 | O | O | S | 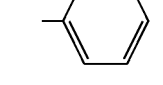 | |
| 548 | 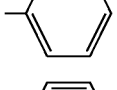 | O | O | S | 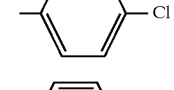—Cl | |
| 549 | 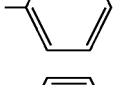 | O | O | S | 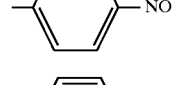—NO$_2$ | |
| 550 | 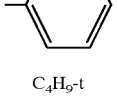 | O | O | S | 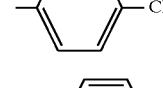—CN | |
| 551 | C$_4$H$_9$-t | O | O | S | 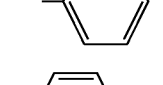 | 75–77 |
| 552 | C$_4$H$_9$-t | O | O | S | —NO$_2$ | |
| 553 | C$_4$H$_9$-t | O | O | S | —CN | |
| 554 | 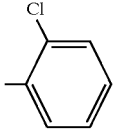 | O | O | O | 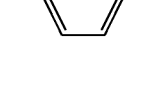—Cl | |
| 555 | 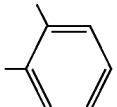 | O | O | O | 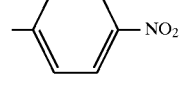—NO$_2$ | |

TABLE 5-continued $$R^1-Z^1-\overset{\overset{Z^2}{\|}}{C}-NH-\underset{\underset{\underset{CH_3}{|}}{\overset{|}{CH}}-CH_3}{\overset{|}{CH}}-\overset{\overset{O}{\|}}{C}-NH-CH_2-CH_2-Z^3-A$$

| Compound No. | R¹ | Z¹ | Z² | Z³ | A | Melting Point (°C.) or Refractive Index ($n_D^{20}$) |
|---|---|---|---|---|---|---|
| 556 | 2-Cl-C₆H₄- | O | O | O | 4-CN-C₆H₄- | |
| 557 | 3-Cl-C₆H₄- | O | O | O | 4-Cl-C₆H₄- | |
| 558 | 3-Cl-C₆H₄- | O | O | O | 4-NO₂-C₆H₄- | |
| 559 | 3-Cl-C₆H₄- | O | O | O | 4-CN-C₆H₄- | |
| 560 | 4-Cl-C₆H₄- | O | O | O | 4-Cl-C₆H₄- | |
| 561 | 4-Cl-C₆H₄- | O | O | O | 4-NO₂-C₆H₄- | |
| 562 | 4-Cl-C₆H₄- | O | O | O | 4-CN-C₆H₄- | |
| 563 | 4-OCH₃-C₆H₄- | O | O | O | 4-Cl-C₆H₄- | |
| 564 | -CH₂-C₆H₅ | O | O | O | 4-CN-C₆H₄- | |
| 565 | -CH₂-(4-CH₃-C₆H₄)- | O | O | O | 4-CN-C₆H₄- | |
| 566 | -CH₂-(4-CH₃-C₆H₄)- | O | O | O | 3,4-(OCH₃)₂-C₆H₃- | |

TABLE 5-continued
$$R^1-Z^1-\overset{\overset{Z^2}{\|}}{C}-NH-\underset{\underset{\underset{CH_3}{|}}{\overset{|}{CH}}\phantom{CH_3}}{\overset{|}{CH}}-\overset{\overset{O}{\|}}{C}-NH-CH_2-CH_2-Z^3-A$$
| Compound No. | $R^1$ | $Z^1$ | $Z^2$ | $Z^3$ | A | Melting Point (°C.) or Reflactive Index ($n_D^{20}$) |
|---|---|---|---|---|---|---|
| 567 | 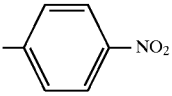 | O | O | O | 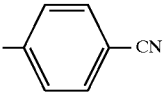 | |
| 568 | $C_3H_7$-i | O | O | O | 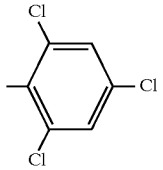 | |
| 569 | $C_3H_7$-i | O | O | O | 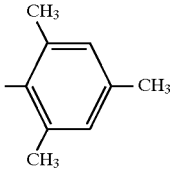 | |
| 570 | 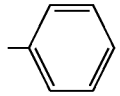 | O | O | O | 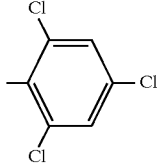 | |
| 571 | 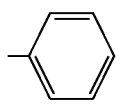 | O | O | O | 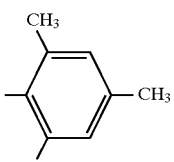 | |
| 572 | $C_3H_7$-i | O | O | NH | 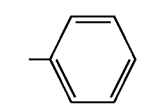 | |
| 573 | $C_3H_7$-i | O | O | NH | 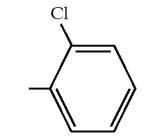 | |
| 574 | $C_3H_7$-i | O | O | NH | 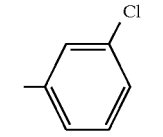 | |
| 575 | $C_3H_7$-i | O | O | NH | 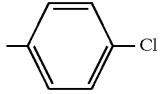 | |

TABLE 5-continued $$R^1-Z^1-\underset{\underset{\displaystyle }{\overset{\displaystyle Z^2}{\|}}}{C}-NH-\underset{\underset{\displaystyle \underset{\displaystyle CH_3}{\overset{\displaystyle |}{CH}}\, CH_3}{\overset{\displaystyle |}{CH}}}{CH}-\overset{\overset{\displaystyle O}{\|}}{C}-NH-CH_2-CH_2-Z^3-A$$

| Compound No. | R¹ | Z¹ | Z² | Z³ | A | Melting Point (°C.) or Reflactive Index ($n_D^{20}$) |
|---|---|---|---|---|---|---|
| 576 | $C_3H_7$-i | O | O | $NCH_3$ | 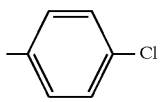 4-Cl-phenyl | |
| 577 | $C_3H_7$-i | O | O | $NCH_3$ | 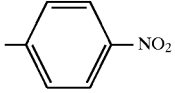 4-NO₂-phenyl | |
| 578 | $C_3H_7$-i | O | O | $NCH_3$ | 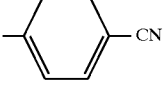 4-CN-phenyl | |
| 579 | 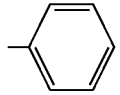 phenyl | O | O | NH | 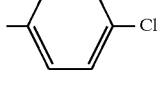 4-Cl-phenyl | |
| 580 | 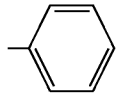 phenyl | O | O | NH | 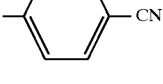 4-CN-phenyl | |
| 581 | 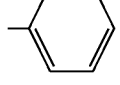 phenyl | O | O | $NCH_3$ | 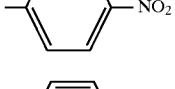 4-NO₂-phenyl | |
| 582 | 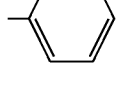 phenyl | O | O | $NCH_3$ |  4-CN-phenyl | |
| 583 | $C_3H_7$-i | O | O | S | 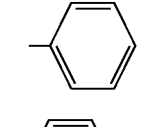 phenyl | |
| 584 | $C_3H_7$-i | O | O | S | 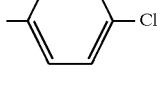 4-Cl-phenyl | |
| 585 | $C_3H_7$-i | O | O | S | 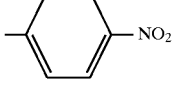 4-NO₂-phenyl | |
| 586 | $C_3H_7$-i | O | O | S | 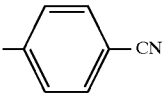 4-CN-phenyl | |
| 587 | $C_3H_7$-i | O | O | O | —CH(CH₃)— 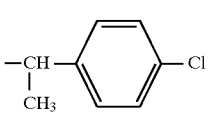 4-Cl-phenyl | |

TABLE 5-continued
$$R^1-Z^1-\overset{\overset{Z^2}{\|}}{C}-NH-\underset{\underset{\underset{CH_3}{|}}{\overset{|}{CH}}\,\overset{|}{CH_3}}{\overset{|}{CH}}-\overset{\overset{O}{\|}}{C}-NH-CH_2-CH_2-Z^3-A$$
| Compound No. | R[1] | Z[1] | Z[2] | Z[3] | A | Melting Point (°C.) or Refractive Index ($n_D^{20}$) |
|---|---|---|---|---|---|---|
| 588 | 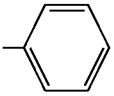 | O | O | O | 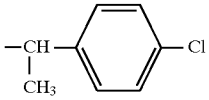 | |
| 589 | $C_3H_7$-i | O | O | O | 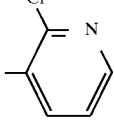 | |
| 590 | $C_3H_7$-i | O | O | O | 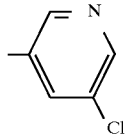 | |
| 591 | 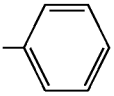 | O | O | O | 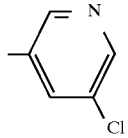 | |
| 592 | $C_3H_7$-i | O | O | O | 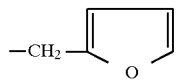 | |
| 593 | $C_3H_7$-i | O | O | O | 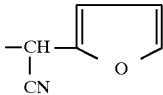 | |
| 594 | $C_3H_7$-i | O | O | O | 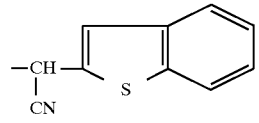 | |
| 595 | 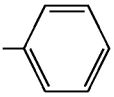 | O | O | O | 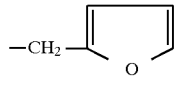 | |
| 596 | 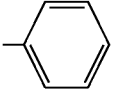 | O | O | O | 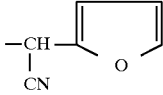 | |
| 597 | $C_3H_7$-i | O | O | O | 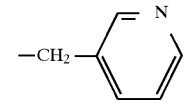 | |
| 598 | $C_3H_7$-i | O | O | O | 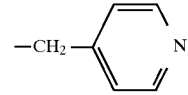 | |

TABLE 5-continued $$R^1-Z^1-\overset{\overset{Z^2}{\|}}{C}-NH-\underset{\underset{\underset{CH_3}{\diagup}\phantom{xx}\underset{CH_3}{\diagdown}}{CH}}{CH}-\overset{\overset{O}{\|}}{C}-NH-CH_2-CH_2-Z^3-A$$

| Compound No. | $R^1$ | $Z^1$ | $Z^2$ | $Z^3$ | A | Melting Point (°C.) or Reflactive Index ($n_D^{20}$) |
|---|---|---|---|---|---|---|
| 599 | ⌬ | O | O | O | $-CH_2-$(4-pyridyl) | |
| 600 | $C_3H_7$-i | O | O | O | $-CH_2-$(5-chlorobenzofuran-2-yl) | |
| 601 | $C_3H_7$-i | O | O | O | $-CH_2-$(benzothiophen-2-yl) | |

TABLE 6

$$R^1-Z^1-\overset{\overset{Z^2}{\|}}{C}-NH-\underset{\underset{\underset{CH_3}{\diagup}\phantom{xx}\underset{CH_3}{\diagdown}}{CH}}{CH}-\overset{\overset{O}{\|}}{C}-NH-\underset{\underset{CH_3}{|}}{CH}-\underset{\underset{CH_3}{|}}{CH}-Z^3-A$$

| Compound No. | $R^1$ | $Z^1$ | $Z^2$ | $Z^3$ | A | Melting Point (°C.) or Reflactive Index ($n_D^{20}$) |
|---|---|---|---|---|---|---|
| 602 | $C_4H_9$-t | O | O | O | phenyl | not determined |
| 603 | $C_4H_9$-t | O | O | O | 2-Cl-phenyl | |
| 604 | $C_4H_9$-t | O | O | O | 3-Cl-phenyl | |
| 605 | $C_4H_9$-t | O | O | O | 4-Cl-phenyl | 1.4784 |
| 606 | $C_4H_9$-t | O | O | O | 4-$NO_2$-phenyl | 1.5109 |
| 607 | $C_4H_9$-t | O | O | O | 4-CN-phenyl | not determined |

TABLE 6-continued $$R^1-Z^1-\overset{\overset{Z^2}{\|}}{C}-NH-\underset{\underset{\underset{CH_3}{|}}{\overset{|}{CH}}\overset{|}{\underset{CH_3}{|}}}{CH}-\overset{\overset{O}{\|}}{C}-NH-\underset{\underset{CH_3}{|}}{CH}-\underset{\underset{CH_3}{|}}{CH}-Z^3-A$$

| Compound No. | R¹ | Z¹ | Z² | Z³ | A | Melting Point (°C.) or Reflactive Index ($n_D^{20}$) |
|---|---|---|---|---|---|---|
| 608 | C₃H₇-i | O | O | O | —⟨C₆H₄⟩—Cl | |
| 609 | C₃H₇-i | O | O | O | —⟨C₆H₄⟩—NO₂ | |
| 610 | C₃H₇-i | O | O | O | —⟨C₆H₄⟩—CN | |
| 611 | —⟨C₆H₅⟩ | O | O | O | —⟨C₆H₅⟩ | |
| 612 | —⟨C₆H₅⟩ | O | O | O | —⟨C₆H₄⟩—Cl | |
| 613 | —⟨C₆H₅⟩ | O | O | O | —⟨C₆H₄⟩—NO₂ | |
| 614 | —⟨C₆H₅⟩ | O | O | O | —⟨C₆H₄⟩—CN | |
| 615 | —⟨C₆H₅⟩ | S | O | O | —⟨C₆H₄⟩—Cl | |
| 616 | —⟨C₆H₅⟩ | S | O | O | —⟨C₆H₄⟩—CN | |
| 617 | —⟨C₆H₅⟩ | O | S | O | —⟨C₆H₄⟩—Cl | |
| 618 | —⟨C₆H₅⟩ | O | S | O | —⟨C₆H₄⟩—CN | |
| 619 | —⟨C₆H₅⟩ | S | S | O | —⟨C₆H₄⟩—Cl | |
| 620 | —⟨C₆H₅⟩ | S | S | O | —⟨C₆H₄⟩—CN | |

TABLE 6-continued $$R^1-Z^1-\overset{\overset{Z^2}{\|}}{C}-NH-\underset{\underset{\underset{CH_3}{|}}{\overset{|}{CH}}\underset{CH_3}{|}}{\overset{|}{CH}}-\overset{\overset{O}{\|}}{C}-NH-\underset{\underset{CH_3}{|}}{\overset{|}{CH}}-\underset{\underset{CH_3}{|}}{\overset{|}{CH}}-Z^3-A$$

| Compound No. | R[1] | Z[1] | Z[2] | Z[3] | A | Melting Point (°C.) or Reflactive Index ($n_D^{20}$) |
|---|---|---|---|---|---|---|
| 621 | $C_3H_7$-i | O | O | S | —C₆H₄—Cl (4-) | |
| 622 | $C_3H_7$-i | O | O | S | —C₆H₄—CN (4-) | |
| 623 | —C₆H₅ | O | O | S | —C₆H₄—Cl (4-) | |
| 624 | —C₆H₅ | O | O | S | —C₆H₄—NO₂ (4-) | |
| 625 | —C₆H₅ | O | O | S | —C₆H₄—CN (4-) | |
| 626 | —C₆H₄—Cl (2-) | O | O | O | —C₆H₄—NO₂ (4-) | |
| 627 | —C₆H₄—Cl (2-) | O | O | O | —C₆H₄—CN (4-) | |
| 628 | —C₆H₄—Cl (3-) | O | O | O | —C₆H₄—NO₂ (4-) | |
| 629 | —C₆H₄—Cl (3-) | O | O | O | —C₆H₄—CN (4-) | |
| 630 | —C₆H₄—Cl (4-) | O | O | O | —C₆H₄—NO₂ (4-) | |
| 631 | —C₆H₄—Cl (4-) | O | O | O | —C₆H₄—CN (4-) | |

TABLE 6-continued $$R^1-Z^1-\underset{\underset{Z^2}{\|}}{C}-NH-\underset{\underset{\underset{CH_3}{|}\;\;\underset{CH_3}{|}}{CH}}{CH}-\underset{\underset{O}{\|}}{C}-NH-\underset{\underset{CH_3}{|}}{CH}-\underset{\underset{CH_3}{|}}{CH}-Z^3-A$$

| Compound No. | $R^1$ | $Z^1$ | $Z^2$ | $Z^3$ | A | Melting Point (°C.) or Reflactive Index ($n_D^{20}$) |
|---|---|---|---|---|---|---|
| 632 | —CH₂—C₆H₅ | O | O | O | —C₆H₄—CN (para) | |
| 633 | —CH₂—C₆H₃(CH₃) | O | O | O | —C₆H₃(OCH₃)(OCH₃) | |
| 634 | C₃H₇-i | O | O | O | —CH(CH₃)—C₆H₄—Cl | |
| 635 | C₆H₅ | O | O | O | —CH(CH₃)—C₆H₄—Cl | |
| 636 | C₃H₇-i | O | O | O | 5-chloropyridin-3-yl | |
| 637 | C₆H₅ | O | O | O | 5-chloropyridin-3-yl | |
| 638 | C₃H₇-i | O | O | O | —CH₂-(pyridin-3-yl) | |
| 639 | C₃H₇-i | O | O | O | —CH₂-(pyridin-4-yl) | |

TABLE 7

R¹—O—C(=O)—NH—CH(—CH(CH₃)CH₃)—C(=O)—NH—CH(CN)—CH₂—Z³—A

| Compound No. | R¹ | Z³ | A | Melting Point (°C.) or Reflactive Index ($n_D^{20}$) |
|---|---|---|---|---|
| 640 | C₄H₉-t | O | phenyl | |
| 641 | C₄H₉-t | O | 4-Cl-phenyl | |
| 642 | C₄H₉-t | O | 4-CN-phenyl | |
| 643 | C₃H₇-i | O | 4-Cl-phenyl | 153–155 |
| 644 | C₃H₇-i | O | 4-NO₂-phenyl | |
| 645 | C₃H₇-i | O | 4-CN-phenyl | |
| 646 | phenyl | O | 2-Cl-phenyl | |
| 647 | phenyl | O | 3-Cl-phenyl | |
| 648 | phenyl | O | 4-Cl-phenyl | 157–160 |
| 649 | phenyl | O | 4-NO₂-phenyl | |
| 650 | phenyl | O | 4-CN-phenyl | |

TABLE 7-continued $$R^1-O-\underset{\underset{O}{\|}}{C}-NH-CH-\underset{\underset{O}{\|}}{C}-NH-CH-CH_2-Z^3-A$$
with CH(CH₃)CH₃ on the first CH and CN on the second CH

| Compound No. | R¹ | Z³ | A | Melting Point (°C.) or Refractive Index ($n_D^{20}$) |
|---|---|---|---|---|
| 651 | 2-Cl-C₆H₄- | O | 4-Cl-C₆H₄- | |
| 652 | 2-Cl-C₆H₄- | O | 4-CN-C₆H₄- | |
| 653 | 3-Cl-C₆H₄- | O | 4-NO₂-C₆H₄- | |
| 654 | 3-Cl-C₆H₄- | O | 4-CN-C₆H₄- | |
| 655 | 4-Cl-C₆H₄- | O | 4-NO₂-C₆H₄- | |
| 656 | 4-Cl-C₆H₄- | O | 4-CN-C₆H₄- | |
| 657 | —CH₂—C₆H₅ | O | 4-Cl-C₆H₄- | |
| 658 | —CH₂—C₆H₅ | O | 4-CN-C₆H₄- | |
| 659 | —CH₂—(4-CH₃-C₆H₄) | O | 4-NO₂-C₆H₄- | |
| 660 | —CH₂—(4-CH₃-C₆H₄) | O | 4-CN-C₆H₄- | |
| 661 | C₆H₅- | S | C₆H₅- | |

TABLE 7-continued $$R^1-O-\overset{O}{\underset{\|}{C}}-NH-CH-\overset{O}{\underset{\|}{C}}-NH-CH-CH_2-Z^3-A$$
$$\underset{\underset{CH_3\ CH_3}{CH}}{|}\quad\underset{CN}{|}$$

| Compound No. | R¹ | Z³ | A | Melting Point (°C.) or Reflactive Index ($n_D^{20}$) |
|---|---|---|---|---|
| 662 | 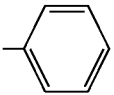 | S | 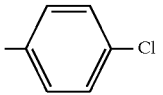 |  |
| 663 | 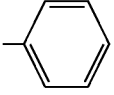 | S | 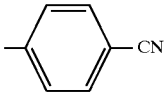 |  |
| 664 | 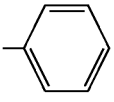 | O | 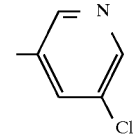 |  |
| 665 | 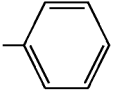 | O | 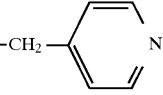 |  |

TABLE 8

$$R^1-O-\overset{O}{\underset{\|}{C}}-NH-CH-\overset{O}{\underset{\|}{C}}-NH-\overset{CH_3}{\underset{CH_3}{\underset{|}{C}}}-CH_2-Z^3-A$$
$$\underset{\underset{CH_3\ CH_3}{CH}}{|}$$

| Compound No. | R¹ | Z³ | A | Melting Point (°C.) or Reflactive Index ($n_D^{20}$) |
|---|---|---|---|---|
| 666 | C₄H₉-t | O | 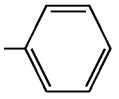 |  |
| 667 | C₄H₉-t | O | 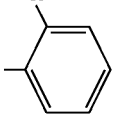 |  |
| 668 | C₄H₉-t | O | 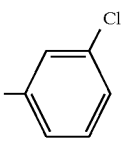 |  |
| 669 | C₄H₉-t | O | 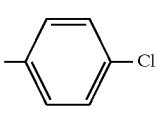 |  |

TABLE 8-continued
$$R^1-O-\overset{O}{\underset{\|}{C}}-NH-\underset{\underset{\underset{CH_3}{|}}{\overset{|}{CH}}}{\overset{|}{CH}}-\overset{O}{\underset{\|}{C}}-NH-\underset{\underset{CH_3}{|}}{\overset{\overset{CH_3}{|}}{C}}-CH_2-Z^3-A$$
| Compound No. | R¹ | Z³ | A | Melting Point (°C.) or Refractive Index ($n_D^{20}$) |
|---|---|---|---|---|
| 670 | C₃H₇-i | O | 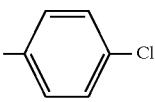 | |
| 671 | C₃H₇-i | O | 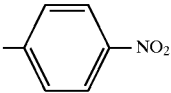 | |
| 672 | C₃H₇-i | O | 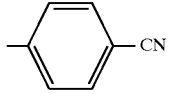 | 1.5111 |
| 673 | 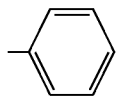 | O | 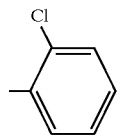 | |
| 674 | 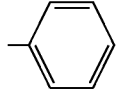 | O | 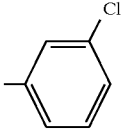 | |
| 675 | 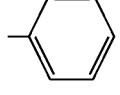 | O | 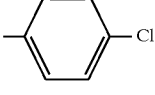 | |
| 676 | 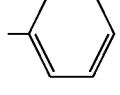 | O | 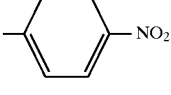 | |
| 677 | 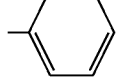 | O | 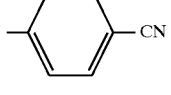 | |
| 678 | 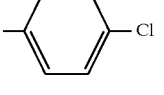 | O | 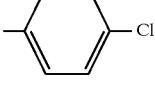 | |
| 679 | 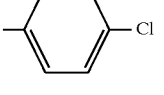 | O | 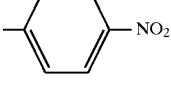 | |
| 680 | 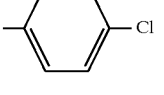 | O | 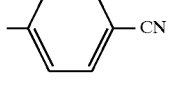 | |
| 681 | 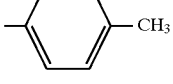 | O | 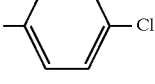 | |

TABLE 8-continued $$R^1-O-\overset{\overset{O}{\|}}{C}-NH-\underset{\underset{\underset{CH_3}{|}}{\overset{|}{CH}}}{\overset{|}{CH}}-\overset{\overset{O}{\|}}{C}-NH-\underset{\underset{CH_3}{|}}{\overset{\overset{CH_3}{|}}{C}}-CH_2-Z^3-A$$

| Compound No. | R¹ | Z³ | A | Melting Point (°C.) or Refractive Index ($n_D^{20}$) |
|---|---|---|---|---|
| 682 | -C₆H₄-CH₃ (p) | O | -C₆H₄-NO₂ (p) | |
| 683 | -C₆H₄-CH₃ (p) | O | -C₆H₄-CN (p) | |
| 684 | -C₆H₄-OCH₃ (p) | O | -C₆H₄-Cl (p) | |
| 685 | -C₆H₄-OCH₃ (p) | O | -C₆H₄-F (p) | |
| 686 | -C₆H₄-OCH₃ (p) | O | -C₆H₄-NO₂ (p) | |
| 687 | -C₆H₄-OCH₃ (p) | O | -C₆H₄-CN (p) | |
| 688 | -CH₂-C₆H₅ | O | -C₆H₄-NO₂ (p) | |
| 689 | -CH₂-C₆H₅ | O | -C₆H₄-CN (p) | |
| 690 | -CH₂-C₆H₄-NO₂ (p) | O | -C₆H₄-Cl (p) | |
| 691 | -CH₂-C₆H₄-NO₂ (p) | O | -C₆H₄-CN (p) | |
| 692 | -C₆H₅ | S | -C₆H₄-Cl (p) | |
| 693 | -C₆H₅ | S | -C₆H₄-NO₂ (p) | |
| 694 | -C₆H₅ | S | -C₆H₄-CN (p) | |

TABLE 8-continued $$R^1-O-\overset{O}{\underset{\|}{C}}-NH-\underset{\underset{CH_3}{\overset{|}{CH}}\underset{CH_3}{\overset{|}{CH}}}{\overset{|}{CH}}-\overset{O}{\underset{\|}{C}}-NH-\underset{\underset{CH_3}{\overset{|}{C}}}{\overset{CH_3}{\overset{|}{C}}}-CH_2-Z^3-A$$

| Compound No. | $R^1$ | $Z^3$ | A | Melting Point (°C.) or Reflactive Index ($n_D^{20}$) |
|---|---|---|---|---|
| 695 | $C_3H_7$-i | O | $-CH_2-C_6H_5$ | |
| 696 | $C_3H_7$-i | O | $-CH_2-C_6H_4-Cl$ | |
| 697 | $C_6H_5$ | O | $-CH_2-C_6H_5$ | |
| 698 | $C_6H_5$ | O | $-CH_2-C_6H_4-Cl$ | |

TABLE 9

$$R^1-O-\overset{O}{\underset{\|}{C}}-NH-\underset{\underset{CH_3}{\overset{|}{CH}}\underset{CH_3}{\overset{|}{CH}}}{\overset{|}{CH}}-\overset{O}{\underset{\|}{C}}-NH-\underset{\underset{C_2H_5}{\overset{|}{}}}{\overset{|}{CH}}-CH_2-Z^3-A$$

| Compound No. | $R^1$ | $Z^3$ | A | Melting Point (°C.) or Reflactive Index ($n_D^{20}$) |
|---|---|---|---|---|
| 699 | $C_4H_9$-t | O | $C_6H_5$ | |
| 700 | $C_4H_9$-t | O | 2-Cl-$C_6H_4$ | |
| 701 | $C_4H_9$-t | O | 3-Cl-$C_6H_4$ | |
| 702 | $C_4H_9$-t | O | 4-Cl-$C_6H_4$ | |
| 703 | $C_3H_7$-i | O | 4-Cl-$C_6H_4$ | |

TABLE 9-continued $$R^1-O-\overset{\overset{O}{\|}}{C}-NH-\overset{\overset{|}{CH}}{\underset{CH_3\quad CH_3}{CH}}-\overset{\overset{O}{\|}}{C}-NH-\overset{\overset{|}{CH}}{\underset{C_2H_5}{CH}}-CH_2-Z^3-A$$

| Compound No. | R¹ | Z³ | A | Melting Point (°C.) or Refractive Index ($n_D^{20}$) |
|---|---|---|---|---|
| 704 | $C_3H_7$-i | O | —⌬—NO₂ | |
| 705 | $C_3H_7$-i | O | —⌬—CN | |
| 706 | —⌬ | O | —⌬—Cl | |
| 707 | —⌬ | O | —⌬—NO₂ | |
| 708 | —⌬ | O | —⌬—CN | 128–130 |
| 709 | —⌬—Cl | O | —⌬—Cl | |
| 710 | —⌬—Cl | O | —⌬—NO₂ | |
| 711 | —⌬—Cl | O | —⌬—CN | |
| 712 | $C_3H_7$-i | O | —CH₂—⌬ | |
| 713 | $C_3H_7$-i | O | —CH₂—⌬—Cl | |
| 714 | $C_3H_7$-i | O | —CH(CH₃)—⌬ | |
| 715 | —⌬ | O | —CH₂—⌬—Cl | |

TABLE 9-continued $$R^1-O-\overset{O}{\overset{\|}{C}}-NH-CH-\overset{O}{\overset{\|}{C}}-NH-CH-CH_2-Z^3-A$$
with CH(CH$_3$)CH$_3$ on the first CH and C$_2$H$_5$ on the second CH

| Compound No. | R¹ | Z³ | A | Melting Point (°C.) or Reflactive Index (n$_D^{20}$) |
|---|---|---|---|---|
| 716 | phenyl | O | —CH(CH₃)—(4-Cl-phenyl) | |
| 717 | C₃H₇-i | O | 5-Cl-pyridin-3-yl | |
| 718 | C₃H₇-i | O | —CH₂-(pyridin-4-yl) | |
| 719 | phenyl | O | 5-Cl-pyridin-3-yl | |
| 720 | phenyl | O | —CH₂-(pyridin-4-yl) | |
| 721 | C₃H₇-i | S | 4-Cl-phenyl | |
| 722 | C₃H₇-i | S | 4-NO₂-phenyl | |
| 723 | C₃H₇-i | S | 4-CN-phenyl | |
| 724 | phenyl | S | 4-Cl-phenyl | |
| 725 | phenyl | S | 4-NO₂-phenyl | |
| 726 | phenyl | S | 4-CN-phenyl | |

TABLE 10

$$R^1-O-\underset{\underset{O}{\|}}{C}-NH-\underset{\underset{\underset{CH_3}{|}}{\overset{CH}{|}}\overset{|}{CH_3}}{CH}-\underset{\underset{O}{\|}}{C}-NH-\underset{\underset{C_3H_7}{|}}{CH}-CH_2-Z^3-A$$

| Compound No. | R¹ | Z³ | A | Melting Point (°C.) or Reflactive Index ($n_D^{20}$) |
|---|---|---|---|---|
| 727 | $C_4H_9$-t | O | 4-Cl-C₆H₄ | |
| 728 | $C_4H_9$-t | O | 4-NO₂-C₆H₄ | |
| 729 | $C_4H_9$-t | O | 4-CN-C₆H₄ | |
| 730 | $C_3H_7$-i | O | 4-Cl-C₆H₄ | |
| 731 | $C_3H_7$-i | O | 4-NO₂-C₆H₄ | |
| 732 | $C_3H_7$-i | O | 4-CN-C₆H₄ | |
| 733 | C₆H₅ | O | 4-Cl-C₆H₄ | |
| 734 | C₆H₅ | O | 4-NO₂-C₆H₄ | |
| 735 | C₆H₅ | O | 4-CN-C₆H₄ | |
| 736 | $C_3H_7$-i | S | 4-Cl-C₆H₄ | |
| 737 | $C_3H_7$-i | S | 4-NO₂-C₆H₄ | |
| 738 | C₆H₅ | S | 4-CN-C₆H₄ | |

TABLE 11

$$R^1-O-\underset{\underset{O}{\|}}{C}-NH-\underset{\underset{\underset{CH_3}{|}}{\overset{CH}{|}}\overset{|}{CH_3}}{CH}-\underset{\underset{O}{\|}}{C}-NH-CH_2-CH_2-CH_2-Z^3-A$$

| Compound No. | R¹ | Z³ | A | Melting Point (°C.) or Reflactive Index ($n_D^{20}$) |
|---|---|---|---|---|
| 739 | —CH₂—C₆H₄—CH₃ (4-) | O | 2,4-(OCH₃)₂-C₆H₃ | |
| 740 | $C_3H_7$-i | O | 4-NO₂-C₆H₄ | |

TABLE 11-continued $$R^1-O-\overset{\overset{O}{\|}}{C}-NH-\underset{\underset{\underset{CH_3}{|}}{\overset{|}{CH}}\overset{|}{\underset{CH_3}{}}}{CH}-\overset{\overset{O}{\|}}{C}-NH-CH_2-CH_2-CH_2-Z^3-A$$

| Compound No. | R[1] | Z[3] | A | Melting Point (°C.) or Reflactive Index ($n_D^{20}$) |
|---|---|---|---|---|
| 741 | $C_3H_7$-i | O | —⟨C₆H₄⟩—CN | 150–151 |
| 742 | —⟨C₆H₅⟩ | O | —⟨C₆H₄⟩—Cl | |
| 743 | —⟨C₆H₅⟩ | O | —⟨C₆H₄⟩—NO₂ | |
| 744 | —⟨C₆H₅⟩ | O | —⟨C₆H₄⟩—CN | |
| 745 | $C_3H_7$-i | S | —⟨C₆H₄⟩—CN | |
| 746 | —⟨C₆H₅⟩ | S | —⟨C₆H₄⟩—CN | |
| 747 | $C_3H_7$-i | O | —CH₂—⟨C₆H₄⟩—Cl | |
| 748 | $C_3H_7$-i | O | —⟨pyridyl⟩—Cl | |
| 749 | $C_3H_7$-i | O | —CH₂—⟨pyridyl⟩ | |

TABLE 12
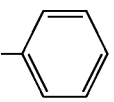
| Compound No. | $R^1$ | $R^4$ | $R^5$ | $R^6$ | A | Melting Point (°C.) or Refractive Index ($n_D^{20}$) |
|---|---|---|---|---|---|---|
| 750 | 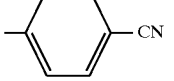 | H | H | $CH_3$ | 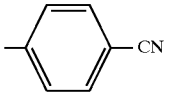 —CN | not determined |
| 751 | $C_4H_9$-t | H | H | $CH_3$ | 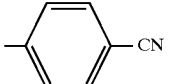 —CN | 46–50 |
| 752 | $C_3H_7$-i | H | H | $CH_3$ | 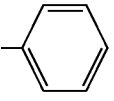 —CN | |
| 753 | 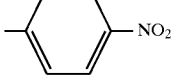 | H | H | $CH_3$ | 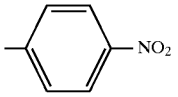 —$NO_2$ | |
| 754 | $C_4H_9$-t | H | H | $CH_3$ | 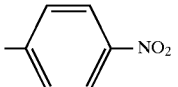 —$NO_2$ | |
| 755 | $C_3H_7$-i | H | H | $CH_3$ |  —$NO_2$ | |
| 756 | 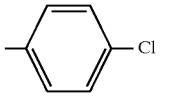 | H | H | $CH_3$ | 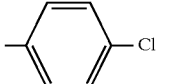 —Cl | |
| 757 | $C_4H_9$-t | H | H | $CH_3$ | 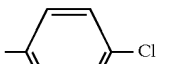 —Cl | |
| 758 | $C_3H_7$-i | H | H | $CH_3$ | 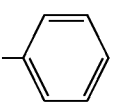 —Cl | |
| 759 | 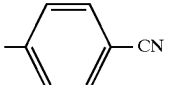 | H | $CH_3$ | $CH_3$ | 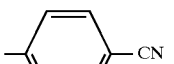 —CN | |
| 760 | $C_4H_9$-t | H | $CH_3$ | $CH_3$ | 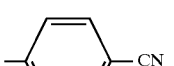 —CN | |
| 761 | $C_3H_7$-i | H | $CH_3$ | $CH_3$ | 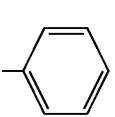 —CN | |
| 762 | 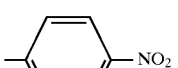 | H | $CH_3$ | $CH_3$ | —$NO_2$ | |

TABLE 12-continued
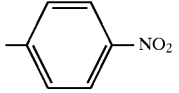
| Compound No. | R¹ | R⁴ | R⁵ | R⁶ | A | Melting Point (°C.) or Refractive Index ($n_D^{20}$) |
|---|---|---|---|---|---|---|
| 763 | C₄H₉-t | H | CH₃ | CH₃ | 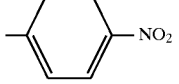 | |
| 764 | C₃H₇-i | H | CH₃ | CH₃ | 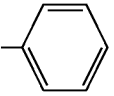 | |
| 765 | 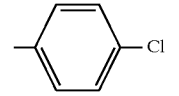 | H | CH₃ | CH₃ |  | |
| 766 | C₄H₉-t | H | CH₃ | CH₃ | 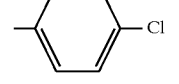 | |
| 767 | C₃H₇-i | H | CH₃ | CH₃ | 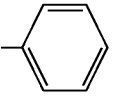 | |
| 768 | 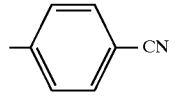 | C₃H₇-i | H | H | 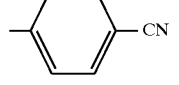 | 150–152 |
| 769 | C₄H₉-t | C₃H₇-i | H | H | 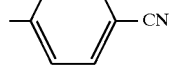 | |
| 770 | C₃H₇-i | C₃H₇-i | H | H | 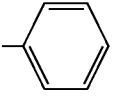 | 154–157 |
| 771 | 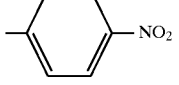 | C₃H₇-i | H | H | 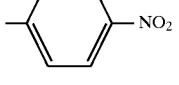 | |
| 772 | C₄H₉-t | C₃H₇-i | H | H | 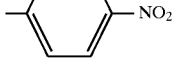 | |
| 773 | C₃H₇-i | C₃H₇-i | H | H | 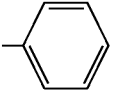 | |
| 774 | 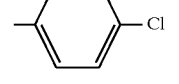 | C₃H₇-i | H | H | | |

TABLE 12-continued $$R^1-O-\overset{O}{\underset{\|}{C}}-NH-\underset{\underset{CH_3}{\overset{|}{CH}}\diagdown CH_3}{\overset{|}{CH}}-\overset{O}{\underset{\|}{C}}-NH-\underset{\underset{R^4}{|}}{CH}-\underset{\underset{R^6}{|}}{\overset{R^5}{\overset{|}{C}}}-O-A$$

| Compound No. | $R^1$ | $R^4$ | $R^5$ | $R^6$ | A | Melting Point (°C.) or Reflactive Index ($n_D^{20}$) |
|---|---|---|---|---|---|---|
| 775 | $C_4H_9$-t | $C_3H_7$-i | H | H | 4-Cl-C6H4- | |
| 776 | $C_3H_7$-i | $C_3H_7$-i | H | H | 4-Cl-C6H4- | |

TABLE 13

$$R^1-O-\overset{O}{\underset{\|}{C}}-NH-\underset{\underset{CH_3\diagdown CH_3}{\overset{|}{CH}}}{\overset{\overset{H}{|}}{\overset{*}{C}}}-\overset{O}{\underset{\|}{C}}-NH-\underset{\underset{CH_3}{|}}{\overset{CH_3}{\overset{|}{C}}}-CH_2-O-A$$

| Compound No. | $R^1$ | Optically Isomeric Form of C* | A | Melting Point (°C.) or Reflactive Index ($n_D^{20}$) |
|---|---|---|---|---|
| 777 | 2-F-C6H4- | L | 4-CN-C6H4- | 115–116 |
| 778 | 2-F-C6H4- | DL | 4-CN-C6H4- | |
| 779 | 3-F-C6H4- | L | 4-CN-C6H4- | 146–147 |
| 780 | 3-F-C6H4- | DL | 4-CN-C6H4- | |
| 781 | 4-F-C6H4- | L | 4-CN-C6H4- | 130–131 |
| 782 | 4-F-C6H4- | DL | 4-CN-C6H4- | 164–165 |

TABLE 13-continued $$R^1-O-\overset{O}{\underset{\|}{C}}-NH-\overset{H}{\underset{\overset{|}{CH}}{\underset{/\backslash}{C}}}\overset{O}{\underset{\|}{*}}-C-NH-\overset{CH_3}{\underset{\overset{|}{C}}{\underset{\overset{|}{CH_3}}{C}}}-CH_2-O-A$$
$$CH_3\quad CH_3$$

| Compound No. | $R^1$ | Optically Isomeric Form of C* | A | Melting Point (°C.) or Reflactive Index ($n_D^{20}$) |
|---|---|---|---|---|
| 783 | 2,3-difluorophenyl | L | 4-cyanophenyl | |
| 784 | 2,3-difluorophenyl | DL | 4-cyanophenyl | |
| 785 | 3,4-difluorophenyl | L | 4-cyanophenyl | 114–116 |
| 786 | 3,4-difluorophenyl | DL | 4-cyanophenyl | |
| 787 | 2,4-difluorophenyl | L | 4-cyanophenyl | |
| 788 | 2,4-difluorophenyl | DL | 4-cyanophenyl | |

Next, synthesis processes of the compounds represented by Formula [I] according to the present invention will be explained.

Preparation Process A

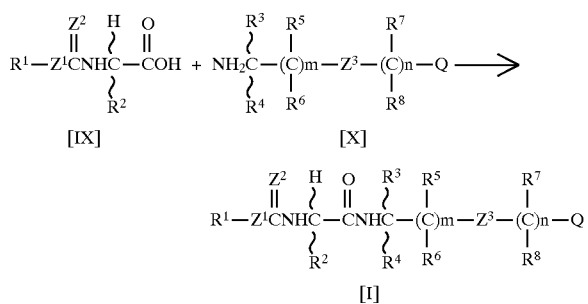

wherein $R^1$, $R^2$, $R^3$, $R^4$, $R^5$, $R^6$, $R^7$, $R^8$, $Z^1$, $Z^2$, $Z^3$, Q, m, and n have the same meanings as defined above.

The compounds represented by Formula [I] according to the present invention can be prepared by reacting an amino acid derivative represented by Formula [IX] or the amino acid derivative possessing the activated carboxyl group, with an amine represented by Formula [X] in the presence of a base and/or a catalyst, if necessary.

In the present reaction, as the amino acid derivative represented by Formula [IX] with the activated carboxyl group, there can be mentioned, for example, an acid halide such as an acid chloride, an acid anhydride derived from the two molecules of the amino acid derivatives represented by Formula [TX], a mixed acid anhydride derived from the amino acid derivative represented by Formula [IX] and other acid or an O-alkyl carbonic acid, and an activated ester such as p-nitrophenyl ester, 2-tetrahydropyranyl ester, and 2-pyridyl ester and the like.

It is possible to perform the present reaction using a condensing agent such as N, N'-dicyclohexylcarbodiimide, carbonyldiimidazole, 2-chloro-1,3-dimethylimidazolium chloride, or the like.

The present reaction can be carried out in a conventional solvent: this solvent can be any solvent that does not hinder the reaction; for example, hydrocarbons such as pentane, hexane, heptane, cyclohexane, petroleum ether, ligroin, benzene, toluene, xylene and the like; halogenated hydrocarbons such as dichloromethane, dichloroethane, chloroform, carbon tetrachloride, chlorobenzene, dichlorobenzene and the like; ethers such as diethyl ether, diisopropyl ether, ethylene glycol dimethyl ether, tetrahydrofuran, dioxane and the like; ketones such as acetone, methyl ethyl ketone, methyl isopropyl ketone, methyl isobutyl ketone and the like; esters such as methyl acetate, ethyl acetate, and the like; nitriles such as acetonitrile, propionitrile, benzonitrile and the like; aprotic polar solvents such as dimethylsulfoxide, dimethylformamide, sulfolane and the like; and mixed solvents combining solvents selected from the aforementioned.

The base can be any type of base generally used in this type of reaction. For example, there can be mentioned hydroxides of alkaline metals such as sodium hydroxide, potassium hydroxide and the like; hydroxides of alkaline earth metals such as calcium hydroxide and the like; carbonates of alkaline metals such as sodium carbonate, potassium carbonate and the like; bicarbonates of alkaline metals such as sodium bicarbonate, potassium bicarbonate and the like; organic bases such as triethylamine, trimethylamine, dimethylaniline, pyridine, N-methylmorpholine, N-methylpiperidine, 1,5-diazabicyclo [4.3.0] non-5-ene (DBN), 1,8-diazabicyclo[5.4.0] undec-7-ene (DBU), and the like; and preferably tertiary amines such as triethylamine, pyridine, N-methylpiperidine and the like.

As the catalyst, there can be mentioned 4-dimethylaminopyridine, 1-hydroxybenzotriazole, dimethylformamide and the like.

The present reaction is carried out at a temperature of −75° C. to 100° C., preferably −60° C. to 40° C. The reaction time is preferably 1 to 20 hours.

Furthermore, compounds represented by Formula [IX] as the starting material can be synthesized, for example by reacting L-valine with di(tert-butyl) dicarbonate in the presence of sodium bicarbonate to afford N-tert-butoxycarbonyl-L-valine, or by reacting D,L-valine with carbobenzoxy chloride in the presence of sodium bicarbonate to afford N-benzyloxycarbonyl-DL-valine (see *Methoden der Organischen Chemie*, Vol. 15, No. 2, page 2 seq.; Georg Thieme Verlag Stuttgart: 1974; *Chemistry of the Amino Acids*, vol. 2, page 891; John Wiley & Sons, N.Y. (1964); and *Journal of the American Chemical Society*, Vol. 79, page 4686 (1957)).

Among the amino acid derivatives with the activated carboxyl groups as the starting material, the mixed acid anhydride can be synthesized by reacting the amino acid derivative represented by Formula [IX] with pivaloyl chloride in the presence of an organic base. p-Nitrophenyl ester can be prepared by reacting the amino acid derivative represented by Formula [IX] with p-nitrophenol in the presence of a condensing agent (see *Methoden der Organischen Chemie*, Vol. 15, No. 2, page 2 seq.; *Georg Thieme Verlag Stuttgart:* 1974; *Chemische Berichte*, vol. 38, page 605 (1905); *Journal of the American Chemical Society*, Vol. 74, page 676 (1952); and *Journal of the American Chemical Society*, Vol. 86, page 1839 (1964)).

In addition, the compounds represented by Formula [X] can be synthesized by means of reacting chlorobenzonitrile with 2-amino-2-methyl-1-propanol in the presence of sodium hydride (see Japanese Patent Application First Publication No. Sho 63-146876, Japanese Patent Application First Publication No. Hei 5-271206, Tetrahedron *Letters*, page 21, 1973).

Preparation Process B

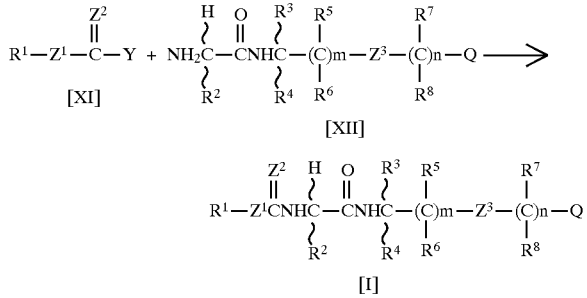

wherein $R^1$, $R^2$, $R^3$, $R^4$, $R^5$, $R^6$, $R^7$, $R^8$, $Z^1$, $Z^2$, $Z^3$, Q, m, and n have the same meanings as defined above, and Y represents a halogen atom, a 4,6-dimethylpyrimidinylthio group, an $R^1OC(O)O—$ group, or a

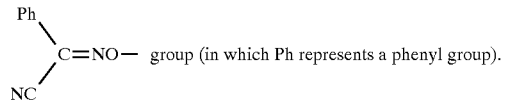

Compounds of the present invention represented by Formula [I] can be manufactured by means of reacting the compound represented by Formula [XI] with an amine represented by Formula [XII] or the salt of the amine derivative with an inorganic acid such as hydrochloride and the like, or a salt of the amine derivative with an organic acid such as tosylate and the like, in the presence of a base when required.

The present reaction can be performed in a conventional solvent. This solvent can be any solvent that does not hinder the reaction; for example, hydrocarbons such as pentane, hexane, heptane, cyclohexane, petroleum ether, ligroin, benzene, toluene, xylene and the like; halogenated hydrocarbons such as dichloromethane, dichloroethane, chloroform, carbon tetrachloride, chlorobenzene, dichlorobenzene and the like; ethers such as diethyl ether, diisopropyl ether, ethylene glycol dimethyl ether, tetrahydrofuran, dioxane and the like; ketones such as acetone, methyl ethyl ketone, methyl isopropyl ketone, methyl isobutyl ketone and the like; esters such as methyl acetate, ethyl acetate and the like, nitriles such as acetonitrile, propionitrile, benzonitrile and the like; aprotic polar solvents such as dimethylsulfoxide, dimethylformamide, sulfolane and the like; water; and mixtures of solvents combining solvents selected from the aforementioned.

The base can be any type of base generally used in this type of reaction. For example, there can be mentioned hydroxides of alkaline metals such as sodium hydroxide, potassium hydroxide and the like; hydroxides of alkaline earth metals such as calcium hydroxide and the like; carbonates of alkaline metals such as sodium carbonate, potassium carbonate and the like; bicarbonates of alkaline metals such as sodium bicarbonate, potassium bicarbonate and the like; organic bases such as triethylamine, trimethylamine, dimethylaniline, N-methylmorpholine, pyridine, N-methylpiperidine, 1,5-diazabicyclo [4.3.0] non-5-ene (DBN), 1,8-diazabicyclo [5.4.0] undec-7-ene (DBU), and the like, and preferably tertiary amines such as triethylamine, pyridine, N-methylpiperidine and the like.

The present reaction is carried out at a temperature of −20° C. to 100° C., and preferably 0° C. to 40° C. The reaction time is usually 30 minutes to 20 hours.

Compounds represented by Formula [XII] as the starting material are novel compounds, and can be manufactured, for example, by means of treating carbamates of Formula [I] synthesized by the procedure of preparation process A using a conventional process for removing the amino protecting group of the amino acid, such as catalytic reduction, or by treating with acids such as liquid hydrofluoric acid, sulfonic acids, hydrochloric acid, hydrobromic acid, formic acid and the like.

In the following, synthesis examples of the intermediates of the compounds according to the present invention, represented by Formula [X], are provided as reference examples.

Reference Example 1

Synthesis of 2-(4-cyanophenoxy)-1-methylethylamine (part 1)

293 g of ammonium acetate and 16.7 g of sodium cyanoborohydride were added to a solution containing 66.5 g of 4-cyanophenoxyacetone dissolved in 1500 ml of methanol, and the resultant mixture was stirred for 30 hours at room temperature. The reaction mixture was then concentrated under reduced pressure, and acidified with concentrated hydrochloric acid. 500 ml of diethyl ether and 300 ml of water were then added thereto. Subsequently, the resultant water layer was made basic with a 5% aqueous solution of sodium hydroxide, the solution was extracted with 1000 ml of diethyl ether, and then washed with water. The organic layer was then dried over anhydrous sodium sulfate, and the diethyl ether was removed under reduced pressure. The obtained residue was distilled under reduced pressure to yield 13.0 g of the desired product (19%).

Boiling point: 132° C./0.26 mmHg.

Reference Example 2

Synthesis of 2-(4-cyanophenoxy)-1-methylethylamine (part 2)

50.0 g of 2-amino-1-propanol was added drop by drop to a mixture containing 29.3 g of 60% sodium hydride and 300 ml of N,N-dimethylformamide, in an ice bath, and the resultant mixture was stirred for 30 minutes in an ice bath. A solution containing 121.2 g of 4-bromobenzonitrile dissolved in N,N-dimethylformamide was added slowly to the reaction mixture while being stirred in an ice bath, followed by stirring the reaction mixture for 20 hours at room temperature. After the completion of the reaction, the resultant mixture was poured into water and extracted with ethyl acetate. The organic layer was washed with water and then dried over anhydrous magnesium sulfate, and the ethyl acetate was removed under reduced pressure. The obtained residue was distilled under reduced pressure to yield 48.0 g of the desired product (41%).

Boiling point: 132° C./0.26 mmHg.

Reference Example 3

Synthesis of 2-(4-chloro-2-methylphenoxy)-1-methylethylamine 120 g of ammonium acetate and 9.8 g of sodium cyanoborohydride were added to a solution containing 31 g of (4-chloro-2-methylphenoxy)acetone dissolved in 700 ml of methanol, and the resultant mixture was stirred for 20 hours at room temperature. After the reaction mixture was concentrated under reduced pressure, 180 ml of concentrated hydrochloric acid and 100 ml of water were added to the residue. The whole mixture was stirred for 1 hour, and then 300 ml of diethyl ether was added thereto. The aqueous layer was alkalified using a 5% aqueous solution of sodium hydroxide, and then extracted with 500 ml of ethyl acetate. The organic layer was washed with water, dried over anhydrous magnesium sulfate, and then concentrated under reduced pressure. A fraction possessing a low boiling point was removed from the obtained oily products to afford 25 g (yield 81 %) of the desired product.

Refractive index ($n^{20}$): 1.5360.

Reference Example 4

Synthesis of 2-(4-chlorophenoxy)-1-methylpropylamine 82 g of ammonium acetate and 6.7 g of sodium cyanoborohydride were added to a solution containing 21 g of 3-(4-chlorophenoxy)-2-butanone dissolved in 500 ml of methanol, and the reaction mixture was stirred for 20 hours at room temperature. After the reaction mixture was concentrated under reduced pressure, 180 ml of concentrated hydrochloric acid, 100 ml of water, and 300 ml of diethyl ether were added to the residue. The obtained water layer was alkalified using a 5% aqueous solution of sodium hydroxide, and then the organic substances were extracted with 500 ml of ethyl acetate. The organic layer was washed with water, dried over anhydrous magnesium sulfate, and then concentrated under reduced pressure. A fraction possessing a low boiling point was removed from the obtained oily products to afford 18 g (yield 86%) of the desired product.

Refractive index ($n^{20}$): 1.5360.

Reference Example 5

Synthesis of 1-methyl-2-(2-methylphenoxy)ethylamine

A solution containing 36 g of 2-(2-methylphenoxy) acetone oxime O-methyl ether dissolved in 150 ml of dimethoxyethane was added dropwise to a suspension containing 13 g of sodium borohydride in 500 ml of dimethoxyethane at room temperature. After the mixture was stirred for 15 minutes at room temperature, a solution containing 66 g of boron trifluoride diethyl ether complex dissolved in 100 ml of dimethoxyethane was added dropwise to the mixture at room temperature. The reaction mixture was stirred for 30 minutes at room temperature and then refluxed for 3 hours. The resultant mixture was allowed to sit and cool naturally to room temperature and then acidified using a 10% hydrochloric acid. The dimethoxyethane layer was concentrated and combined with the water layer. The mixture was alkalified using sodium carbonate, and then extracted with dichloromethane, followed by washing with water. The organic layer was dried over anhydrous magnesium sulfate, and then the dichloromethane was removed under reduced pressure. The residue was distilled under reduced pressure to obtain 6.4 g (yield 21%) of the desired product.

Boiling point: 65° C./0.08 mmHg.

Reference Example 6

Synthesis of (−)-2-(4-cyanophenoxy)-1-methylethylamine 25.0 g of R-(−)-2-amino-1-propanol was added dropwise to a stirred mixture of 14.0 g of 60% sodium hydride and 200 ml of N,N-dimethylformamide, at 5° C. ~10° C. while being stirred. After the reaction mixture was stirred for 30 minutes at the same temperature, a solution containing 45.0 g of 4-chlorobenzonitrile dissolved in N,N-dimethylformamide was added dropwise to the reaction mixture. The resultant mixture was stirred for 20 hours at room temperature. After the completion of the reaction, the resultant mixture was poured into water and extracted with ethyl acetate. The organic layer was washed with water and then dried over anhydrous magnesium sulfate. The ethyl acetate was removed under reduced pressure. The residue was distilled under reduced pressure to obtain 33.0 g of the desired product (yield 56%).

Boiling point: 60° C.~66° C./0.08 mmHg.

$[\alpha]_D^{20}$: −15.70° (C: 1.0, $CH_3OH$).

Reference Example 7

Synthesis of 1-methyl-2-(2-pyrimidyloxy)ethylamine 2.0 g of 2-amino-1-propanol was added dropwise to a stirred mixture of 1.3 g of 60% sodium hydride and 30 ml of N,N-dimethylformamide at room temperature. After the reaction mixture was stirred for 30 minutes, a solution containing 3.7 g of 2-chloropyrimidine dissolved in N,N-dimethylformamide was added dropwise to the reaction mixture. The mixture was stirred for 2 hours at 100° C. After completion of the reaction, the reaction mixture was cooled. The solids in the reaction mixture were filtered off. The solvent in the filtrate was removed under reduced pressure. The residue was purified by column chromatography on silica gel to obtain 2.1 g of the desired product (yield: 50%). Refractive index ($n^{20}$): 1.5481.

Reference Example 8

Synthesis of 1-methyl-2-(4-pyridyloxy)ethylamine 6.2 g of 2-amino-1-propanol was added dropwise to a stirred mixture of 4.0 g of 60% sodium hydride and 50 ml of N,N-dimethylformamide at 5° C.~10° C. After the reaction mixture was stirred for 30 minutes, 12.5 g of 4-chloropyridine hydrochloride in limited amounts was added to the reaction mixture. The mixture was stirred for 20 hours at room temperature. After completion of the reaction, the solids in the reaction mixture were filtered off. The solvent in the filtrate was removed under reduced pressure. The residue was purified by column chromatography on silica gel to obtain 3.8 g of the desired product (yield: 30%). Refractive index ($n^{20}$): 1.5469.

Reference Example 9

Synthesis of 2-(4-cyanophenoxy)-1,1-dimethylethylamine 4.0 g of 60% sodium hydride was added to a solution containing 8.9 g of 2-amino-2-methyl-1-propanol dissolved in 100 ml of N,N-dimethylformamide in an ice bath. After the reaction mixture was stirred for 30 minutes at room temperature, 13.7 g of 4-chlorobenzonitrile was added to the reaction mixture and the reaction mixture was stirred for 15 hours at room temperature. The reaction mixture was poured into water. The organic layer of the reaction mixture was extracted with ethyl acetate, washed with water, and then dried over anhydrous magnesium sulfate. After the solvent was removed under reduced pressure. The fraction possessing a low boiling point was removed from the residue, thus obtaining 15 g of the desired product (yield: 79%).

According to the procedures similar to those in the Reference Examples described above, the following intermediates were obtained:

(RS) 2-(2-methoxyphenoxy)-1-methylethylamine
Boiling point: 96.5° C./0.15 mmHg.
(RS) 2-(3-methoxyphenoxy)-1-methylethylamine
Refractive Index ($n^{20}$): 1.5158.
(RS) 2-(4-methoxyphenoxy)-1-methylethylamine
Boiling point: 95° C./0.10 mmHg.
(RS) 2-(2-cyanophenoxy)-1-methylethylamine
Refractive Index ($n^{20}$): 1.5566.
(RS) 2-(3-cyanophenoxy)-1-methylethylamine
Refractive Index ($n^{20}$): 1.5409.
(RS) 2-(2-fluorophenoxy)-1-methylethylamine
Boiling point: 70° C./0.22 mmHg.
(RS) 2-(3-fluorophenoxy)-1-methylethylamine
Boiling point: 74° C. /0.15 mmHg.
(RS) 2-(2-nitrophenoxy)-1-methylethylamine
Refractive Index ($n^{20}$): 1.5582.
(RS) 2-(2,4-dichlorophenoxy)-1-methylethylamine
Refractive Index ($n^{20}$): 1.5475.
(RS) 2-(3,4-dichlorophenoxy)-1-methylethylamine
Boiling point: 104° C./0.16 mmHg.
(RS) 2-(3,5-dichlorophenoxy)-1-methylethylamine
Boiling point: 100° C./0.12 mmHg.
(RS) 2-(3,4-dimethoxyphenoxy)-1-methylethylamine
Refractive Index ($n^{20}$): 1.5361.
(RS) 2-(3,5-dimethoxyphenoxy)-1-methylethylamine
Boiling point: 12.5° C./0.10 mmHg.
(1RS)(2R,S) 2-(4-cyanophenoxy)-1-methylethylamine
Refractive Index ($n^{20}$): 1.5480.
(1RS)(2R,S) 1,2-dimethyl-2-(4-nitrophenoxy)-ethylamine
Refractive Index ($n^{20}$): 1.6263.

Next, the synthesis examples of the intermediates of the compounds according to the present invention, represented by Formula [XII] are described in the following Reference Examples.

Reference Example 10

Synthesis of $N^1$-[2-(4-cyanophenoxy)-1-methylethyl]-L-valinamide hydrochloride Hydrogen chloride gas was introduced into a solution containing 3.7 g of $N^2$-tert-butoxycarbonyl-$N^1$-[2-(4-cyanophenoxy)-1-methylethyl]-L-valinamide dissolved in 100 ml of methylene chloride for 1 hour at room temperature. After the completion of the reaction, the methylene chloride was removed under reduced pressure, thus yielding a crude crystal. The crude crystal was washed with acetone to afford 3.1 g of the desired product (yield: 100%).

Melting point: 59°~63° C.

Reference Example 11

Synthesis of $N^1$-[2-(4-cyanophenoxy)-1-methylethyl]-L-isoleucinamide

Hydrogen chloride gas was introduced into a solution containing 15.0 g of $N^2$-tert-butoxycarbonyl-$N^1$-[2-(4-cyanophenoxy)-1-methylethyl]-L-isoleucinamide dissolved in 300 ml. of methylene chloride for 1 hour at room temperature. After the completion of the reaction, the methylene chloride was removed under reduced pressure, thus yielding a crude crystal. 200 ml of a saturated aqueous solution of sodium bicarbonate and 200 ml of methylene chloride were added to the crude crystal, and subsequently the mixture was stirred for 30 minutes. The organic substances were extracted with methylene chloride. The organic layer was washed with water, and dried over anhydrous sodium sulfate. The methylene chloride was removed under reduced pressure. The obtained crude crystal was washed with acetone to afford 10.0 g of the desired product (yield: 90%).

Melting point: 64°~67° C.

Reference Example 12

Synthesis of $N^1$-[2-(4-cyanophenoxy)-1,1-dimethylethyl]-L-valinamide

Hydrogen chloride gas was introduced into a solution containing 3.7 g of $N^2$-tert-butoxycarbonyl-$N^1$ -[2-(4-cyanophenoxy)-1,1-dimethylethyl]-L-valinamide dissolved in 50 ml of methylene chloride for 3 hours at room temperature. After the completion of the reaction, the methylene chloride was removed under reduced pressure. A saturated aqueous solution of sodium bicarbonate was added to the residue. The organic layer in the residue was extracted with methylene chloride, washed with water, and then dried over anhydrous magnesium sulfate. The solvent in the organic layer was removed under reduced pressure, thus yielding 2.4 g of the desired product (yield: 87%).

According to the procedures similar to those in the Reference Examples described above, the following intermediates were obtained:

(RS) $N^1$-2-(5-trifluoropyridin-2-yl)oxy-1-methylethyl]-L-valinamide

Melting point: 73° C.~75° C.

(RS) N-[2-(4-chlorophenoxy)-1-methylethyl]-L-2-aminobutyramide

Melting point: 43° C.~44° C.

(RS) N-[2-(4-cyanophenoxy)-1-methylethyl]-L-2-aminobutyramide

Refractive Index ($n^{20}$): 1.5391.

(RS) N-[2-(4-cyanophenoxy)-1-methylethyl]-L-2-aminovaleramide

Refractive Index ($n^{20}$): 1.5299.

(RS) N-[2-(4-cyanophenoxy)-1-methylethyl]-L-2-amino-3,3-dimethylbutyramide

Refractive Index ($n^{20}$): 1.5251.

(RS) $N^1$-[2-(4-cyanophenoxy)-1-methylethyl]-L-valinamide

Refractive Index ($n^{20}$): 1.5250.

BEST MODE FOR CARRYING OUT THE INVENTION

The methods for producing the compounds according to the present invention will be described in detail in the following Synthesis Examples.

Synthesis Example 1

Synthesis of $N^2$-tert-butoxycarbonyl-$N^1$-[1-methyl-2-(4-nitrophenoxy)ethyl]-L-valinamide (Compound No. 16)

0.5 g of N-methylpiperidine was added to a solution containing 1.1 g of N-tert-butoxycarbonyl-L-valine dissolved in 40 ml of methylene chloride, at –20° C. After the mixture was stirred for 10 minutes at the same temperature, 0.7 g of isobutyl chloroformate was added to the mixture at –40° C., and subsequently the whole mixture was stirred for 1 hour at –20° C. 1 g of 1-methyl-2-(4-nitrophenoxy)ethylamine was added to this mixture at –60° C., and then the reaction mixture was allowed to sit and warm naturally to room temperature while being stirred. The whole mixture was stirred for 15 hours at room temperature. Water was subsequently added to the reaction mixture. After the dichloromethane layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus yielding 0.7 g of the desired product in the form of a yellow powder (yield: 55%).

Synthesis Example 2

Synthesis of $N^1$-[2-(4-cyanophenoxy)-1-methylethyl]-$N^2$-isopropenyloxycarbonyl-L-valinamide (Compound No. 77)

0.6 g of N-methylmorpholine, and subsequently 0.4 g of isopropyl chloroformate were added to a solution containing 0.9 g of $N^1$-[2-(4-cyanophenoxy)-1-methylethyl]-L-valinamide hydrochloride dissolved in 50 ml of methylene chloride at –15° C. The mixture was allowed to sit and warm naturally to room temperature and stirred for 15 hours at room temperature. Water was subsequently added to the reaction mixture. After the dichloromethane layer was washed with water, the organic layer was dried over anhydrous magnesium sulfate and then the methylene chloride was removed under reduced pressure. The residue was purified by column chromatography on silica gel, thus yielding 0.23 g of the desired product in the form of colorless grains (yield: 13%).

Synthesis Example 3

Synthesis of $N^1$-[2-(4-cyanophenoxy)-1-methylethyl]-$N^2$-phenoxycarbonyl-L-valinamide (Compound No. 107)

1.3 g of N-methylpiperidine was added to a solution containing 3 g of N-phenoxycarbonyl-L-valine dissolved in 50 ml of methylene chloride, at –20° C. After the mixture was stirred for 10 minutes at the same temperature, 1.7 g of isobutyl chloroformate was added to the mixture at –40° C., and subsequently the whole mixture was stirred for 1 hour at –20° C. 2.2 g of 2-(4-cyanophenoxy)-1-methylethylamine was added to this mixture at –60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus yielding 1.1 g of the desired product in the form of a white powder (yield: 22%).

Synthesis Example 4

Synthesis of $N^2$-tert-butoxycarbonyl-$N^1$-[2-(4-cyanophenoxy)-1-methylethyl]-L-isoleucinamide (Compound No. 228)

1.3 g of N-methylpiperidine was added to a solution containing 3 g of N-tert-butoxycarbonyl-L-isoleucine dissolved in 60 ml of miethylene chloride, at –20° C. After the mixture was stirred for 10 minutes at the same temperature, 1.8 g of isobutyl chloroformate was added to the mixture at –40° C., and subsequently the whole mixture was stirred for 1 hour at –20° C. 2.3 g of 2-(4-cyanophenoxy)-1-methylethylamine was added to this mixture at –60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 0.6 g of the desired product in the form of a white powder (yield: 12%).

Synthesis Example 5

Synthesis of $N^2$-tert-butoxycarbonyl-$N^1$-(2-phenylthioethyl)-L-valinamide (Compound No. 551)

1 g of N-methylpiperidine was added to a solution containing 2.1 g of N-tert-butoxycarbonyl-L-valine dissolved in 40 ml of methylene chloride, at –20° C. After the mixture was stirred for 10 minutes at the same temperature, 1.3 g of isobutyl chloroformate was added to the mixture, and subsequently the whole mixture was stirred for 1 hour at –20° C. 1.5 g of 2-phenylthioethylamine was added to this mixture at –60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 0.4 g of the desired product in the form of cream yellow grains (yield: 12%).

Synthesis Example 6

Synthesis of $N^2$-tert-butoxycarbonyl-$N^1$-[1-methyl-2-(4-nitrophenoxy)propyl]-L-valinamide (Compound No. 606)

0.5 g of N-methylpiperidine was added to a solution containing 1 g of N-tert-butoxycarbonyl-L-valine dissolved in 40 ml of methylene chloride, at −20° C. After the mixture was stirred for 15 minutes at the same temperature, 0.7 g of isobutyl chloroformate was added to the mixture, and stirred for 1 hour at −20° C. 1 g of 1-methyl-2-(4-nitrophenoxy)propylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was an oily substance, was purified by column chromatography on silica gel, thus yielding 1.1 g of the desired product in the form of yellow viscous liquid (yield: 56%).

Synthesis Example 7

Synthesis of $N^2$-tert-butoxycarbonyl-$N^1$-[2-(3,5-dimethoxyphenoxy)-1-methylethyl]-L-valinamide (Compound No. 22)

0.5 g of N-methylpiperidine was added to a solution containing 1.0 g of N-tert-butoxycarbonyl-L-valine dissolved in 100 ml of methylene chloride, at −20° C. After the mixture was stirred for 10 minutes at the same temperature, 0.7 g of isobutyl chloroformate was added to the mixture at −40° C., and then the whole mixture was stirred for 1 hour at −20° C. 1 g of 2-(3,5-dimethoxyphenoxy)-1-methylamine was added to this mixture at −60° C., and subsequently the reaction mixture was allowed to sit and warm naturally to room temperature while being stirred. The whole mixture was stirred for 15 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus yielding 1.3 g of the desired product in the form of white powder (yield: 64%).

Synthesis Example 8

Synthesis of $N^2$-tert-butoxycarbonyl-$N^1$-[1-methyl-2-(2,4,6-trichlorophenoxy)ethyl]-L-valinamide (Compound No. 25)

1.7 g of N-methylpiperidine was added to a solution containing 3.8 g of N-tert-butoxycarbonyl-L-valine dissolved in 80 ml of methylene chloride, at −20° C. After the mixture was stirred for 15 minutes at the same temperature, 2.4 g of isobutyl chloroformate was added to the mixture, and subsequently the whole mixture was stirred for 1 hour at −20° C. 4.5 g of 1-methyl-2-(2,4,6-trichlorophenoxy)ethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 4.6 g of the desired product in the form of a colorless needle crystal (yield: 58%).

Synthesis Example 9

Synthesis of $N^2$-isopropoxycarbonyl-$N^1$-[1-methyl-2-(4-nitrophenoxy)ethyl]-L-valinamide (Compound No. 45)

1.2 g of N-methylpiperidine was added to a solution containing 2.5 g of N-isopropoxycarbonyl-L-valine dissolved in 100 ml of methylene chloride, at −20° C. After the mixture was stirred for 10 minutes at the same temperature, 1.7 g of isobutyl chloroformate was added to the mixture, and subsequently the whole mixture was stirred for 1 hour at −20° C. 2.2 g of 2-(4-nitrophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 0.3 g of the desired product in the form of a yellow vitrified substance (yield: 6%).

| $^1$H-NMR: | (CDCl$_3$, δ) | |
|---|---|---|
| | 1.16 ~ 1.33 | (6H, m) |
| | 1.43 ~ 1.36 | (9H, m) |
| | 2.56 | (1H, m) |
| | 4.01 | (2H, m) |
| | 4.00 ~ 5.33 | (3H, m) |
| | 6.17 | (1H, d) |
| | 6.87 | (2H, d) |
| | 8.06 | (2H, d) |

Synthesis Example 10

Synthesis of $N^1$-[2-(4-cyanophenoxy)-1-methylethyl]-$N^2$-cyclohexyloxycarbonyl-L-valinamide (Compound No. 97)

0.8 g of N-methylpiperidine was added to a solution containing 2.0 g of N-cyclohexyloxycarbonyl-L-valine dissolved in 150 ml of methylene chloride, at −20° C. After the mixture was stirred for 10 minutes at the same temperature, 1.1 g of isobutyl chloroformate was added to the mixture, and subsequently the whole mixture was stirred for 1 hour at −20° C. 1.5 g of 2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 0.5 g of the desired product in the form of light brown powder (yield: 16%).

Synthesis Example 11

Synthesis of $N^1$-[1-methyl-2-(4-trifluoromethylphenoxy)ethyl]-$N^2$-phenoxycarbonyl-L-valinamide (Compound No. 114)

1.6 g of N-methylpiperidine was added to a solution containing 4.0 g of N-phenoxycarbonyl-L-valine dissolved in 80 ml of methylene chloride, at −20° C. After the mixture was stirred for 15 minutes at the same temperature, 2.2 g of isobutyl chloroformate was added to the mixture, and subsequently the whole mixture was stirred for 1 hour at −20° C. 3.5 g of 1-methyl-2-(4-trifluoromethylphenoxy) ethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 2.8 g of the desired product in the form of a white crystal (yield: 40%).

Synthesis Example 12

Synthesis of $N^1$-[1-methyl-2-(4-trifluoromethoxyphenoxy)ethyl]-$N^2$-phenoxycarbonyl-L-valinamide (Compound No. 115)

1.7 g of N-methylpiperidine was added to a solution containing 4.0 g of N-phenoxycarbonyl-L-valine dissolved in 80 ml of methylene chloride, at −20° C. After the mixture was stirred for 15 minutes at the same temperature, 2.3 g of isobutyl chloroformate was added to the mixture, and subsequently the whole mixture was stirred for 1 hour at −20° C.

4.0 g of 1-methyl-2-(4-trifluoromethoxyphenoxy) ethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 3.4 g of the desired product in the form of a white crystal (yield: 45%).

Synthesis Example 13

Synthesis of $N^1$-[2-(4-cyanophenoxy)-1-methylethyl]-$N^2$-phenoxycarbonyl-L-valinamide (Compound Nos. 116 and 117)

1.8 g of N-methylpiperidine was added to a solution containing 4.2 g of N-phenoxycarbonyl-L-valine dissolved in 100 ml of methylene chloride, at −20° C. After the mixture was stirred for 10 minutes at the same temperature, 2.4 g of isobutyl chloroformate was added to the mixture, and subsequently the whole mixture was stirred for 1 hour at −20° C. 3.1 g of 2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus obtaining 1.0 g of a white powder. 0.6 g of the obtained white powder was purified using high pressure liquid chromatography (hereinafter, referred to as "HPLC") (YMC-063-15, hexane/ethyl acetate=55/45) to separate two fractions. The ingredient of the first fraction having a short retention time was 0.3 g of a white powder (yield: 7%) having a melting point of 145° to 147° C. and the ingredient of the second fraction having a long retention time was 0.3 g of a white powder (yield: 7%) having a melting point of 166° to 170° C.

Synthesis Example 14

Synthesis of $N^1$-[2-(4-cyanophenoxy)-1-methylethyl]-$N^2$-(3-methoxyphenoxycarbonyl)-L-valinamide (Compound No. 166)

1.0 g of N-methylmorpholine was added to a solution containing 1.5 g of $N^1$-[2-(4-cyanophenoxy)-1-methylethyl]-L-valinamide hydrochloride dissolved in 100 ml of methylene chloride, at −20° C. After 0.9 g of 3-methoxyphenyl chloroformate was added to the mixture at −20° C., the reaction mixture was allowed to sit and warm naturally to room temperature while being stirred. The whole mixture was stirred for 2 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus yielding 0.25 g of the desired product in the form of a white plated crystal (yield: 12%).

Synthesis Example 15

Synthesis of $N^2$-(2-chloroethoxycarbonyl)-$N^1$-[2-(4-cyanophenoxy)-1-methylethyl]-L-valinamide (Compound No. 184)

0.5 g of N-methylpiperidine was added to a solution containing 1.1 g of N-(2-chloroethoxycarbonyl)-L-valine dissolved in 40 ml of methylene chloride, at −20° C. After the mixture was stirred for 15 minutes at the same temperature, 0.7 g of isobutyl chloroformate was added to the mixture at −40° C., and subsequently the whole mixture was stirred for 1 hour at −20° C. 0.9 g of 2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was an oily substance, was purified by column chromatography on silica gel, thus yielding 1.0 g of the desired product in the form of colorless grains (yield: 52%).

Synthesis Example 16

Synthesis of $N^1$-[2-(4-cyanophenoxy)-1-methylethyl]-$N^2$-(4-methylbenzyloxycarbonyl)-L-valinamide (Compound No. 195)

0.6 g of N-methylpiperidine was added to a solution containing 1.5 g of N-(4-methylbenzyloxycarbonyl)-L-valine dissolved in 100 ml of methylene chloride, at −20° C. After the mixture was stirred for 10 minutes at the same temperature, 0.8 g of isobutyl chloroformate was added to the mixture, and subsequently the whole mixture was stirred for 1 hour at −20° C. 1.0 g of 2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue, which was a crude crystal, was purified by column chromatography on silica gel, thus yielding 0.6 g of the desired product in the form of light white powder (yield: 28%).

Synthesis Example 17

Synthesis of $N^1$-[2-(4-cyanophenoxy)-1-methylethyl]-$N^2$-phenoxythiocarbonyl-L-valinamide (Compound No. 208)

0.4 g of N-methylmorpholine was added to a suspension containing 1.1 g of $N^1$-[2-(4-cyanophenoxy)-1-methylethyl]-L-valinamide suspended in 40 ml of methylene chloride, at −15° C. After 0.7 g of phenyl chlorothionoformate was added to the mixture at −15° C., the reaction mixture was allowed to sit and warm naturally to room temperature while being stirred, and then the whole mixture was stirred for 15 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus yielding 1.2 g of the desired product in the form of a yellow glutinous substance (yield: 75%).

| $^1$H-NMR: | (CDCl$_3$, δ) | |
|---|---|---|
| | 1.05 | (6H, m) |
| | 1.35 | (3H, m) |
| | 2.30 | (1H, m) |
| | 4.00 | (2H, m) |
| | 4.44 | (1H, m) |
| | 4.54 | (1H, m) |
| | 6.16, 6.25 | (1H, d) |
| | 7.26 | (9H, m) |
| | 7.51 | (1H, br) |

Synthesis Example 18

Synthesis of $N^1$-[2-(4-cyanophenoxy)-1-methylethyl]-$N^2$-(phenylthio)thiocarbonyl-L-valinamide (Compound No. 211)

0.5 g of N-methylmorpholine was added to a suspension containing 1.4 g of $N^1$-[2-(4-cyanophenoxy)-1-methylethyl]-L-valinamide suspended in 40 ml of methylene chloride, at −15° C. After 0.9 g of phenyl chlorodithioformate was added to the mixture at −15° C., the reaction mixture was allowed to sit and warm naturally to room temperature while being stirred, and subsequently the whole mixture was stirred for 15 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus yielding 1.4 g of the desired product in the form of a yellow glutinous substance (yield: 66%).

| $^1$H-NMR: | (CDCl$_3$, δ) | |
|---|---|---|
| | 0.83 | (6H, m) |
| | 1.30, 1.32 | (3H, d) |
| | 2.13 | (1H, m) |
| | 3.96 | (2H, m) |
| | 4.35 | (1H, m) |
| | 4.78 | (1H, dd) |
| | 6.04, 6.13 | (1H, d) |
| | 6.93, 6.98 | (2H, d) |
| | 7.15, 7.22 | (1H, d) |
| | 7.57 | (7H, m) |

Synthesis Example 19

Synthesis of $N^1$-(1-methyl-2-phenylthioethyl)-$N^2$-phenoxycarbonyl-L-valinamide (Compound No. 212)

1.3 g of N-methylmorpholine was added to a suspension containing 3.0 g of $N^1$-(1-methyl-2-phenylthioethyl)-L-valinamide hydrochloride suspended in 80 ml of methylene chloride, at −15° C. After 1.9 g of phenyl chloroformate was added to the mixture at −15° C., the reaction mixture was allowed to sit and warm naturally to room temperature while being stirred, and subsequently the whole mixture was stirred for 15 hours at room temperature. Water was subsequently added to the reaction mixture. After the methylene chloride layer was washed with water, the organic layer was dried over anhydrous magnesium sulfate and the methylene chloride was removed under reduced pressure. The residue was purified by column chromatography on silica gel, thus yielding 2.3 g of the desired product in the form of a white crystal (yield: 54%).

Synthesis Example 20

Synthesis of $N^1$-[2-(4-chloroanilino)-1-methylethyl]-$N^2$-isopropoxycarbonyl-L-valinamide (Compound No. 221)

1.9 g of N-methylpiperidine was added to a solution containing 3.8 g of N-isopropoxycarbonyl-L-valine dissolved in 80 ml of methylene chloride, at −20° C. After the mixture was stirred for 15 minutes at the same temperature, 2.6 g of isobutyl chloroformate was added to the mixture, and subsequently the whole mixture was stirred for 1 hour at −20° C. 3.5 g of 2-(4-chloroanilino)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 3.3 g of the desired product in the form of a white crystal (yield: 47%).

Synthesis Example 21

Synthesis of 2-tert-butoxycarbonylamino-N-[2-(4-chlorophenoxy)-1-methylethyl]-(2S)-butyramide (Compound No. 233)

2.0 g of N-methylpiperidine was added to a solution containing 4.1 g of (2S)-2-tert-butoxycarbonylaminobutyric acid dissolved in 60 ml of methylene chloride, at −20° C. After the mixture was stirred for 10 minutes at the same temperature, 2.7 g of isobutyl chloroformate was added to the mixture at −40° C., and subsequently the whole mixture was stirred for 1 hour at −20° C. After 3.7 g of 2-(4-chlorophenoxy)-1-methylethylamine was added to this mixture at −60° C., the reaction mixture was allowed to sit and warm naturally to room temperature while being stirred, and subsequently stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 5.6 g of the desired product in the form of a colorless glutinous substance (yield: 76%).

Synthesis Example 22

Synthesis of 2-tert-butoxycarbonylamino-N-[2-(4-cyanophenoxy)-1-methylethyl]-(2S)-butyramide (Compound No. 235)

0.5 g of N-methylpiperidine was added to a solution containing 1.0 g of (2S)-2-tert-butoxycarbonylaminobutyric acid dissolved in 40 ml of methylene chloride, at −20° C. After the mixture was stirred for 10 minutes at the same temperature, 0.7 g of isobutyl chloroformate was added to the mixture at −20° C., and subsequently the whole mixture was stirred for 1 hour at −20° C. 0.9 g of 2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 1.0 g of the desired product in the form of a glutinous substance (yield: 54%).

| $^1$H-NMR: | (CDCl$_3$, δ) |
|---|---|
| 0.94 | (3H, t) |
| 1.20 ~ 1.50 | (12H, m) |
| 1.69 | (2H, m) |
| 3.83 ~ 4.56 | (4H, m) |
| 5.30 | (1H, d) |
| 6.60 | (1H, m) |
| 6.90 | (2H, d) |
| 7.50 | (2H, d) |

SYNTHESIS EXAMPLE 23

Synthesis of $N^1$-[2-(4-chlorobenzyloxy)-1-methylethyl]-$N^2$-isopropoxycarbonyl-L-valinamide (Compound No. 246)

0.5 g of N-methylpiperidine was added to a solution containing 1 g of N-isopropoxycarbonyl-L-valine dissolved in 40 ml of methylene chloride, at −720° C. After the mixture was stirred for 15 minutes at the same temperature, 0.7 g of isobutyl chloroformate was added to the mixture at −40° C., and subsequently the whole mixture was stirred for 1 hour at −20° C. 1 g of 2-(4-chlorobenzyloxy)-1-methylethylamine was added to this mixture at −60° C., and then the reaction mixture was allowed to sit and warm naturally to room temperature while being stirred. The whole mixture was stirred for, 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained oily residue was purified by column chromatography on silica gel, thus yielding 0.9 g of the desired product in the form of a colorless plated crystal (yield: 48%).

SYNTHESIS EXAMPLE 24

Synthesis of $N^2$-tert-butoxycarbonyl-$N^1$-[1-methyl-2-(4-methylthiophenoxy)ethyl]-L-valinamide (Compound No. 327)

3.4 g of N-methylpiperidine was added to a solution containing 7.5 g of N-tert-butoxycarbonyl-L-valine dissolved in 100 ml of methylene chloride, at −20° C. After the mixture was stirred for 10 minutes at the same temperature, 4.7 g of isobutyl chloroformate was added to the mixture, and subsequently the whole mixture was stirred for 1 hour at −20° C. 6.8 g of 1-methyl-2-(4-methylthiophenoxy)ethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained oily residue was purified by column chromatography on silica gel, thus yielding 6.2 g of the desired product in the form of a colorless prism-shaped crystal (yield: 46%).

SYNTHESIS EXAMPLE 25

Synthesis of $N^2$-tert-butoxycarbonyl-$N^1$-1-methyl-2-(4-methylsulfinylphenoxy)ethyl]-L-valinamide (Compound No. 328)

1.5 g of m-chloroperbenzoic acid was added to a solution containing 3.0 g of $N^2$-tert-butoxycarbonyl-$N^1$-[1-methyl-2-(4-methylthiophenoxy)ethyl]-L-valinamide dissolved in 60 ml of methylene chloride, at 0° C. After the mixture was stirred for 5 hours at room temperature, the reaction mixture was filtered. The filtrate was washed successively with a saturated aqueous solution of potassium carbonate and water, the organic layer was dried over anhydrous sodium sulfate and the methylene chloride was removed under reduced pressure. The obtained oily residue was purified by column chromatography on silica gel, thus yielding 1.7 g of the desired product in the form of a colorless crystal (yield: 56%).

SYNTHESIS EXAMPLE 26

Synthesis of $N^2$-tert-butoxycarbonyl-$N^1$-[1-methyl-2-(4-methylsulfonylphenoxy)ethyl]-L-valinamide (Compound No. 329)

2.1 g of m-chloroperbenzoic acid was added to a solution containing 2.0 g of $N^2$-tert-butoxycarbonyl-$N^1$-[1-methyl-2-(4-methylthiophenoxy)ethyl]-L-valinamide dissolved in 50 ml of methylene chloride, at 0° C. After the mixture was stirred for 8 hours at a reflux temperature, the reaction mixture was allowed to sit and cool naturally to room temperature and filtered. The filtrate was washed successively with a saturated aqueous solution of potassium carbonate and water, the organic layer was dried over anhydrous sodium sulfate and the methylene chloride was removed under reduced pressure. The obtained residue was purified by column chromatography on silica gel, thus yielding 1.3 g of the desired product in the form of a colorless prism-shaped crystal (yield: 60%).

SYNTHESIS EXAMPLE 27

Synthesis of $N^1$-[2-(4-fluorophenylsulfinyl)-1-methylethyl]-$N^2$-isopropoxycarbonyl-L-valinamide (Compound No. 354)

1.3 g of-m-chloroperbenzoic acid was added to a solution containing 2.5 g of $N^1$-[2-(4-fluorophenylthio)-1-methylethyl]-$N^2$-isopropoxycarbonyl-L-valinamide dissolved in 50 ml of methylene chloride, at 0° C. After the mixture was stirred for 5 hours at room temperature, the reaction mixture was filtered. The filtrate was washed successively with a saturated aqueous solution of potassium carbonate and water, the organic layer was dried over anhydrous sodium sulfate and the methylene chloride was removed under reduced pressure. The obtained residue was purified by column chromatography on silica gel, thus yielding 1.8 g of the desired product in the form of a colorless prism-shaped crystal (yield: 69%).

SYNTHESIS EXAMPLE 28

Synthesis of $N^1$-[2-(4-fluorophenylsulfonyl)-1-methylethyl]-$N^2$-isopropoxycarbonyl-L-valinamide (Compound No. 355)

3.4 g of m-chloroperbenzoic acid was added to a solution containing 2.2 g of $N^1$-[2-(4-fluorophenylthio)-1-methylethyl]-$N^2$-isopropoxycarbonyl-L-valinamide dissolved in 50 ml of methylene chloride, at 0° C. After the mixture was stirred for 8 hours at a reflux temperature, the reaction mixture was allowed to sit and cool to room temperature, and then filtered. The filtrate was washed successively with a saturated aqueous solution of potassium carbonate and water, the organic layer was dried over anhydrous sodium sulfate and the methylene chloride was removed under reduced pressure. The obtained residue was purified by column chromatography on silica gel, thus yielding 2.0 g of the desired product in the form of a white crystal (yield: 83%).

SYNTHESIS EXAMPLE 29

Synthesis of $N^2$-isopropoxycarbonyl-$N^1$-[1-methyl-2-(2-methylphenylthio)ethyl]-L-valinamide (Compound No. 367)

1.9 g of N-methylpiperidine was added to a solution containing 3.9 g of N-isopropoxycarbonyl-L-valine dissolved in 80 ml of methylene chloride, at −20° C. After the mixture was stirred for 10 minutes at the same temperature, 2.6 g of isobutyl chloroformate was added to the mixture, and subsequently the whole mixture was stirred for 1 hour at −20° C. 3.5 g of 1-methyl-2-(2-methylphenylthio) ethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over an hydrous sodium sulfate and the methylene chloride was removed under reduced pressure. The residue was purified by column chromatography on silica gel, thus yielding 3.6 g of the desired product in the form of a white crystal (yield: 51%).

SYNTHESIS EXAMPLE 30

Synthesis of $N^1$-[2-(4-cyanophenoxy)-1-methylethyl]-$N^2$-(3-tetrahydrofuranyl)oxycarbonyl-L-valinamide (Compound No. 376)

1.0 g of N-methylmorpholine, and subsequently 0.7 g of 3-tetrahydrofuranyl chloroformate were added to a suspension containing 1.5 g of $N^1$-[2-(4-cyanophenoxy)-1-methylethyl]-L-valinamide hydrochloride suspended in 100 ml of methylene chloride at −20° C. The mixture was allowed to sit and warm naturally to room temperature and then stirred for 2 hours at room temperature. Water was subsequently added to the reaction mixture. After the dichloromethane layer was washed with water, the organic layer was dried over anhydrous magnesium sulfate and then the methylene chloride was removed under reduced pressure. The residue was purified by column chromatography on silica gel, thus yielding 1.1 g of the desired product in the form of white powder (yield: 61%).

SYNTHESIS EXAMPLE 31

Synthesis of $N^1$-[2-(4-cyanophenoxy)-1-methylethyl]-$N^2$-(3-methylcyclohexyloxycarbonyl)-L-valinamide (Compound No. 379)

0.4 g of N-methylmorpholine, and subsequently 0.8 g of 3-methylcyclohexyl chloroformate were added to a suspension containing 1.0 g of $N^1$-[2-(4-cyanophenoxy)-1-methylethyl]-L-valinamide suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.2 g of the desired product in the form of a white crystal (yield: 80%).

SYNTHESIS EXAMPLE 32

Synthesis of $N^1$-[2-(4-cyanophenoxy)-1-methylethyl]-$N^2$-propargyloxycarbonyl-L-valinamide (Compound No. 381)

0.2 g of N-methylmorpholine, and subsequently 0.2 g of propargyl chloroformate were added to a suspension containing 0.5 g of $N^1$-[2-(4-cyanophenoxy)-1-methylethyl]-L-valinamide suspended in 30 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.5 g of the desired product in the form of white powder (yield: 78%).

SYNTHESIS EXAMPLE 33

Synthesis of $N^1$-[2-(4-cyanophenoxy)-1-methylethyl]-$N^2$-(2-methoxy-1-methylethyl)oxycarbonyl-L-valinamide (Compound No. 383)

1.0 g of N-methylmorpholine, and subsequently 0.7 g of 2-methoxy-1-methylethyl chloroformate were added to a suspension containing 1.5 g of $N^1$-[2-(4-cyanophenoxy)-1-methylethyl]-L-valinamide suspended in 150 ml of methylene chloride at −20° C. The mixture was allowed to sit and warm naturally to room temperature and then stirred for 2 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.37 g of the desired product in the form of a white plated crystal (yield: 20%).

SYNTHESIS EXAMPLE 34

Synthesis of $N^1$-[2-(4-fluoro-N-methylanilino)-1-methylethyl]-$N^2$-phenoxycarbonyl-L-valinamide (Compound No. 391)

1.6 g of N-methylpiperidine was added to a solution containing 3.9 g of N-phenoxycarbonyl-L-valine dissolved in 80 ml of methylene chloride, at −20° C. After the mixture was stirred for 10 minutes at the same temperature, 2.2 g of isobutyl chloroformate was added to the mixture, and subsequently the whole mixture was stirred for 1 hour at −20° C. 3.0 g of 2-(4-fluoro-N-methylanilino)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus yielding 1.2 g of the desired product in the form of a white crystal (yield: 19%).

SYNTHESIS EXAMPLE 35

Synthesis of $N^2$-(4-chlorophenoxycarbonyl)-$N^1$-[2-(4-cyanophenoxy-1-methylethyl]-L-valinamide (Compound Nos. 395 and 396)

1.7 g of N-methylpiperidine was added to a solution containing 4.7 g of N-(4-chlorophenoxycarbonyl)-L-valine dissolved in 250 ml of methylene chloride, at −20° C. After the mixture was stirred for 10 minutes at the same temperature, 2.3 g of isobutyl chloroformate was added to the mixture, and subsequently the whole mixture was stirred for 1 hour at −20° C. 3.0 g of 2-(4-cyanophenoxy)-1-methylethylamine was added to this mixture at −60° C., and then the reaction mixture was allowed to sit and warm naturally to room temperature while being stirred. The whole mixture was stirred for 15 hours at room temperature. Water was subsequently added to the reaction mixture. After the methylene chloride layer was washed successively with a 5% aqueous solution of sodium bicarbonate and water, the organic layer was dried over anhydrous, magnesium sulfate and the methylene chloride was removed under reduced pressure. The obtained crude crystal was purified by column chromatography on silica gel, thus yielding 0.4 g of the desired product in the form of white powder. In addition, the powder was purified by HPLC (YMC-063-15, hexane/ethyl acetate=55/45) to separate two fractions. One fraction having a short retention time was 0.17 g of white powder having a melting point of 137°~140° C. (yield: 2%), and another fraction having a long retention time was 0.17 g of white powder having a melting point of 174°~179° C. (yield: 2%).

SYNTHESIS EXAMPLE 36

Synthesis of $N^1$-[2-(4-cyanophenoxy)-1-methylethyl]-$N^2$-(2-nitrophenoxycarbonyl-L-valinamide (Compound No. 400)

1.3 g of N-methylmorpholine, and subsequently 2.5 g of 2-nitrophenyl chloroformate were added to a suspension containing 3.4 g of $N^1$-[2-(4-cyanophenoxy)-1-methylethyl]-L-valinamide suspended in 100 ml of methylene chloride at −20° C. The mixture was allowed to sit and warm naturally to room temperature and then stirred for 2 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus obtaining 1.0 g of the desired product in the form of a yellow plated crystal (yield: 18%).

SYNTHESIS EXAMPLE 37

Synthesis of $N^1$-[2-(4-cyanophenoxy)-1-methylethyl]-$N^2$-(4-fluorophenoxycarbonyl)-L-valinamide (Compound No. 401)

1.2 g of N-methylpiperidine was added to a solution containing 3.0 g of N-(4-fluorophenoxycarbonyl)-L-valine dissolved in 80 ml of methylene chloride, at −20° C. After the mixture was stirred for 15 minutes at the same temperature, 1.6 g of isobutyl chloroformate was added to the mixture, and subsequently the whole mixture was stirred for 1 hour at −20° C. 2.3 g of (−)-2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and subsequently the methylene chloride was removed under reduced pressure. The obtained crude crystal was purified by column chromatography on silica gel, thus yielding 1.1 g of the desired product in the form of a white crystal (yield: 23%).

SYNTHESIS EXAMPLE 38

Synthesis of $N^1$-[2-(4-cyanophenoxy)-1-methylethyl]-$N^2$-(3,4-dimethylphenoxycarbonyl)-L-valinamide (Compound No. 403)

0.6 g of N-methylmorpholine, and subsequently 1.2 g of 3,4-dimethylphenyl chloroformate were added to a suspension containing 1.5 g of $N^1$-[2-(4-cyanophenoxy)-1-methylethyl]-L-valinamide suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.7 g of the desired product in the form of a white crystal (yield: 74%).

SYNTHESIS EXAMPLE 39

Synthesis of $N^2$-tert-butoxycarbonyl-$N^1$-[2-(2-pyridyloxy)-1-methylethyl]-L-valinamide (Compound No. 409)

2.0 g of N-methylpiperidine was added to a solution containing 4.3 g of N-tert-butoxycarbonyl-L-valine dissolved in 80 ml of methylene chloride, at −20° C. After the mixture was stirred for 10 minutes at the same temperature, 2.7 g of isobutyl chloroformate was added to the mixture at −40° C., and subsequently the whole mixture was stirred for 1 hour at −20° C., 3.3 g of 2-(2-pyridyloxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained crude crystal was purified by column chromatography on silica gel, thus yielding 2.0 g of the desired product in the form of colorless grains (yield: 28%).

SYNTHESIS EXAMPLE 40

Synthesis of $N^1$-[2-(5-chloro-2-pyridyloxy)-1-methylethyl]-$N^2$-isopropyloxycarbonyl-L-valinamide (Compound No. 412)

0.8 g of N-methylmorpholine, and subsequently 0.5 g of isopropyl chloroformate were added to a suspension containing 1.4 g of $N^1$-[2-(5-chloro-2-pyridyloxy)-1-methylethyl]-L-valinamide hydrochloride suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.6 g of the desired product in the form of colorless grains (yield: 38%).

SYNTHESIS EXAMPLE 41

Synthesis of $N^1$-[2-(5-chloro-2-pyridyloxy)-1-methylethyl]-$N^2$-phenoxycarbonyl-L-valinamide (Compound No. 413)

0.8 g of N-methylmorpholine, and subsequently 0.7 g of phenyl chloroformate were added to a suspension containing 1.4 g of $N^1$-[2-(5-chloro-2-pyridyloxy)-1-methylethyl]-L-valinamide hydrochloride suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.6 g of the desired product in the form of colorless grains (yield: 34%).

SYNTHESIS EXAMPLE 42

Synthesis of $N^1$-[2-(4-fluoro-N-methylanilino)-1-methylethyl]-$N^2$-phenoxycarbonyl-L-isoleucinamide (Compound No. 422)

1.9 g of N-methylpiperidine was added to a solution containing 4.8 g of N-phenoxycarbonyl-L-isoleucine dissolved in 80 ml of methylene chloride, at −20° C. After the mixture was stirred for 10 minutes at the same temperature, 2.6 g of isobutyl chloroformate was added to the mixture, and subsequently the whole mixture was stirred for 1 hour at −20° C. 3.5 g of 2-(4-fluoro-N-methylanilino)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and subsequently the methylene chloride was removed under reduced pressure. The obtained crude crystal was purified by column chromatography on silica gel, thus yielding 1.1 g of the desired product in the form of a white crystal (yield: 13%).

SYNTHESIS EXAMPLE 43

Synthesis of $N^2$-(ethylthio)carbonyl-$N^1$-[1-methyl-2-(4-nitrophenoxy)ethyl]-L-valinamide (Compound No. 432)

0.3 g of N-methylmorpholine, and subsequently 0.4 g of ethyl chlorothioformate were added to a suspension containing 0.9 g of $N^1$-[1-methyl-2-(4-nitrophenoxy)ethyl]-L-valinamide suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate, and then the methylene chloride was removed under reduced pressure. The residue was purified by column chromatography on silica gel, thus yielding 1.0 g of the desired product in the form of yellow grains (yield: 79%).

SYNTHESIS EXAMPLE 44

Synthesis of $N^2$-tert-butoxycarbonyl-$N^1$-[2-(4-cyanophenoxy)-1-methylethyl]-L-leucinamide (Compound No. 455)

1.5 g of N-methylpiperidine was added to a solution containing 3.4 g of N-tert-butoxycarbonyl-L-leucine dissolved in 60 ml of methylene chloride, at −20° C. After the mixture was stirred for 10 minutes at the same temperature, 2.0 g of isobutyl chloroformate was added to the mixture at −40° C., and subsequently the whole mixture was stirred for 1 hour at −20° C. 2.6 g of 2-(4-cyanophenoxy)-1-methylethylamine was added to this mixture at −60° C., and then the reaction mixture was allowed to sit and warm naturally to room temperature while being stirred. The whole mixture was stirred for 15 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 5.1 g of the desired product in the form of a colorless glutinous substance (yield: 86%).

| $^1$H-NMR: | (CDCl$_3$, δ) |  |
|---|---|---|
| | 0.92 | (6H, m) |
| | 1.28, 1.32 | (3H, d) |
| | 1.39, 1.43 | (9H, s) |
| | 1.46, 1.65 | (2H, m) |
| | 1.65 | (1H, m) |
| | 3.98 | (2H, m) |
| | 4.06 | (1H, m) |
| | 4.35 | (1H, m) |
| | 4.91 | (1H, br) |
| | 6.46 | (1H, br) |
| | 6.97 | (2H, d) |
| | 7.57 | (2H, dd) |

SYNTHESIS EXAMPLE 45

Synthesis of $N^2$-tert-butoxycarbonyl-$N^1$-[2-(4-cyanophenoxy)-1-methylethyl]-L-tert-leucinamide (Compound No. 457)

1.7 g of N-methylpiperidine was added to a solution containing 4 g of N-tert-butoxycarbonyl-L-tert-leucine dissolved in 50 ml of methylene chloride, at −20° C. After the mixture was stirred for 10 minutes at the same temperature, 2.4 g of isobutyl chloroformate was added to the mixture at −40° C., and subsequently the whole mixture was stirred for 1 hour at −20° C. 3.1 g of 2-(4-cyanophenoxy)-1-methylethylamine was added to this mixture at −60° C., and then the reaction mixture was allowed to sit and warm naturally to room temperature while being stirred. The whole mixture was stirred for 15 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 3.9 g of the desired product in the form of a colorless amorphous substance (yield: 58%).

SYNTHESIS EXAMPLE 46

Synthesis of 2-tert-butoxycarbonylamino-3-methyl-N-[2-(4-cyanophenoxy)-1-methylethyl]-3-butenic acid amide (Compound No. 460)

0.5 g of N-methylpiperidine was added to a solution containing 1.1 g of 2-tert-butoxycarbonylamino-3-methyl-3-butenic acid dissolved in 40 ml of methylene chloride, at −20° C. After the mixture was stirred for 10 minutes at the same temperature, 0.7 g of isobutyl chloroformate was added to the mixture at −40° C., and subsequently the whole mixture was stirred for 1 hour at −20° C. 1.9 g of 2-(4-cyanophenoxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 0.3 g of the desired product in the form of a colorless glutinous substance (yield: 32%).

SYNTHESIS EXAMPLE 47

Synthesis of N-[2-(4-cyanophenoxy)-1-methylethyl]-2-isopropoxycarbonylaminocyclopentylacetic acid amide (Compound No. 462)

0.4 g of N-methylmorpholine, and subsequently 0.5 g of isopropyl chloroformate were added to a suspension containing 1.2 g of 2-amino-N-[2-(4-cyanophenoxy)-1-methylethyl]cyclopentylacetic acid amide suspended in 40 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.4 g of the desired product in the form of a colorless plated crystal (yield: 90%).

SYNTHESIS EXAMPLE 48

Synthesis of $N^1$-[2-(4-cyanophenoxy)-1-methylethyl]-$N^2$-phenoxycarbonyl-L-norvalinamide (Compound No. 465)

0.5 g of N-methylmorpholine, and subsequently 0.8 g of phenyl chloroformate were added to a suspension containing 1.4 g of $N^1$-[2-(4-cyanophenoxy)-1-methylethyl]-L-norvalinamide suspended in 40 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.1 g of the desired product in the form of a colorless plated crystal (yield: 57%)

SYNTHESIS EXAMPLE 49

Synthesis of $N^1$-[2-(4-cyanophenoxy)-1-methylethyl]-$N^2$-phenoxycarbonyl-L-leucinamide (Compound No. 466)

0.5 g of N-methylmorpholine, and subsequently 0.8 g of phenyl chloroformate were added to a suspension containing 1.5 g of $N^1$-[2-(4-cyanophenoxy)-1-methylethyl]-L-leucinamide suspended in 40 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.5 g of the desired product in the form of colorless powder (yield: 73%).

SYNTHESIS EXAMPLE 50

Synthesis of 2-(4-chlorophenoxycarbonylamino)-N-[2-(4-cyanophenoxy)-1-methylethyl]cyclopentylacetic acid amide (Compound No. 471)

0.4 g of N-methylmorpholine, and subsequently 0.8 g of 4-chlorophenyl chloroformate were added to a suspension containing 1.2 g of 2-amino-N-[2-(4-cyanophenoxy)-1-methylethyl]cyclopentylacetic acid amide suspended in 40 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.6 g of the desired product in the form of colorless grains (yield: 30%).

SYNTHESIS EXAMPLE 51

Synthesis of $N^2$-benzyloxycarbonyl-$N^1$-[2-(4-cyanophenoxy)-1-methylethyl]-(4-chlorophenyl)glycinamide (Compound No. 475)

0.4 g of N-methylmorpholine, and subsequently 0.6 g of benzyl chloroformate were added to a suspension containing 1.3 g of $N^1$-[2-(4-cyanophenoxy)-1-methylethyl]-(4-chlorophenyl)glycinamide suspended in 40 ml of methylene chloride at −1 5° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.2 g of the desired product in the form of colorless grains (yield: 70%).

SYNTHESIS EXAMPLE 52

Synthesis of $N^2$-(1-cyano-1-methylethoxycarbonyl)-$N^1$-[2-(4-cyanophenoxy)-1-methylethyl]-L-valinamide (Compound No. 476)

0.5 g of N-methylmorpholine, and subsequently 0.4 g of 1-cyano-1-methylethyl chloroformate were added to a suspension containing 0.7 g of $N^1$-[2-(4-cyanophenoxy)-1-methylethyl]-L-valinamide hydrochloride suspended in 50 ml of methylene chloride at −20° C. The mixture was allowed to sit and warm naturally to room temperature and then stirred for 3 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.6 g of the desired product in the form of colorless grains (yield: 71%).

SYNTHESIS EXAMPLE 53

Synthesis of $N^2$-(2-chlorocyclohexyloxycarbonyl)-$N^1$-[2-(4-cyanophenoxy)-1-methylethyl]-L-valinamide (Compound No. 477)

0.4 g of N-methylmorpholine, and subsequently 0.9 g of 2-chlorocyclohexyl chloroformate were added to a suspension containing 1.0 g of $N^1$-[2-(4-cyanophenoxy)-1-methylethyl]-L-valinamide hydrochloride suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.1 g of the desired product in the form of a white crystal (yield: 71%).

SYNTHESIS EXAMPLE 54

Synthesis of $N^2$-tert-butoxycarbonyl-$N^1$-[2-(3-chloro-5-trifluoromethyl-2-pyridyloxy)-1-methylethyl]-L-valinamide (Compound No. 479)

2.0 g of N-methylpiperidine was added to a solution containing 5.6 g of N-tert-butoxycarbonyl-L-valine dissolved in 100 ml of methylene chloride, at −20° C. After the mixture was stirred for 10 minutes at the same temperature, 2.7 g of isobutyl chloroformate was added to the mixture at −40° C., and subsequently the whole mixture was stirred for 1 hour at −20° C. 1.5 g of 2-(3-chloro-5-trifluoromethyl-2-pyridyloxy)-1-methylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The obtained crude crystal was purified by column chromatography on silica gel, thus yielding 7.0 g of the desired product in the form of colorless grains (yield: 77%).

SYNTHESIS EXAMPLE 55

Synthesis of $N^1$-[1-(5-chloro-6-ethyl-4-pyrimidinyloxy)-2-propyl]-$N^2$-isopropoxycarbonyl-L-valinamide (Compound No. 481)

0.34 g of N-methylpiperidine was added to a solution containing 0.7 g of N-isopropoxycarbonyl-L-valine dissolved in 50 ml of methylene chloride, at −20° C. After the mixture was stirred for 10 minutes at the same temperature, 0.47 g of isobutyl chloroformate was added to the mixture, and subsequently the whole mixture was stirred for 1 hour at −20° C. 0.74 g of 1-(5-chloro-6-ethyl-4-pyrimidinyloxy)-2-propylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 0.6 g of the desired product in the form of a white prism-shaped crystal (yield: 43%).

SYNTHESIS EXAMPLE 56

Synthesis of N-tert-butoxycarbonyl-L-valyl-N-(4-chlorophenyl)-N-methyl-DL-alaninamide (Compound No. 490)

0.9 g of N-methylpiperidine was added to a solution containing 2.0 g of N-tert-butoxycarbonyl-L-valine dissolved in 40 ml of methylene chloride, at −20° C. After the mixture was stirred for 10 minutes at the same temperature, 1.3 g of isobutyl chloroformate was added to the mixture, and subsequently the whole mixture was stirred for 1 hour at −20° C. 2.0 g of $N^1$-(4-chlorophenyl)-$N^1$-methyl-DL-alaninamide was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 3.4 g of the desired product in the form of a colorless needle crystal (yield: 87%).

SYNTHESIS EXAMPLE 57

Synthesis of N-isopropoxycarbonyl-L-isoleucyl-N-(4-cyanophenyl)-D-alaninamide (Compound No. 506)

0.26 g of N-methylpiperidine was added to a solution containing 0.57 g of N-isopropoxycarbonyl-L-isoleucine dissolved in 60 ml of methylene chloride, at −20° C. After the mixture was stirred for 10 minutes at the same temperature, 0.36 g of isobutyl chloroformate was added to the mixture, and subsequently the whole mixture was stirred for 1 hour at −20° C. 0.5 g of $N^1$-(4-cyanophenyl)-D-alaninamide was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus yielding 0.5 g of the desired product in the form of white powder (yield: 49%).

SYNTHESIS EXAMPLE 58

Synthesis of N-cyclohexyloxycarbonyl-L-valyl-N-(4-cyanophenyl)-D-alaninamide (Compound No. 509)

0.6 g of N-methylmorpholine, and subsequently 0.6 g of cyclopentyl chloroformate were added to a suspension containing 1.0 g of L-valyl-N-(4-cyanophenyl)alaninamide, hydrochloride suspended in 50 ml of methylene chloride at −20° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.6 g of the desired product in the form of a white crystal (yield: 49%).

SYNTHESIS EXAMPLE 59

Synthesis of N-phenoxycarbonyl-L-valyl-N-(4-chlorobenzyl)-DL-alaninamide (Compound No. 516)

0.55 g of N-methylmorpholine, and subsequently 0.43 g of phenyl chloroformate were added to a suspension containing 0.95 g of L-valyl-N-(4-chlorobenzyl)-DL-alaninamide hydrochloride suspended in 50 ml of methylene chloride at −15° C. The mixture was allowed to sit and warm naturally to room temperature and then stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.9 g of the desired product in the form of white powder (yield: 75%).

SYNTHESIS EXAMPLE 60

Synthesis of N-phenoxycarbonyl-L-valyl-DL-alanine phenyl ester (Compound No. 522)

0.24 g of N-methylpiperidine was added to a solution containing 0.57 g of N-phenoxycarbonyl-L-valine dissolved in 40 ml of methylene chloride, at −20° C. After the mixture was stirred for 10 minutes at the same temperature, 0.33 g of isobutyl chloroformate was added to the mixture, and subsequently the whole mixture was stirred for 1 hour at −20° C. 0.5 g of DL-alanine phenyl ester was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 0.2 g of the desired product in the form of white powder (yield: 20%).

SYNTHESIS EXAMPLE 61

Synthesis of $N^1$-(4-cyanophenyl)-$N^2$-(2-phenoxycarbonylamino)-(2S)-butyryl-D-alaninamide (Compound No. 524)

0.45 g of N-methylpiperidine was added to a solution containing 1.0 g of (2S)-2-phenoxycarbonylaminobutyric acid dissolved in 50 ml of methylene chloride, at −20° C. After the mixture was stirred for 10 minutes at the same temperature, 0.61 g of isobutyl chloroformate was added to the mixture, and subsequently the whole mixture was stirred for 1 hour at −20° C. 0.85 g of $N^1$-(4-cyanophenyl)-D-alaninamide was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained crude crystal was purified by column chromatography on silica gel, thus yielding 0.8 g of the desired product in the form of white powder (yield: 45%).

SYNTHESIS EXAMPLE 62

Synthesis of N-isopropoxycarbonyl-L-valyl-N-(4-cyanophenyl)glycinamide (Compound No. 526)

0.3 g of N-methylpiperidine was added to a solution containing 0.6 g of N-isopropoxycarbonyl-L-valine dissolved in 40 ml of methylene chloride, at −20° C. After the mixture was stirred for 10 minutes at the same temperature, 0.4 g of isobutyl chloroformate was added to the mixture, and subsequently the whole mixture was stirred for 1 hour at −20° C. 0.5 g of $N^1$-(4-cyanophenyl)glycinamide was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The residue was purified by column chromatography on silica gel, thus yielding 0.5 g of the desired product in the form of colorless powder (yield: 49%).

SYNTHESIS EXAMPLE 63

Synthesis of $N^2$-tert-butoxycarbonyl-$N^1$-(1,2-dimethyl-2-phenoxyethyl)-L-valinamide (Compound No. 602)

0.6 g of N-methylpiperidine was added to a solution containing 1.3 g of N-tert-butoxycarbonyl-L-valine dissolved in 40 ml of methylene chloride, at −20° C. After the mixture was stirred for 15 minutes at the same temperature, 0.8 g of isobutyl chloroformate was added to the mixture, and subsequently the whole mixture was stirred for 1 hour at −20° C. 1 g of 1,2-dimethyl-2-phenoxyethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous magnesium sulfate and the methylene chloride was removed under reduced pressure. The obtained oily substance was purified by column chromatography on silica gel, thus yielding 1.3 g of the desired product in the form of a white glutinous substance (yield: 57%).

| $^1$H-NMR: | (CDCl$_3$, δ) | |
|---|---|---|
| | 0.8 ~ 1.02 | (6H, m) |
| | 1.18 ~ 1.45 | (15H, m) |
| | 2.10 | (1H, m) |
| | 3.65 ~ 4.45 | (3H, m) |
| | 5.18 | (1H, m) |
| | 6.38 | (1H, m) |
| | 6.72 ~ 7.35 | (5H, m) |

SYNTHESIS EXAMPLE 64

Synthesis of $N^2$-tert-butoxycarbonyl-$N^1$-[2-(4-cyanophenoxy)-1,2-dimethylethyl]-L-valinamide (Compound No. 607)

0.5 g of N-methylpiperidine was added to a solution containing 1.1 g of N-tert-butoxycarbonyl-L-valine dissolved in 60 ml of methylene chloride, at −20° C. After the mixture was stirred for 10 minutes at the same temperature, 0.7 g of isobutyl chloroformate was added to the mixture, and subsequently the whole mixture was stirred for 1 hour at −20° C. 1.0 g of 2-(4-cyanophenoxy)-1,2-dimethylethylamine was added to this mixture at −60° C., and then the reaction mixture was allowed to sit and warm naturally to room temperature while being stirred. The whole mixture was stirred for 20 hours at room temperature. Water was subsequently added to the reaction mixture. After the methylene chloride layer was washed successively with a 5% aqueous solution of sodium bicarbonate and water, the organic layer was dried over anhydrous sodium sulfate and the methylene chloride was removed under reduced pressure. The residue was purified by column chromatography on silica gel, thus yielding 1.2 g of the desired product in the form of a colorless glassy substance (yield: 61%).

| $^1$H-NMR: | (CDCl$_3$, δ) | |
|---|---|---|
| | 0.79 ~ 1.03 | (6H, m) |
| | 1.15 ~ 1.46 | (15H, m) |
| | 2.03 | (1H, m) |
| | 3.63 ~ 4.72 | (3H, m) |
| | 5.06 | (1H, m) |
| | 6.30 | (1H, m) |
| | 6.83 ~ 7.60 | (4H, m) |

SYNTHESIS EXAMPLE 65

Synthesis of $N^1$-[2-(4-cyanophenoxy)propyl]-$N^2$-phenoxycarbonyl-L-valinamide (Compound No. 750)

0.16 g of N-methylpiperidine was added to a suspension containing 0.25 g of $N^1$-[2-(4-cyanophenoxy)propyl]-L-valinamide hydrochloride suspended in 20 ml of methylene chloride, at −20° C. After the mixture was stirred for 10 minutes at the same temperature, 0.13 g of phenyl chloroformate was added drop by drop to the mixture, and then the reaction mixture was allowed to sit and warm naturally to room temperature while being stirred. The whole mixture was stirred for 3 hours at room temperature. After the methylene chloride was removed under reduced pressure, the residue was purified by column chromatography on silica gel, thus yielding 0.2 g of the desired product in the form of a white glutinous substance (yield: 63%).

| $^1$H-NMR: | (CDCl$_3$, δ) | |
|---|---|---|
| | 1.00 | (6H, m) |
| | 1.23 | (3H, d) |
| | 2.13 | (1H, m) |
| | 3.31 | (1H, m) |
| | 4.00 | (2H, m) |
| | 4.49 | (1H, m) |
| | 5.93 | (1H, d) |
| | 6.52 | (1H, m) |
| | 6.80 ~ 7.56 | (9H, m) |

SYNTHESIS EXAMPLE 66

Synthesis of $N^1$-[2-(4-cyanophenoxy)-1,1-dimethylethyl]-$N^2$-(2-fluorophenoxycarbonyl)-L-valinamide (Compound No. 777)

0.21 g of N-methylmorpholine, and subsequently 0.36 g of 2-fluorophenyl chloroformate, were added to a solution containing 0.6 g of $N^1$-[2-(4-cyanophenoxy)-1,1-dimethylethyl]-L-valinamide dissolved in 40 ml of methylene chloride at −15° C. The mixture was stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.52 g of the desired product in the form of a colorless grain crystal (yield: 58%).

SYNTHESIS EXAMPLE 67

Synthesis of $N^1$-[2-(4-cyanophenoxy)-1,1-dimethylethyl]-$N^2$-(3-fluorophenoxycarbonyl)-L-valinamide (Compound No. 779)

0.24 g of N-methylmorpholine, and subsequently 0.42 g of 3-fluorophenyl chloroformate were added to a solution containing 0.7 g of $N^1$-[2-(4-cyanophenoxy)-1,1-dimethylethyl]-L-valinamide dissolved in 40 ml of methylene chloride at −15° C. The mixture was stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.53 g of the desired product in the form of a colorless grain crystal (yield: 51%).

SYNTHESIS EXAMPLE 68

Synthesis of $N^1$-[2-(4-cyanophenoxy)-1,1-dimethylethyl]-$N^2$-(4-fluorophenoxycarbonyl)-L-valinamide (Compound No. 781)

0.45 g of N-methylmorpholine, and subsequently 0.78 g of 4-fluorophenyl chloroformate were added to a solution containing 1.3 g of $N^1$-[2-(4-cyanophenoxy)-1,1-dimethylethyl]-L-valinamide dissolved in 50 ml of methylene chloride at −15° C. The mixture was stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.45 g of the desired product in the form of a colorless grain crystal (yield: 76%).

SYNTHESIS EXAMPLE 69

Synthesis of $N^1$-[2-(4-cyanophenoxy)-1,1-dimethylethyl]-$N^2$-(4-fluorophenoxycarbonyl)-DL-valinamide (Compound No. 782)

0.58 g of N-methylpiperidine was added to a solution containing 1.5 g of N-(4-fluorophenoxycarbonyl)-DL-valine dissolved in 50 ml of methylene chloride, at −20° C. After the mixture was stirred for 10 minutes at the same temperature, 0.8 g of isobutyl chloroformate was added to the mixture at −20° C., and then the reaction mixture was stirred for 30 minutes at the same temperature. 1.12 g of 2-(4-cyanophenoxy)-1,1-dimethylamine was added to the reaction mixture at −60° C., and subsequently the whole mixture was stirred for 15 hours at room temperature. Water was added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 1.4 g of the desired product in the form of a colorless grain crystal (yield: 56%).

SYNTHESIS EXAMPLE 70

Synthesis of $N^1$-[2-(4-cyanophenoxy)-1,1-dimethylethyl]-$N^2$-(2,4-difluorophenoxycarbonyl)-L-valinamide (Compound No. 785)

0.24 g of N-methylmorpholine, and subsequently 0.45 g of 2,4-difluorophenyl chloroformate were added to a solution containing 0.68 g of $N^1$-[2-(4-cyanophenoxy)-1,1-dimethylethyl]-L-valinamide dissolved in 40 ml of methylene chloride at −15° C. The mixture was stirred for 15 hours at room temperature. Water was subsequently added to the reaction mixture. After the methylene chloride layer was washed with water, the organic layer was dried over anhydrous magnesium sulfate and then the methylene chloride was removed under reduced pressure. The residue was purified by column chromatography on silica gel, thus yielding 0.3 g of the desired product in the form of a colorless grain crystal (yield: 29%).

The agricultural or horticultural fungicide according to the present invention includes an amino-acid amide derivative represented by Formula [I] as an active ingredient. In the case where the compounds according to the present invention are employed as an agricultural or horticultural fungicide, the compounds acting as the active ingredient can be formulated appropriately, depending on the purpose. The active ingredient is usually diluted in an inert liquid or a solid carrier, and a surfactant or the like is added thereto, if necessary. The mixture is then formulated in a known manner into, for example, a fine powder, a wettable powder, an emulsifiable concentrate, granules, or the like.

The proportion of the active ingredient is selected as needed. When formulated into a fine powder or granules, 0.1% by weight to 20% by weight of the active ingredient is preferred. For an emulsifiable concentrate or wettable powder, 5% by weight to 80% by weight of the active ingredient is preferred.

As the suitable carriers employed in the formulation, there can be mentioned solid carriers such as talc, bentonite, clay, kaolin, diatomaceous earth, white carbon, vermiculite, slaked lime, siliceous sand, ammonium sulfate, urea, or the like; and liquid carriers such as isopropyl alcohol, xylene, cyclohexanone, methylnaphthalene, and the like.

As the surfactants and dispersants, there can be mentioned dinaphthylmethane disulfonate, alcohol sulfates, alkyl aryl sulfonates, ligninesulfonates, polyoxyethylene glycol ethers, polyoxyethylene alkyl aryl ethers, polyoxyethylene sorbitan monoalkylates, and the like. As the auxiliary agents, there can be mentioned carboxymethylcellulose, and the like.

The formulated agricultural or horticultural fungicide according to the present invention can be spread in an appropriate diluted concentration or can be applied directly.

The rate of application of the agricultural or horticultural fungicide according to the present invention may vary depending on the type of active compound employed, the kind of the pest or disease to be controlled, the nature of occurrence of the pest or disease, the degree of damage, environmental conditions, the form of preparation to be used, and the like. When the agricultural or horticultural fungicide of the present invention is applied directly in the form of fine powder or granules, it is recommended that the rate of application of the active ingredient be suitably chosen within the range of 0.1 g to 5 kg per 10 ares, and preferably, in the range of 1 g to 1 kg per 10 ares. In addition, when the fungicide of the present invention is in the form of a liquid such as an emulsifiable concentrate or a wettable powder, it is recommended that the ratio for application of the active ingredient be suitably chosen within the range of 0.1 ppm to 10,000 ppm, and preferably within the range of 10 ppm to 3,000 ppm.

The agricultural or horticultural fungicide according to the present invention can be employed for a number of purposes: for example, treating seeds, spraying of stem and leaf portions, applying to the soil, and injection into irrigation water. The agricultural or horticultural fungicide of the present invention can control plant diseases caused by fungi in the *Oomycetes, Ascomycetes, Deuteromycetes,* and *Basidiomycetes* or other pathogenic fungi.

The fungi include, but are not limited to, *Pseudoperonospora* such as cucumber downy mildew (*Pseudoperonospora cubensis*); *Phytophthora* such as tomato late blight (*Phytophthora infestans*); and *Plasmopara* such as grape downy mildew (*Plasmopara viticola*). The compounds according to the present invention may be employed alone or in combination with other fungicides, insecticides, herbicides, plant growth modifiers, fertilizers or the like.

Next, the representative formulations are illustrated with reference to the following Formulation Examples, wherein all "%" represent "percent by weight".

Formulation Example 1: Fine powder

2% of Compound No. 15, 5% of diatomaceous earth, and 93% of clay were uniformly mixed and ground into a fine powder.

Formulation Example 2: Wettable powder

50% of Compound No. 16, 45% of diatomaceous earth, 2% of sodium dinaphthylmethanedisulfonate, and 3% of sodium ligninsulfonate were uniformly mixed and ground into a wettable powder.

Formulation Example 3: Emulsifiable concentrate

30% of Compound No. 19, 20% of cyclohexanone, 11% of polyoxyethylene alkyl aryl ether, 4% of calcium alkylbenzenesulfonate, and 35% of methylnaphthalene were uniformly dissolved, thus obtaining an emulsifiable concentrate.

Formulation Example 4: Granules

5% of Compound No. 101, 2% of sodium lauryl alcohol sulfate, 5% of sodium ligninsulfonate, 2% of carboxymethylcellulose, and 86% of clay were mixed and ground. 20% of water was added to the ground mixture. The resulting mixture was kneaded and formed into granules of 14 mesh to 32 mesh by means of an extrusion granulator, and then dried into the desired granules.

EFFECTS OF THE INVENTION

The agricultural or horticultural fungicides according to the present invention exhibit high ability to prevent fungal infection by cucumber downy mildew (*Pseudoperonospora cubensis*), tomato late blight (*Phytophthora infestans*), and grape downy mildew (*Plasmopara viticola*). In addition, the agricultural or horticultural fungicides according to the present invention not only exhibit the ability to prevent fungal infection, but also exhibit the ability to eliminate pathogenic fungi after it has invaded a host plant.

Furthermore, the agricultural or horticultural fungicides of the present invention are also characterized in that they are not harmful chemicals and exhibit excellent characteristics such as systemic action, residual activity, and persistence after rain-fall.

The effects of the compounds according to the present invention are now illustrated with reference to the following Test Examples. In the Test Examples, the compounds mentioned below are employed as Comparative Compounds.

Comparative Compound X:

$N^2$-tert-butoxycarbonyl-$N^1$-(2-phenoxyethyl)-D-alaninamide (described in Japanese Patent Application First Publication No. 62-89696)

Comparative Compound Y:

$N^2$-tert-butoxycarbonyl-$N^1$-(2-phenylthioethyl)-D-alaninamide (described in Japanese Patent Application First Publication No. 62-89696)

Test Example 1:

Test on the Effect of Preventing Infection by Cucumber Downy Mildew (*Pseudoperonospora cubensis*)

Cucumber seeds (variety: "*Sagami hanjiro*") were sown at a rate of 10 seeds each in a square PVC (polyvinyl chloride) pot, wherein each side is 9 cm wide. The seeds were allowed to grow in a greenhouse, for 7 days, to the cotyledonous stage. A wettable powder prepared as in Formulation Example 2 was diluted with water to a concentration of 500 ppm of the active ingredient, and the aqueous preparation obtained was then applied at a rate of 10 ml per pot to the cucumber seedlings at their cotyledonous stage. After drying in the air, the plant was inoculated with a conidiospore suspension of cucumber downy mildew (*Pseudoperonospora cubensis*) fungi using a spray and then placed in a moist chamber at 22° C. for 24 hours, and then placed in a greenhouse. On the seventh day after the inoculation, the affected area was rated. The results of the test in accordance with the standards of evaluation as shown in Table 14 are given in Table 15.

TABLE 14

| Standard of evaluation: | Affected area |
|---|---|
| Class A: | No lesions were observed |
| Class B: | Affected area is less than 25% |
| Class C: | Affected area is 25% or more and less than 50% |
| Class D: | Affected area is 50% or more |

TABLE 15

| Compound No. | Evaluation |
|---|---|
| 1 | B |
| 2 | A |
| 4 | A |
| 6 | A |
| 7 | A |
| 8 | B |
| 10 | A |
| 13 | A |
| 14 | B |
| 16 | A |
| 17 | A |
| 18 | B |
| 19 | A |
| 23 | A |
| 24 | B |
| 26 | B |
| 27 | A |
| 29 | A |
| 33 | A |
| 42 | A |
| 45 | A |
| 54 | B |
| 63 | A |
| 77 | A |
| 88 | A |
| 98 | A |
| 101 | A |
| 104 | A |
| 107 | A |
| 108 | A |
| 112 | A |
| 114 | A |
| 115 | A |
| 116 | A |
| 124 | B |
| 129 | A |
| 134 | A |
| 135 | A |
| 154 | A |
| 157 | A |
| 160 | A |
| 163 | A |
| 166 | A |
| 169 | A |
| 184 | A |
| 193 | A |
| 195 | B |
| 204 | B |
| 205 | A |
| 208 | A |
| 211 | A |
| 212 | A |
| 213 | A |
| 214 | A |
| 215 | A |
| 216 | A |
| 217 | A |
| 219 | A |
| 220 | A |
| 221 | A |
| 227 | A |
| 228 | A |
| 230 | A |
| 231 | A |

TABLE 15-continued

| Compound No. | Evaluation |
|---|---|
| 232 | A |
| 235 | A |
| 236 | A |
| 238 | A |
| 246 | B |
| 323 | A |
| 326 | A |
| 327 | A |
| 328 | A |
| 329 | B |
| 331 | B |
| 333 | B |
| 335 | A |
| 336 | A |
| 338 | A |
| 339 | A |
| 340 | A |
| 341 | A |
| 342 | A |
| 343 | A |
| 344 | B |
| 345 | A |
| 347 | A |
| 348 | B |
| 349 | A |
| 350 | B |
| 351 | A |
| 352 | A |
| 353 | A |
| 354 | A |
| 355 | A |
| 356 | A |
| 357 | B |
| 358 | A |
| 359 | A |
| 360 | A |
| 361 | B |
| 362 | B |
| 363 | A |
| 364 | B |
| 365 | A |
| 366 | A |
| 367 | A |
| 368 | A |
| 369 | A |
| 370 | A |
| 371 | A |
| 372 | A |
| 373 | A |
| 374 | A |
| 376 | A |
| 377 | A |
| 378 | A |
| 379 | A |
| 380 | A |
| 381 | A |
| 382 | A |
| 383 | A |
| 385 | A |
| 386 | A |
| 387 | B |
| 388 | A |
| 389 | A |
| 390 | A |
| 391 | A |
| 392 | A |
| 393 | A |
| 394 | A |
| 395 | A |
| 397 | A |
| 399 | A |
| 401 | A |
| 402 | A |
| 403 | A |
| 405 | A |
| 408 | A |
| 410 | A |
| 411 | B |
| 412 | A |
| 413 | A |
| 414 | A |
| 416 | A |
| 417 | A |
| 418 | A |
| 419 | A |
| 421 | A |
| 422 | A |
| 423 | A |
| 424 | A |
| 425 | A |
| 426 | A |
| 427 | A |
| 429 | A |
| 430 | A |
| 431 | A |
| 432 | A |
| 439 | A |
| 440 | A |
| 451 | A |
| 452 | A |
| 453 | A |
| 455 | A |
| 456 | A |
| 462 | A |
| 465 | A |
| 466 | A |
| 467 | A |
| 468 | A |
| 471 | B |
| 477 | A |
| 482 | A |
| 486 | A |
| 492 | A |
| 493 | A |
| 495 | A |
| 496 | B |
| 499 | B |
| 502 | A |
| 506 | A |
| 508 | A |
| 509 | A |
| 510 | A |
| 511 | A |
| 512 | A |
| 513 | A |
| 517 | A |
| 519 | A |
| 523 | A |
| 525 | A |
| 605 | A |
| 606 | A |
| 607 | A |
| 708 | A |
| 768 | A |
| 770 | A |
| Comparative Example X | D |
| Comparative Example Y | D |

Test Example 2:

Test on the Effect of Treating Infection by Cucumber Downy Mildew (*Pseudoperonospora cubensis*)

Cucumber seeds (variety: "*Sagami hanjiro*") were sown at a rate of 10 seeds each in a square PVC (polyvinyl chloride) pot, wherein each side is 9 cm wide. The seeds were allowed to grow in a greenhouse, for 7 days, to the cotyledonous stage. The seedlings were inoculated with a spore suspension of cucumber downy mildew (*Pseudoperonospora cubensis*) fungi and then placed in a moist chamber at 22° C. for 24 hours. After drying in the air, a wettable powder prepared as in Formulation Example 2 was diluted with water to a concentration of 500 ppm of the active ingredient, and the aqueous preparation obtained was then applied at a rate of 10 ml per pot to the cucumber seedlings. The seedlings were then placed in a green house. On the seventh day after the inoculation, the extent of lesions was rated. The results of the test in accordance with the standards of evaluation shown in Table 14 are given in Table 16.

TABLE 16

| Compound No. | Evaluation |
|---|---|
| 4 | B |
| 10 | A |
| 13 | A |
| 16 | A |
| 19 | B |
| 29 | A |
| 33 | A |
| 42 | A |
| 45 | A |
| 54 | B |
| 63 | A |
| 77 | B |
| 88 | B |
| 104 | A |
| 107 | A |
| 108 | B |
| 114 | B |
| 115 | A |
| 116 | A |
| 124 | A |
| 129 | B |
| 134 | A |
| 135 | A |
| 154 | A |
| 157 | A |
| 160 | A |
| 163 | A |
| 184 | B |
| 212 | A |
| 213 | A |
| 215 | A |
| 216 | B |
| 219 | A |
| 220 | B |
| 221 | A |
| 228 | B |
| 230 | B |
| 231 | A |
| 232 | A |
| 238 | A |
| 333 | A |
| 335 | A |
| 336 | A |
| 340 | B |
| 341 | B |
| 342 | A |
| 345 | A |
| 348 | B |
| 349 | A |
| 351 | A |
| 352 | A |
| 353 | A |
| 354 | A |
| 355 | A |
| 356 | A |
| 358 | A |
| 360 | B |
| 365 | A |
| 367 | B |
| 368 | A |
| 369 | A |
| 371 | A |
| 374 | A |
| 376 | A |
| 378 | A |
| 381 | B |
| 382 | A |
| 383 | A |

TABLE 16-continued

| Compound No. | Evaluation |
|---|---|
| 385 | A |
| 386 | A |
| 388 | A |
| 394 | A |
| 395 | A |
| 397 | A |
| 399 | A |
| 401 | A |
| 402 | A |
| 405 | A |
| 414 | A |
| 416 | A |
| 417 | A |
| 418 | A |
| 419 | A |
| 423 | A |
| 424 | A |
| 425 | A |
| 427 | A |
| 429 | A |
| 439 | A |
| 451 | A |
| 452 | A |
| 453 | A |
| 455 | A |
| 456 | A |
| 462 | A |
| 465 | A |
| 466 | A |
| 467 | B |
| 468 | A |
| 477 | B |
| 486 | B |
| 492 | A |
| 495 | A |
| 499 | B |
| 502 | A |
| 506 | A |
| 508 | A |
| 509 | A |
| 513 | A |
| 517 | A |
| 519 | B |
| 523 | A |
| 606 | A |
| 607 | B |
| 708 | A |
| 768 | B |
| 770 | B |
| Comparative Example X | D |
| Comparative Example Y | D |

Test Example 3:

Test on the Effect of Preventing infection by Tomato Late Blight (*Phytophthora infestans*)

One tomato seedling (variety: "*Ponterosa*") was transplanted into each ceramic pot (diameter: 12 cm) and grown in a greenhouse. A wettable powder prepared as in Formulation Example 2 was diluted with water to a concentration of 500 ppm of the active ingredient, and the aqueous preparation obtained was then applied at a rate of 20 ml per pot to the tomato seedlings at their 6- or 7-leaf stage. After drying in the air, the plant was inoculated with a zoosporangium suspension of tomato late blight (*Phytophthora infestans*) fungi and then placed in a moist chamber at 22° C. On the fourth day after the inoculation, the affected area was rated. The index of incidence was determined based on the size of the affected area as shown in Table 17. The degree of damage was calculated according to the following first equation and the index of incidence and the ability to prevent the disease (controlling activity) was calculated according to the second equation. The results are shown in Table 18.

TABLE 17

| Incidence Index | Affected Area |
|---|---|
| 0 | No lesions |
| 1 | Less an 5% |
| 2 | 5% or more and less than 33.3% |
| 3 | 33.3% or more and less than 66.6% |
| 4 | 66.6% or more |

Equation (1)

$$\text{Degree of Damage (\%)} = \frac{\Sigma(\text{Incidence Index} \times \text{Number of Proper Leaves})}{4 \times \text{Number of Leaves Examined}}$$

Equation (2)

$$\text{Controlling Activity (\%)} = \left(1 - \frac{\text{Degree of Damage}}{\text{Degree of Damage in Untreated Plot}}\right) \times 100$$

TABLE 18

| Compound No. | Controlling Activity (%) |
|---|---|
| 2 | 100 |
| 4 | 100 |
| 6 | 100 |
| 7 | 100 |
| 10 | 100 |
| 13 | 100 |
| 16 | 100 |
| 17 | 100 |
| 19 | 100 |
| 23 | 100 |
| 27 | 100 |
| 29 | 100 |
| 33 | 100 |
| 42 | 100 |
| 45 | 100 |
| 63 | 100 |
| 77 | 100 |
| 88 | 100 |
| 98 | 100 |
| 101 | 100 |
| 104 | 100 |
| 107 | 100 |
| 108 | 100 |
| 112 | 100 |
| 115 | 100 |
| 116 | 100 |
| 129 | 100 |
| 134 | 100 |
| 135 | 100 |
| 154 | 100 |
| 157 | 100 |
| 160 | 100 |
| 163 | 100 |
| 166 | 100 |
| 169 | 100 |
| 184 | 100 |
| 193 | 100 |
| 213 | 100 |
| 215 | 100 |
| 217 | 100 |
| 220 | 100 |
| 221 | 100 |
| 228 | 100 |
| 231 | 100 |
| 232 | 100 |
| 235 | 100 |
| 238 | 100 |
| 323 | 100 |
| 326 | 100 |
| 336 | 100 |
| 345 | 100 |
| 352 | 100 |
| 356 | 100 |
| 359 | 100 |
| 360 | 100 |
| 364 | 100 |
| 365 | 100 |
| 369 | 100 |
| 371 | 100 |
| 372 | 100 |
| 373 | 100 |
| 374 | 100 |
| 378 | 100 |
| 379 | 100 |
| 380 | 100 |
| 381 | 100 |
| 382 | 100 |
| 386 | 100 |
| 388 | 100 |
| 390 | 100 |
| 391 | 100 |
| 393 | 100 |
| 394 | 100 |
| 395 | 100 |
| 397 | 100 |
| 399 | 100 |
| 401 | 100 |
| 402 | 100 |
| 403 | 100 |
| 404 | 100 |
| 405 | 100 |
| 408 | 100 |
| 414 | 100 |
| 417 | 100 |
| 418 | 100 |
| 423 | 100 |
| 424 | 100 |
| 427 | 100 |
| 430 | 100 |
| 439 | 100 |
| 440 | 100 |
| 451 | 100 |
| 462 | 100 |
| 465 | 100 |
| 466 | 100 |
| 467 | 100 |
| 477 | 100 |
| 482 | 100 |
| 492 | 100 |
| 495 | 100 |
| 502 | 100 |
| 508 | 100 |
| 509 | 100 |
| 513 | 100 |
| 519 | 100 |
| 523 | 100 |
| 605 | 100 |
| 606 | 100 |
| 607 | 100 |
| 708 | 100 |
| 768 | 100 |
| 770 | 100 |
| Comparative Example X | 0 |
| Comparative Example Y | 0 |

Test Example 4:

Test on the Effect of Preventing Infection by Grape Downy Mildew (*Plasmopara viticola*)

Rooted grape cuttings (variety: "*Kyoho*") were each grown from a cutting, pruned, grown in a ceramic pot (diameter: 12 cm), and maintained in a greenhouse. A wettable powder prepared as in Formulation Example 2 was diluted with water to a concentration of 500 ppm of the active ingredient, and the aqueous preparation obtained was then applied at a rate of 20 ml per pot to the grape seedlings at their 4- or 5-leaf stage. After drying in the air, the plant was inoculated with a zoosporangium suspension of grape downy mildew (*Plasmopara viticola*) fungi and then placed in a moist chamber at 22° C. for 24 hours. On the seventh day in the greenhouse after the inoculation, the plant was again placed in a moist chamber at 22° C. for 24 hours to cultivate conidiospores. The incidence area where conidiospores grew on each leaf was examined.

The incidence index was determined according to the standards shown in Table 17. The degree of damage was calculated according to Equation (1) and the incidence index and the ability to prevent the disease (controlling activity) was calculated according to Equation (2). The results of the test are shown in Table 19.

TABLE 19

| Compound No. | Controlling Activity (%) |
|---|---|
| 2 | 100 |
| 4 | 100 |
| 6 | 100 |
| 7 | 100 |
| 10 | 100 |
| 13 | 100 |
| 16 | 100 |
| 17 | 100 |
| 19 | 100 |
| 23 | 100 |
| 27 | 100 |
| 29 | 100 |
| 33 | 100 |
| 42 | 100 |
| 45 | 100 |
| 63 | 100 |
| 77 | 100 |
| 88 | 100 |
| 98 | 100 |
| 101 | 100 |
| 104 | 100 |
| 107 | 100 |
| 108 | 100 |
| 112 | 100 |
| 115 | 100 |
| 116 | 100 |
| 129 | 100 |
| 134 | 100 |
| 135 | 100 |
| 154 | 100 |
| 157 | 100 |
| 160 | 100 |
| 163 | 100 |
| 166 | 100 |
| 169 | 100 |
| 184 | 100 |
| 193 | 100 |
| 213 | 100 |
| 215 | 100 |
| 217 | 100 |
| 220 | 100 |
| 221 | 100 |
| 228 | 100 |
| 231 | 100 |
| 232 | 100 |
| 235 | 100 |
| 238 | 100 |
| 323 | 100 |
| 326 | 100 |
| 336 | 100 |
| 345 | 100 |
| 352 | 100 |
| 356 | 100 |
| 359 | 100 |
| 360 | 100 |
| 264 | 100 |
| 365 | 100 |
| 369 | 100 |

TABLE 19-continued

| Compound No. | Controlling Activity (%) |
|---|---|
| 371 | 100 |
| 372 | 100 |
| 373 | 100 |
| 374 | 100 |
| 378 | 100 |
| 379 | 100 |
| 380 | 100 |
| 381 | 100 |
| 382 | 100 |
| 386 | 100 |
| 388 | 100 |
| 390 | 100 |
| 391 | 100 |
| 393 | 100 |
| 394 | 100 |
| 395 | 100 |
| 397 | 100 |
| 399 | 100 |
| 401 | 100 |
| 402 | 100 |
| 403 | 100 |
| 404 | 100 |
| 405 | 100 |
| 408 | 100 |
| 414 | 100 |
| 417 | 100 |
| 418 | 100 |
| 423 | 100 |
| 424 | 100 |
| 427 | 100 |
| 430 | 100 |
| 439 | 100 |
| 440 | 100 |
| 451 | 100 |
| 462 | 100 |
| 465 | 100 |
| 466 | 100 |
| 467 | 100 |
| 477 | 100 |
| 482 | 100 |
| 492 | 100 |
| 495 | 100 |
| 502 | 100 |
| 508 | 100 |
| 509 | 100 |
| 513 | 100 |
| 519 | 100 |
| 523 | 100 |
| 605 | 100 |
| 606 | 100 |
| 607 | 100 |
| 708 | 100 |
| 768 | 100 |
| 770 | 100 |
| Comparative Example X | 0 |
| Comparative Example Y | 0 |

Test Example 5:

Test on the Effect of Preventing Infection by Cucumber Downy Mildew (*Pseudoperonospora cubensis*)

Cucumber seeds (variety: "*Sagami hanjiro*") were sown at a rate of 10 seeds each in a square PVC (polyvinyl chloride) pot, wherein each side is 9 cm wide. The seeds were allowed to grow in a greenhouse, for 7 days, to the cotyledonous stage. A wettable powder prepared as in Formulation Example 2 was diluted with water to a concentration of 100 ppm of the active ingredient, and the aqueous preparation obtained was then applied at a rate of 10 ml per pot to the cucumber seedlings at their cotyledonous stage. After drying in the air, the plant was inoculated with a conidiospore suspension of cucumber downy mildew (*Pseudoperonospora cubensis*) fungi using a spray and then placed in a moist chamber at 22° C. for 24 hours, and then placed in a greenhouse. On the seventh day after the inoculation, the affected area was rated. The results of the test in accordance with the standards of evaluation as shown in Table 14 are given in Table 20.

TABLE 20

| Compound No. | Evaluation |
|---|---|
| 777 | A |
| 779 | A |
| 781 | A |
| 785 | A |

Test Example 6:

Test on the Effect of Treating Infection by Cucumber Downy Mildew (*Pseudoperonospora cubensis*)

Cucumber seeds (variety: "*Sagami hanjiro*") were sown at a rate of 10 seeds each in a square PVC (polyvinyl chloride) pot, wherein each side is 9 cm wide. The seeds were allowed to grow in a greenhouse, for 7 days, to the cotyledonous stage. The seedlings were inoculated with a spore suspension of cucumber downy mildew (*Pseudoperonospora cubensis*) fungi and then placed in a moist chamber at 22° C. for 24 hours. After drying in the air, a wettable powder prepared as in Formulation Example 2 was diluted with water to a concentration of 500 ppm of the active ingredient, and the aqueous preparation obtained was then applied at a rate of 10 ml per pot to the cucumber seedlings. The seedlings were then placed in a green house. On the seventh day after the inoculation, the extent of lesions was rated.

The results of the test in accordance with the standards of evaluation shown in Table 14 are given in Table 21.

TABLE 21

| Compound No. | Evaluation |
|---|---|
| 777 | A |
| 779 | A |
| 781 | A |
| 785 | A |

Test Example 7:

Test on the Effect of Preventing Infection by Tomato Late Blight (*Phytophthora infestans*)

One tomato seedling (variety: "*Ponterosa*") was transplanted into each ceramic pot (diameter: 12 cm) and grown in a greenhouse. A wettable powder prepared as in Formulation Example 2 was diluted with water to a concentration of 500 ppm of the active ingredient, and the aqueous preparation obtained was then applied at a rate of 20 ml per pot to the tomato seedlings at their 6- or 7-leaf stage. After drying in the air, the plant was inoculated with a zoosporangium suspension of tomato late blight (*Phytophthora infestans*) fungi and then placed in a moist chamber at 22° C. On the fourth day after the inoculation, the affected area on each leaf was rated.

The index of incidence was determined based on the size of the affected area as shown in Table 17. The degree of damage was calculated according to the following first equation and the index of incidence and the ability to prevent the disease (controlling activity) was calculated according to the second equation. The results are shown in Table 22.

TABLE 22

| Compound No. | Controlling Activity (%) |
|---|---|
| 777 | 100 |
| 779 | 100 |
| 781 | 100 |
| 785 | 100 |

Test Example 8:

Test on the Effect of Preventing Infection by Grape Downy Mildew (*Plasmopara viticola*)

Rooted grape cuttings (variety: "*Kyoho*") were each grown from a cutting, pruned, grown in a porcelain pot (diameter: 12 cm), and maintained in a greenhouse. A wettable powder prepared as in Formulation Example 2 was diluted with water to a concentration of 500 ppm of the active ingredient, and the aqueous preparation obtained was then applied at a rate of 20 ml per pot to the grape seedlings at their 4- or 5-leaf stage. After drying in the air, the plant was inoculated with a zoosporangium suspension of grape downy mildew (*Plasmopara viticola*) fungi and then placed in a moist chamber at 22° C. for 24 hours. On the seventh day in the greenhouse after the inoculation, the plant was again placed in a moist chamber at 22° C. for 24 hours to cultivate conidiospores. The incidence area where conidiospores grew on each leaf was examined.

The incidence index was determined according to the standards shown in Table 17. The degree of damage was calculated according to Equation (1) and the incidence index and the ability to prevent the disease (controlling activity) was calculated according to Equation (2). The results of the test are shown in Table 23.

TABLE 23

| Compound No. | Controlling Activity (%) |
|---|---|
| 777 | 100 |
| 779 | 100 |
| 781 | 100 |
| 785 | 100 |

What is claimed is:

1. An amino-acid amide derivative represented by the formula:

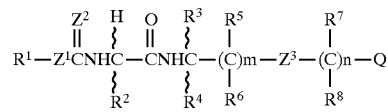

wherein $R^1$ represents a cyclic ether group, $R^2$ represents a lower alkyl group, a lower alkenyl group, a cycloalkyl group, or a phenyl group (optionally having at least one substituent of halogen atom), $R^3$ represents a hydrogen atom or a lower alkyl group, $R^4$ represents a hydrogen atom, a lower alkyl group, or a cyano group, $R^5$, $R^6$, and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $Z^1$ and $Z^2$ independently represent an oxygen atom or a sulfur atom, Z³ represents
an oxygen atom,
a sulfur atom,
a group $$N-R^{10}$$

(wherein R¹⁰ represents a hydrogen atom, a methyl group, an acetyl group, a benzoyl group, a methoxycarbonyl group, or a methoxymethyl group),
sulfinyl group,
sulfonyl group,
a group —C(O)O—,
group $$CONR^{11}$$

(wherein R¹¹ represents a hydrogen atom or a lower alkyl group),
Q represents
(a) a phenyl group (optionally having at least one same or different substituent selected from the group consisting of
a halogen atom,
a lower alkyl group which may be substituted with at least one same or different halogen atom,
a lower alkoxy group which may be substituted with a same or different halogen atom,
a cyano group,
a nitro group,
a lower alkoxycarbonyl group,
a methylsulfonyl group,
a methylsulfinyl group,
a methylthio group which may be substituted with a halogen atom,
a dimethylamino group,
a phenylsulfonyl group,
an acyl group, and
a phenyl group),
(b) a cyclic ether group,
(c) a heterocyclic group (optionally having, a substituent selected from the group consisting of a halogen atom, an alkyl group, a trifluoromethyl group, and a nitro group), or
(d) a condensed heterocyclic group optionally having a substituent selected from the group consisting of a halogen atom and a nitro group,
m represents an integer from 0 to 2, and
n represents 0 or 1.

2. An amino-acid amide derivative as recited in claim 1, which is represented by the formula:

$$R^1-Z^1CNHC-CNHC-(C)m-Z^3-(C)n-Q$$
with $Z^2$, H, O, $R^3$, $R^5$, $R^7$ above and CH, $R^4$, $R^6$, $R^8$ below, with $R^9$ and $CH_3$ on the CH branch wherein R¹ represents a cyclic ether group,
R³ represents a hydrogen atom or a lower alkyl group,
R⁴ represents a hydrogen atom, a lower alkyl group, or a cyano group,
R⁵, R⁶ and R⁷ independently represent a hydrogen atom or a lower alkyl group,
R⁸ represents a hydrogen atom, a lower alkyl group, an aralkyl group, a phenyl group, an alkoxycarbonyl group, or a cyano group,
R⁹ represents a hydrogen atom, a methyl group or an ethyl group,
Z¹ and Z² independently represent an oxygen atom or a sulfur atom,
Z³ represents an oxygen atom, a sulfur atom, a group $$N-R^{10}$$

(wherein R¹⁰ represents a hydrogen atom, a methyl group, an acetyl group, a benzoyl group, a methoxycarbonyl group, or a methoxymethyl group), a sulfinyl group, or a sulfonyl group,
Q represents
a phenyl group (optionally having at least one same or different substituent selected from the group consisting of
a halogen atom,
a lower alkyl group which may be substituted with at least one halogen atom,
a lower alkoxy group which may be substituted with at least one halogen atom,
a cyano group,
a nitro group,
a lower alkoxycarbonyl group,
a methylsulfonyl group,
a methylsulfinyl group,
a methylthio group which may be substituted with a halogen atom,
a dimethylamino group,
a phenylsulfonyl group,
an acyl group, and
a phenyl group),
a heterocyclic group (optionally having a substituent selected from the group consisting of a halogen atom and a nitro group), or
a condensed heterocyclic group (optionally having a substituent selected from the group consisting of a halogen atom and a nitro group),
m represents an integer from 0 to 2, and
n represents 0 or 1.

3. An amino-acid amide derivative as recited in claim 1, which is represented by the formula:

$$R^1-Z^1CNHC-CNHC-(CH)m-Z^3-(CH_2)n-Q$$
with $Z^2$, H, O, H above and CH, $R^4$, $R^6$ below, with $R^9$ and $CH_3$ on the CH branch wherein R¹ represents a C₂~C₈ cyclic ether group,
R⁴ represents a hydrogen atom, a C₁~C₃ alkyl group, or a cyano group,
R⁶ represents a hydrogen atom or a C₁~C₃ alkyl group,
R⁹ represents a hydrogen atom, a methyl group, or an ethyl group, $Z^1$ and $Z^2$ independently represent an oxygen atom or a sulfur atom, $Z^3$ represents an oxygen atom, a sulfur atom, a group $$\underset{|}{\overset{|}{N}}-R^{10}$$

(wherein $R^{10}$ represents a hydrogen atom, a methyl group, an acetyl group, or a benzoyl group), a sulfinyl group, or a sulfonyl group, Q represents a phenyl group (optionally having at least one same or different substituent selected from the group consisting of a halogen atom, a $C_1$~$C_3$ alkyl group which may be substituted with at least one same or different halogen atom, a $C_1$~$C_3$ alkoxy group which may be substituted with a same or different halogen atom, a cyano group, a nitro group, a methylsulfonyl group, a methylsulfinyl group, and a methylthio group, a pyridyl group which may be substituted with a halogen atom, or a pyrimdinyl group, m represents 1 or 2, and n represents 0 or 1.

4. An amino-acid amide derivative as recited in claim 1, which is represented by the formula:

$$R^1-Z^1\overset{Z^2}{\underset{\underset{C_2H_5}{|}}{\overset{||}{C}}}NH\overset{H}{\underset{\underset{CH_3}{|}}{C}}-\overset{O}{\overset{||}{C}}NH\overset{H}{\underset{|}{C}}-CH_2O-\phantom{}\hspace{-0.5em}\bigcirc\hspace{-0.5em}-X$$

wherein X represents a halogen atom, a cyano group, or a nitro group.

5. An amino-acid amide derivative is recited in claim 1, which is represented by the formula:

$$R^1-Z^1\overset{Z^2}{\overset{||}{C}}NH\overset{H}{\underset{\underset{CH}{|}\atop CH_3\;\;CH_3}{C}}-\overset{O}{\overset{||}{C}}NH\overset{H}{\underset{\underset{CH_3}{|}}{C}}-CH_2O-\phantom{}\hspace{-0.5em}\bigcirc\hspace{-0.5em}-X$$

wherein X represents a halogen atom, a cyano group, or a nitro group.

6. An amino-acid amide derivative as recited in claim 1, which is represented by the formula:

$$R^1-O-\overset{O}{\overset{||}{C}}-NH-\overset{H}{\underset{\underset{R^2}{|}}{C}}-\overset{O}{\overset{||}{C}}-NH-\overset{H}{\underset{\underset{CH_3}{|}}{C}}-CH_2O-Q$$

wherein $R^2$ represents a propyl group, an isopropyl group, an isobutyl group, a tert-butyl group, an isopropenyl group, a $C_3$~$C_8$ cycloalkyl group, or a phenyl group (optionally having at least one substituent halogen atom), and Q represents a phenyl group (optionally having at least one substituent cyano group), a pyridyl group (optionally having at least one substituent of a same or different halogen atom or trifluoromethyl group), or a pyrimidinyl group (optionally having at least one same or different substituent of a halogen atom or $C_1$~$C_3$ alkyl group).

7. An amino-acid amide derivative as recited in claim 1, which is represented by the formula:

$$R^1-Z^1\overset{O}{\overset{||}{C}}NH\overset{H}{\underset{\underset{R^2}{|}}{C}}-\overset{O}{\overset{||}{C}}NH\overset{H}{\underset{\underset{R^4}{|}}{C}}-Z^3-(CH_2)n-Q$$

wherein $R^2$ represents an ethyl group, an isopropyl group, or a sec-butyl group, $R^4$ represents a hydrogen atom or a $C_1$~$C_3$ alkyl group, $Z^3$ represents a group —COO—, a group —CONR$^{12}$— (wherein $R^{12}$ represents a hydrogen atom or a $C_1$~$C_3$ alkyl group), Q represents a phenyl group (optionally having at least one same or different substituent selected from the group consisting of a halogen atom, a $C_1$~$C_3$ alkyl group, a $C_1$~$C_3$ alkoxy group, and a cyano group), and n represents 0 or 1.

8. An amino-acid amide derivative as recited in claim 1, represented by the formula:

$$F\hspace{-0.3em}\bigcirc\hspace{-0.3em}-O-\overset{O}{\overset{||}{C}}-NH-\overset{H}{\underset{\underset{CH}{|}\atop CH_3\;\;CH_3}{C}}-\overset{O}{\overset{||}{C}}-NH-\overset{CH_3}{\underset{\underset{CH_3}{|}}{\overset{|}{C}}}-CH_2O-\hspace{-0.3em}\bigcirc\hspace{-0.3em}-CN.$$

9. An amino-acid amide derivative represented by the formula:

$$R^1-Z^1\overset{Z^2}{\overset{||}{C}}NH\overset{H}{\underset{\underset{R^2}{|}}{C}}-\overset{O}{\overset{||}{C}}NH\overset{R^3}{\underset{\underset{R^4}{|}}{C}}-(\overset{R^5}{\underset{\underset{R^6}{|}}{C}})m-Z^3-(\overset{R^7}{\underset{\underset{R^8}{|}}{C}})n-Q$$

wherein $R^1$ represents (a) a lower alkyl group (optionally having at least one same or different substituent selected from the group consisting of a halogen atom, an alkoxy group, and a cyano group), (b) a lower alkenyl group, (c) a lower alkynyl group, (d) a cycloalkyl group (optionally having, at least one substituent selected from the group consisting of methyl group and a halogen atom), (e) a cycloalkylalkyl group, (f) a cycloalkenyl group, (g) a cyclic ether group, (h) a phenyl group (optionally having, at least one same or different substituent selected from the group consisting of a halogen atom, a lower alkyl group which may be substituted with a same or different halogen atom, a lower alkoxy group which may be substituted with a same or different halogen atom, a cyano group, and a nitro group), (i) an aralkyl group (optionally having at least one same or different substituent selected from the group consisting of a methyl group, a cyano group, and a nitro group), or (j) a heterocyclic group,
$R^2$ represents a lower alkyl group, a lower alkenyl group, a cycloalkyl group, or a phenyl group (optionally having at least one substituent of halogen atom),
$R^3$ represents a hydrogen atom or a lower alkyl group,
$R^4$ represents a hydrogen atom, a lower alkyl group, or a cyano group,
$R^5$, $R^6$, and $R^7$ independently represent a hydrogen atom or a lower alkyl group,
$R^8$ represents a hydrogen atom, a lower alkyl group, an aralkyl group, a phenyl group, an alkoxycarbonyl group, or a cyano group,
$Z^1$ and $Z^2$ independently represent an oxygen atom or a sulfur atom,
$Z^3$ represents
a sulfur atom,
a group

(wherein $R^{10}$ represents an acetyl group or a benzoyl group),
Q represents
(a) a phenyl group (optionally having at least one same or different substituent selected from the group consisting of
a halogen atom,
a lower alkyl group which may be substituted with at least one same or different halogen atom,
a lower alkoxy group which may be substituted with a same or different halogen atom,
a cyano group,
a nitro group,
a lower alkoxycarbonyl group,
a methylsulfonyl group,
a methylsulfinyl group,
a methylthio group which may be substituted with a halogen atom,
a dimethylamino group,
a phenylsulfonyl group,
an acyl group, and
a phenyl group),
(b) a cyclic ether group,
(c) a heterocyclic group (optionally having, a substituent selected from the group consisting of a halogen atom, an alkyl group, a trifluoromethyl group, and a nitro group), or
(d) a condensed heterocyclic group optionally having a substituent selected from the group consisting of a halogen atom and a nitro group,
m represents an integer from 0 to 2, and
n represents 0 or 1.
10. An amino-acid amide derivative as recited in claim 9, which is represented by the formula:

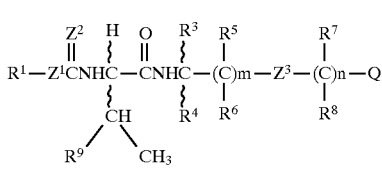

wherein $R^1$ represents
a lower alkyl group (optionally having at least one same or different substituent selected from the group consisting of a halogen atom and an alkoxy group),
a lower alkenyl group,
a lower alkynyl group,
a cycloalkyl group (optionally having at least one substituent of methyl group),
a cycloalkenyl group,
a cyclic ether group,
an aralkyl group (optionally having at least one same or different substituent selected from the group consisting of a methyl group, a cyano group, and a nitro group),
a phenyl group (optionally having at least one same or different substituents selected from the group consisting of a halogen atom, a methyl group, a methoxy group, a cyano group, a trifluoromethyl group, a trifluoromethoxy group, and a nitro group),
or a heterocyclic group,
$R^3$ represents a hydrogen atom or a lower alkyl group,
$R^4$ represents a hydrogen atom, a lower alkyl group, or a cyano group,
$R^5$, $R^6$ and $R^7$ independently represent a hydrogen atom or a lower alkyl group,
$R^8$ represents a hydrogen atom, a lower alkyl group, an aralkyl group, a phenyl group, an alkoxycarbonyl group, or a cyano group,
$R^9$ represents a hydrogen atom, a methyl group or an ethyl group,
$Z^1$ and $Z^2$ independently represent an oxygen atom or a sulfur atom,
$Z^3$ represents a sulfur atom, a group

(wherein $R^{10}$ represents an acetyl group or a benzoyl group)
Q represents
a phenyl group,
a heterocyclic group (optionally having a substituent selected from the group consisting of a halogen atom and a nitro group), or
a condensed heterocyclic group (optionally having a substituent selected from the group consisting of a halogen atom and a nitro group),
m represents an integer from 0 to 2, and
n represents 0 or 1.
11. An amino-acid amide derivative as recited in claim 9, which is represented by the formula:

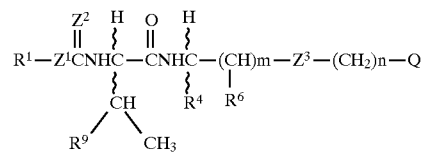

wherein $R^1$ represents a $C_1~C_6$ alkyl group (optionally having at least one same or different substituent selected from the group consisting of a halogen atom and an alkoxy group), a $C_2~C_6$ alkenyl group, a $C_2~C_6$ alkynyl group, a $C_3~C_8$ cycloalkyl group cycloalkyl group (optionally having at least one substituent of methyl group), a $C_2~C_8$ cyclic ether group, a $C_7~C_8$ aralkyl group (optionally having, at least one substituent of methyl group), or a phenyl group (optionally

193 having at least one same or different substituent selected from the group consisting of a halogen atom, a methyl group, a methoxy group, a trifluoromethyl group, a trifluoromethoxy group, and a nitro group), $R^4$ represents a hydrogen atom, a $C_1$~$C_3$ alkyl group, or a cyano group, $R^6$ represents a hydrogen atom or a $C_1$~$C_3$ alkyl group, $R^9$ represents a hydrogen atom, a methyl group, or an ethyl group, $Z^1$ and $Z^2$ independently represent an oxygen atom or a sulfur atom, $Z^3$ represents a sulfur atom, or a group

(wherein $R^{10}$ represents an acetyl group or a benzoyl group),

Q represents a phenyl group (optionally having at least one same or different substituent selected from the group consisting of a halogen atom, a $C_1$~$C_3$ alkyl group which may be substituted with at least one same or different halogen atom, a $C_1$~$C_3$ alkoxy group which may be substituted with a same or different halogen atom, a cyano group, a nitro group, a methylsulfonyl group, a methylsulfinyl group, and a methylthio group, a pyridyl group which may be substituted with a halogen atom, or a pyrimidinyl group, m represents 1 or 2, and n represents 0 or 1.

12. A process for preparing an amino-acid amide derivative represented by the formula:

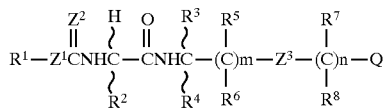

wherein $R^1$, $R^2$, $R^3$, $R^4$, $R^5$, $R^6$, $R^7$, $R^8$, $Z^1$, $Z^2$, $Z^3$, Q, m, and n have the same meanings as defined in claim 1, comprising the step of: reacting an amino acid derivative or the amino acid derivative with an activated carboxyl group, represented by the formula:

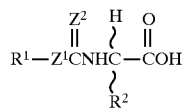

with an amine represented by the formula:

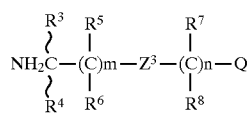

in the presence of a catalyst and /or a base as required.

13. A process for preparing an amino-acid amide derivative represented by the formula:

194

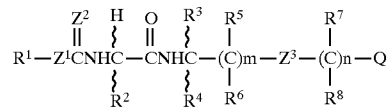

wherein $R^1$, $R^2$, $R^3$, $R^4$, $R^5$, $R^6$, $R^7$, $R^8$, $Z^1$, $Z^2$, $Z^3$, Q, m, and n have the same meanings as defined in claim 9, comprising the step of: reacting an activated carboxyl group, represented by the formula:

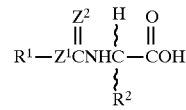

with an amine represented by the formula:

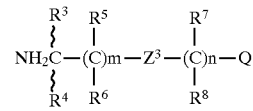

in the presence of a catalyst and/or a base.

14. An amino-acid amide derivative represented by the formula:

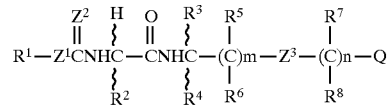

wherein $R^1$ represents (a) a lower alkyl group (optionally having at least one same or different substituent selected from the group consisting of a halogen atom, an alkoxy group, and a cyano group), (b) a lower alkenyl group, (c) a lower alkynyl group, (d) a cycloalkyl group (optionally having, at least one substituent selected from the group consisting of methyl group and a halogen atom), (e) a cycloalkylalkyl group, (f) a cycloalkenyl group, (g) a cyclic ether group, (h) a phenyl group (optionally having, at least one same or different substituent selected from the group consisting of a halogen atom, a lower alkyl group which may be substituted with a same or different halogen atom, a lower alkoxy group which may be substituted with a same or different halogen atom, a cyano group, and a nitro group), (i) an aralkyl group (optionally having at least one same or different substituent selected from the group consisting of a methyl group, a cyano group, and a nitro group), or (j) a heterocyclic group, $R^2$ represents a lower alkyl group, a lower alkenyl group, a cycloalkyl group, or a phenyl group (optionally having at least one substituent of halogen atom), $R^3$ represents a hydrogen atom or a lower alkyl group, $R^4$ represents a hydrogen atom, a lower alkyl group, or a cyano group, $R^5$, $R^6$, and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $Z^1$ and $Z^2$ independently represent an oxygen atom or a sulfur atom, $Z^3$ represents an oxygen atom, a sulfur atom, a group

(wherein $R^{10}$ represents a hydrogen atom, a methyl group, an acetyl group, a benzoyl group, a methoxycarbonyl group, or a methoxymethyl group), sulfinyl group, sulfonyl group, a group —C(O)O—, group

(wherein $R^{11}$ represents a hydrogen atom or a lower alkyl group),

Q represents (a) a cyclic ether group, (b) a heterocyclic group (optionally having, a substituent selected from the group consisting of a halogen atom, an alkyl group, a trifluoromethyl group, and a nitro group), or (c) a condensed heterocyclic group optionally having a substituent selected from the group consisting of a halogen atom and a nitro group, m represents an integer from 0 to 2, and n represents 0 or 1.

15. An amino-acid amide derivative as recited in claim 14, which is represented by the formula:

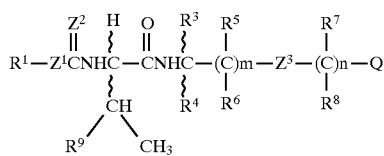

wherein $R^1$ represents a lower alkyl group (optionally having at least one same or different substituent selected from the group consisting of a halogen atom and an alkoxy group), a lower alkenyl group, a lower alkynyl group, a cycloalkyl group (optionally having at least one substituent of methyl group), a cycloalkenyl group, a cyclic ether group, an aralkyl group (optionally having at least one same or different substituent selected from the group consisting of a methyl group, a cyano group, and a nitro group), a phenyl group (optionally having at least one same or different substituents selected from the group consisting of a halogen atom, a methyl group, a methoxy group, a cyano group, a trifluoromethyl group, a trifluoromethoxy group, and a nitro group), or a heterocyclic group, $R^3$ represents a hydrogen atom or a lower alkyl group, $R^4$ represents a hydrogen atom, a lower alkyl group, or a cyano group, $R^5$, $R^6$ and $R^7$ independently represent a hydrogen atom or a lower alkyl group, $R^8$ represents a hydrogen atom, a lower alkyl group, an aralkyl group, a phenyl group, an alkoxycarbonyl group, or a cyano group, $R^9$ represents a hydrogen atom, a methyl group or an ethyl group, $Z^1$ and $Z^2$ independently represent an oxygen atom or a sulfur atom, $Z^3$ represents an oxygen atom, a sulfur atom, a group

(wherein $R^{10}$ represents a hydrogen atom, a methyl group, an acetyl group, a benzoyl group, a methoxycarbonyl group, or a methoxymethyl group), a sulfinyl group, or a sulfonyl group, Q represents a heterocyclic group (optionally having a substituent selected from the group consisting of a halogen atom and a nitro group), or a condensed heterocyclic group (optionally having a substituent selected from the group consisting of a halogen atom and a nitro group), m represents an integer from 0 to 2, and n represents 0 or 1.

16. An amino-acid amide derivative as recited in claim 14, which is represented by the formula:

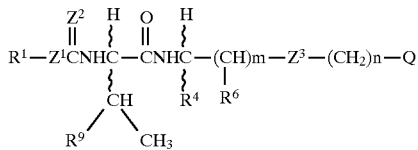

wherein $R^1$ represents a $C_1$~$C_6$ alkyl group (optionally having at least one same or different substituent selected from the group consisting of a halogen atom and an alkoxy group), a $C_2$~$C_6$ alkenyl group, a $C_2$~$C_6$ alkynyl group, a $C_3$~$C_8$ cycloalkyl group cycloalkyl group (optionally having at least one substituent of methyl group), a $C_2$~$C_8$ cyclic ether group, a $C_7$~$C_8$ aralkyl group (optionally having, at least one substituent of methyl group), or a phenyl group (optionally having at least one same or different substituent selected from the group consisting of a halogen atom, a methyl group, a methoxy group, a trifluoromethyl group, a trifluoromethoxy group, and a nitro group), $R^4$ represents a hydrogen atom, a $C_1$~$C_3$ alkyl group, or a cyano group, $R^6$ represents a hydrogen atom or a $C_1$~$C_3$ alkyl group, $R^9$ represents a hydrogen atom, a methyl group, or an ethyl group, $Z^1$ and $Z^2$ independently represent an oxygen atom or a sulfur atom, $Z^3$ represents an oxygen atom, a sulfur atom, a group $$\overset{|}{\underset{|}{N}}-R^{10}$$

(wherein $R^{10}$ represents a hydrogen atom, a methyl group, an acetyl group, or a benzoyl group), a sulfinyl group, or a sulfonyl group, m represents 1 or 2, and n represents 0 or 1.

17. An amino-acid amide derivative as recited in claim 14, which is represented by the formula:

$$R^1-O-\overset{O}{\underset{\|}{C}}-NH-\overset{H}{\underset{R^2}{C}}-\overset{O}{\underset{\|}{C}}-NH-\overset{H}{\underset{CH_3}{C}}-CH_2O-Q$$

wherein $R^1$ represents a $C_1$~$C_6$ alkyl group (optionally having at least one substituent cyano group), a $C_3$~$C_8$ cycloalkyl group (optionally having at least one substituent halogen atom), a $C_4$~$C_8$ cycloalkyl $C_1$~$C_3$ alkyl group, a benzyl group or a phenyl group (optionally having at least one same or different substituent selected from the group consisting of a halogen atom, a difluoromethoxy group, and a trifluoromethoxy group), $R^2$ represents a propyl group, an isopropyl group, an isobutyl group, a tert-butyl group, an isopropenyl group, a $C_3$~$C_8$ cycloalkyl group, or a phenyl group (optionally having at least one substituent halogen atom), and Q represents a pyridyl group (optionally having at least one substituent of a same or different halogen atom or trifluoromethyl group), or a pyrimidinyl group (optionally having at least one same or different substituent of a halogen atom or $C_1$~$C_3$ alkyl group).

18. An agricultural or horticultural fungicide composition which comprises an effective amount of an amino-acid derivative as claimed in claim 1.

19. An agricultural or horticultural fungicide composition which comprises an effective amount of an amino-acid amide derivative as recited in claim 19.

20. A process for preparing an amino-acid amide derivative represented by the formula:

$$R^1-Z^1\overset{Z^2}{\underset{\|}{C}}NH\overset{H}{\underset{R^2}{C}}-\overset{O}{\underset{\|}{C}}NH-\overset{R^3}{\underset{R^4}{C}}-(\overset{R^5}{\underset{R^6}{C}})m-Z^3-(\overset{R^7}{\underset{R^8}{C}})n-Q$$

wherein $R^1$, $R^2$, $R^3$, $R^4$, $R^5$, $R^6$, $R^7$, $R^8$, $Z^1$, $Z^2$, $Z^3$, Q, m, and n have the same meanings as defined in claim 14, comprising the step of: reacting an activated carboxyl group, represented by the formula:

$$R^1-Z^1\overset{Z^2}{\underset{\|}{C}}NH\overset{H}{\underset{R^2}{C}}-\overset{O}{\underset{\|}{C}}OH$$

with an amine represented by the formula:

$$NH_2\overset{R^3}{\underset{R^4}{C}}-(\overset{R^5}{\underset{R^6}{C}})m-Z^3-(\overset{R^7}{\underset{R^8}{C}})n-Q$$

in the presence of a catalyst and/or a base.

21. An agricultural or horticultural fungicide composition which comprises an effective amount of an amino-acid amide derivative as recited in claim 14.

22. The process of claim 13, wherein the inorganic acid is hydrochloride.

23. The process of claim 13, wherein the organic acid is tosylate.

24. The process of claim 20, wherein the inorganic acid is hydrochloride.

25. The process of claim 20, wherein the organic acid is tosylate.

* * * * *